(12) United States Patent
Hanada et al.

(10) Patent No.: US 12,152,049 B2
(45) Date of Patent: *Nov. 26, 2024

(54) STING AGONISTIC COMPOUND

(71) Applicant: ONO PHARMACEUTICAL CO., LTD., Osaka (JP)

(72) Inventors: Ryosuke Hanada, Osaka (JP); Masaya Kokubo, Osaka (JP); Masakuni Kurono, Osaka (JP); Kenichi Kouda, Osaka (JP); Hiroshi Hagiya, Osaka (JP)

(73) Assignee: ONO PHARMACEUTICAL CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/339,506

(22) Filed: Jun. 22, 2023

(65) Prior Publication Data

US 2023/0339992 A1 Oct. 26, 2023

Related U.S. Application Data

(63) Continuation of application No. 17/395,643, filed on Aug. 6, 2021, now Pat. No. 11,919,917, which is a continuation of application No. 17/264,179, filed as application No. PCT/JP2019/039941 on Oct. 10, 2019, now Pat. No. 11,130,773.

(30) Foreign Application Priority Data

Oct. 11, 2018 (JP) ................... 2018-192276

(51) Int. Cl.
*A61K 31/661* (2006.01)
*C07D 498/04* (2006.01)
*C07F 9/06* (2006.01)
*C07F 9/6561* (2006.01)

(52) U.S. Cl.
CPC .......... *C07F 9/6561* (2013.01); *A61K 31/661* (2013.01); *C07D 498/04* (2013.01); *C07F 9/062* (2013.01)

(58) Field of Classification Search
CPC ................................................ A61K 31/661
See application file for complete search history.

(56) References Cited

U.S. PATENT DOCUMENTS

| | | | |
|---|---|---|---|
| 11,130,773 | B2 | 9/2021 | Hanada et al. |
| 11,919,917 | B2 * | 3/2024 | Hanada .................... A61P 35/02 |
| 2009/0105245 | A1 | 4/2009 | Bingaman |
| 2017/0158724 | A1 | 6/2017 | Adams et al. |
| 2017/0233430 | A1 | 8/2017 | Adams et al. |
| 2018/0064745 | A1 | 3/2018 | Katibah et al. |
| 2018/0222982 | A1 | 8/2018 | Dranoff et al. |
| 2018/0258132 | A1 | 9/2018 | Adams et al. |
| 2019/0083626 | A1 | 3/2019 | Goldberg et al. |
| 2019/0153098 | A1 | 5/2019 | Goldberg et al. |
| 2020/0002370 | A1 | 1/2020 | Adams et al. |
| 2020/0179431 | A1 | 6/2020 | Katibah et al. |
| 2021/0253615 | A1 | 8/2021 | Hanada et al. |
| 2021/0363166 | A1 | 11/2021 | Hanada et al. |
| 2023/0141284 | A1 * | 5/2023 | Takeda .................... A61P 43/00 514/23 |

FOREIGN PATENT DOCUMENTS

| | | |
|---|---|---|
| CN | 107530415 A | 1/2018 |
| EP | 2 975 031 A1 | 1/2016 |
| EP | 3 661 499 | 2/2019 |
| JP | 2002069061 | 3/2002 |
| JP | 2018516903 A | 6/2018 |
| JP | 2018-522027 A | 8/2018 |
| JP | 2019-530658 A | 10/2019 |
| RU | 2018103881 A | 8/2019 |
| WO | 2017/093933 A1 | 6/2017 |
| WO | 2019/027857 A1 | 2/2019 |

(Continued)

OTHER PUBLICATIONS

Office Action dated Jul. 26, 2023, issued by Intellectual Property Office of Singapore in Singapore Patent Application No. 11202103573Y.
European Extended Search Report issued Nov. 27, 2023 issued by the European Patent Office for EP Patent Application No. 20930364.3.
International Search Report dated Nov. 12, 2019 issued by the International Searching Authority in counterpart International Application No. PCT/JP2019/039941 (PCT/ISA/210).
Communication dated Jul. 24, 2022 issued by the Singaporean Intellectual Property Office in counterpart Singaporean Application No. 11202103573Y.
International Search Report (PCT/ISA/210) dated Jun. 16, 2020, issued by the International Searching Authority in counterpart International Application No. PCT/JP2020/016064.

(Continued)

*Primary Examiner* — Laura L Stockton
(74) *Attorney, Agent, or Firm* — Sughrue Mion, PLLC

(57) ABSTRACT

A drug or agent containing a compound having an agonistic activity to STING as an active ingredient, where the compound is represented by the following general formula (I-1):

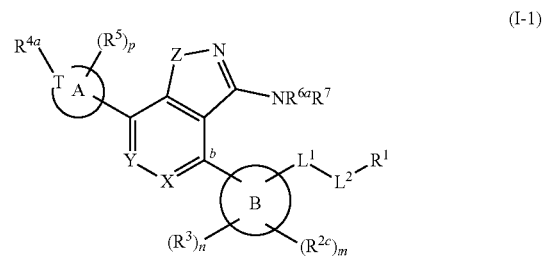

wherein all symbols represent the same meanings as described in the specification, and the compound can be used as an active ingredient of an agent for suppressing the progression of, suppressing the recurrence of and/or treating cancer or infectious disease.

8 Claims, 2 Drawing Sheets

(56) References Cited

FOREIGN PATENT DOCUMENTS

WO      2020/075790 A1     4/2020

OTHER PUBLICATIONS

Kosaka et al., "Combination of a STING agonist and dexamethasone induces antitumor effects," Proceedings of The Japanese Society of Pathology, vol. 105, No. 1, p. 1-58 of p. 392, 2016, Total 2 pages.
International Search Report (PCT/ISA/210) dated Jun. 29, 2021, issued by the International Searching Authority in counterpart International Application No. PCT/JP2021/014973.
Office Action dated Oct. 26, 2022, issued by the India Intellectual Property Office in counterpart Indian Patent Application No. 202147016729.
Petrovsky, B. V., "Big Medical Encyclopedia", Moscow, 1983, pp. 506-509 (4 pages), No Translation provided.
Belikov, V. G., "Pharmaceutical Chemistry", Chapter 2.6, "The relationship between the chemical structure, properties of substances and their effect on the body", MEDpress-inform, Moscow, 2007, pp. 27-29 (11 pages).
Communication dated Dec. 29, 2022 issued by the Russian Patent Office in application No. 2021109317.
Communication dated Feb. 11, 2023, issued by the China National Intellectual Property Administration in counterpart Chinese Application No. 201980067222.6.
Communication dated Jul. 25, 2023 by the Japanese Patent Office for Japanese Patent Application No. 2020-170203.
Communication issued Oct. 19, 2023 by Mexican Patent Office in corresponding Mexican Application No. 2021/003958.
Extended European Search Report dated Apr. 17, 2024 in European Application No. 21785563.4.
Hearing Notice issued on Aug. 12, 2024 by the India Intellectual Property Office in Indian Patent Application No. 202147016729.
Communication dated Sep. 10, 2024, issued by the Korean Patent Office in Korean Application No. 10-2021-7010621.
Communication dated Sep. 10, 2024, issued by the Intellectual Property Corporation of Malaysia in Malaysian Application No. PI2021001914.

* cited by examiner

STING AGONISTIC COMPOUND

CROSS-REFERENCE TO RELATED APPLICATIONS

This application is a Continuation of U.S. application Ser. No. 17/395,643, filed Aug. 6, 2021, which is a Continuation of U.S. application Ser. No. 17/264,179, filed Jan. 28, 2021, now U.S. Pat. No. 11,130,773, issued Sep. 28, 2021, which is a National Phase Entry of PCT International Application No. PCT/JP2019/039941, filed on Oct. 10, 2019, which claims priority from Japanese Patent Application No. 2018-192276 filed on Oct. 11, 2018, the contents of all of which are incorporated herein by reference in their entirety.

TECHNICAL FIELD

The present invention relates a compound represented by the general formula (I):

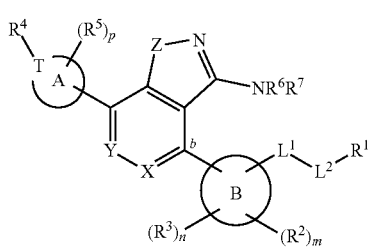

[wherein, all symbols have the same meanings as described below], an N-oxide thereof, a prodrug thereof, a pharmaceutically acceptable salt thereof or a solvate thereof, and a compound represented by the general formula (I-1):

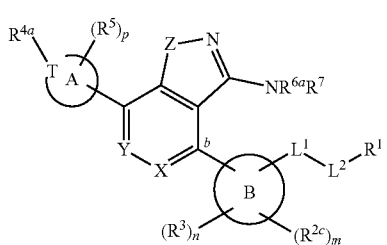

[wherein, all symbols have the same meanings as described below], an N-oxide thereof, a pharmaceutically acceptable salt thereof, or a solvate thereof (hereinafter, these compounds may be described as "the compound of the present invention"), and a pharmaceutical composition containing any one of these compounds as an active ingredient, and pharmaceutical uses thereof.

BACKGROUND ART

It is known that STING (Stimulation of Interferon Genes) is an endoplasmic reticulum localized type four-transmembrane protein and is involved in innate immunity. When foreign double-stranded DNAs appear in cytoplasm due to infection or the like, cyclic GMP-AMP synthase (cGAS) is activated and cyclic GMP-AMP (cGAMP) is synthesized. This cGAMP binds to STING on endoplasmic reticulum and induces type I interferon (IFN) production. On the other hand, it is known that cyclic dinucleotides such as cyclic Di-GMP, which were first identified as a second messenger of bacteria and later confirmed to also exist in mammals, also directly bind to STING and activate it (Non-Patent Literature 1).

Furthermore, STING is also known to be involved in autoimmune diseases and tumor immunity. For example, it has been indicated that abnormal host DNAs leak from the nucleus and activate STING to induce pro-inflammatory responses, which have been implicated in autoimmune disease. The STING pathway also detects tumor-derived DNAs and promotes T cell responses to tumors. It is known that a STING agonistic compound administered to mouse tumors induces adaptive immune response to cause tumor regression (Non-Patent Literature 2), and that an activating molecule of the STING pathway enhances IFN production and exhibits antiviral effects. (Non-Patent Literature 3).

Heretofore, as STING agonist compounds, the compounds which are so-called cyclic dimerized nucleic acids as disclosed in Patent Literatures 1 to 3 and non-cyclic dimerized nucleic acids as disclosed in Patent Literatures 4 to 7 have been reported. However, no STING agonist compound having a structure like the compound of the present invention has been reported.

CITATION LIST

Patent Literature

Patent Literature 1: International Publication No. 2017/093933
Patent Literature 2: International Publication No. 2017/186711
Patent Literature 3: International Publication No. 2017/106740
Patent Literature 4: International Publication No. 2017/175156
Patent Literature 5: US Patent Application Publication No. 2017/0050967 Publication
Patent Literature 6: US Patent Application Publication No. 2017/0146519 Publication
Patent Literature 7: International Publication No. 2018/067423

Non-Patent Literature

Non-Patent Literature 1: Devaux L. et. al., Curr. Opi. Microbiol. 41, 21-28 (2018)
Non-Patent Literature 2: Corrales L. et. al., Cell Rep. 11 (7), 1018-1030 (2015)
Non-Patent Literature 3: Sali T. M. et. al., PLoS Pathog., 11 (12): e1005324

SUMMARY OF INVENTION

Technical Problem

The object of the present invention is to provide a drug containing a compound having agonistic activity to STING as an active ingredient.

Solution to Problem

The present inventors have conducted extensive studies to find compounds having agonistic activity to STING, and as a result, found the following compounds and then completed the present invention.

That is, the present invention is as follows.

[1] A compound represented by the general formula (I):

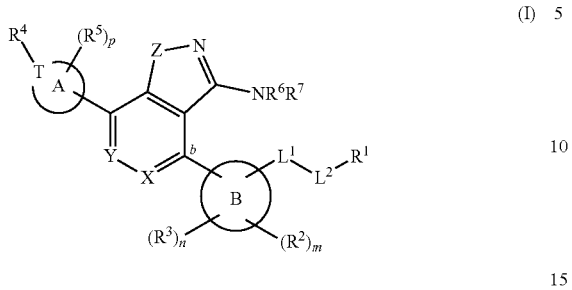

[wherein, X and Y represent —CH= or a nitrogen atom (provided that both X and Y do not represent —CH=, simultaneously), respectively, Z represents an oxygen atom or sulfur atom, T represents a carbon atom or nitrogen atom, Ring A represents a 5 to 7-membered monocycle, Ring B represents a 5 to 7-membered monocycle or 8 to 10-membered bicycle, $L^1$ represents a bond, —O—, —CONH—, —CO—, —CO$_2$—, —S—, —SO$_2$— or —SO—, $L^2$ represents a bond, C1-3 alkylene group, C3-7 cycloalkylene group or phenylene group, $R^1$ represents a hydrogen atom, halogen atom, hydroxyl group, cyano group, N($R^{1a}$)$_2$ (herein, two $R^{1a}$s represent each independently a hydrogen atom or C1-4 alkyl group), C1-4 alkyl group, carboxy group, C1-4 alkoxycarbonyl group, C1-4 haloalkyl group, methyl-d$_3$ group, C3-7 cycloalkyl group, phenyl group or 3 to 7-membered monocyclic non-aromatic heterocycle, $R^2$ represents a hydrogen atom, halogen atom, hydroxyl group, oxo group, nitro group, cyano group, C1-4 alkoxy group or —CH$_2$NR$^{2a}$R$^{2b}$ or NR$^{2a}$R$^{2b}$ (herein, R$_{2a}$ represents a hydrogen atom or C1-4 alkyl group, R$^{2b}$ represents a hydrogen atom), m represents an integer of 0 or 1, $R^3$ represents a hydrogen atom, halogen atom, hydroxyl group, C1-4 alkyl group, C1-4 alkoxy group, C1-4 haloalkyl group, C1-4 haloalkoxy group or amino group, and n represents an integer of 1 to 16 (herein, when n is two or more, the groups represented by a plurality of $R^3$s may be the same or different), $R^4$ represents a hydrogen atom, C1-4 alkyl group or carboxy group, and $R^5$ represents a C1-4 alkyl group, p represents an integer of 0 to 5 (herein, when p is 2 or more, the groups represented by a plurality of $R^5$s may be the same or different), and $R^6$ represents a hydrogen atom or C1-4 alkyl group, $R^7$ is a hydrogen atom. Further, b represents the bonding position of Ring B.], an N-oxide thereof, a prodrug thereof, a pharmaceutically acceptable salt thereof, or a solvate thereof;

[2] the compound, N-oxide thereof, prodrug thereof, pharmaceutically acceptable salt thereof, or solvate thereof, according to the preceding item [1], wherein Ring A is (a) a C5-6 monocyclic carbocycle or (b) a 5 to 6-membered monocyclic heterocycle containing 1 to 4 heteroatoms selected from an oxygen atom, nitrogen atom and sulfur atom;

[3] the compound, N-oxide thereof, prodrug thereof, pharmaceutically acceptable salt thereof, or solvate thereof, according to the preceding item [1] or [2], wherein Ring B is (a) a C5-6 monocyclic carbocycle or (b) a 5 to 6-membered monocyclic heterocycle containing 1 to 4 heteroatoms selected from an oxygen atom, nitrogen atom and sulfur atom;

[4] the compound, N-oxide thereof, prodrug thereof, pharmaceutically acceptable salt thereof, or solvate thereof, according to the preceding item [1] or [3], wherein Ring A is (a) a benzene ring or (b) a 5 to 6-membered monocyclic aromatic heterocycle containing 1 to 4 heteroatoms selected from an oxygen atom, nitrogen atom and sulfur atom;

[5] the compound, N-oxide thereof, prodrug thereof, pharmaceutically acceptable salt thereof, or solvate thereof, according to any one of the preceding items [1], [2] and [4], wherein Ring B is (a) a benzene ring or (b) a 5 to 6-membered monocyclic aromatic heterocycle containing 1 to 4 heteroatoms selected from an oxygen atom, nitrogen atom and sulfur atom;

[6] the compound, N-oxide thereof, prodrug thereof, pharmaceutically acceptable salt thereof, or solvate thereof, according to any one of the preceding items [1], [3] and [5], wherein Ring A is a 5 to 6-membered monocyclic aromatic nitrogen-containing heterocycle containing 1 to 4 nitrogen atoms, without any other heteroatoms;

[7] the compound, N-oxide thereof, prodrug thereof, pharmaceutically acceptable salt thereof, or solvate thereof, according to any one of the preceding items [1] to [6], wherein Z is an oxygen atom;

[8] the compound, N-oxide thereof, prodrug thereof, pharmaceutically acceptable salt thereof, or solvate thereof, according to any one of the preceding items [1] to [7], wherein X is a nitrogen atom, and Y is —CH=;

[9] the compound, N-oxide thereof, prodrug thereof, pharmaceutically acceptable salt thereof, or solvate thereof, according to any one of the preceding items [1] to [8], wherein

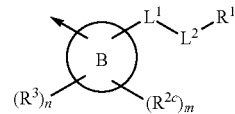

[wherein, the arrow is bound to the carbon atom represented by b in the general formula (I), and other symbols represent the same meanings as described above.] of the general formula (I) is the group represented by the following formula (Ib):

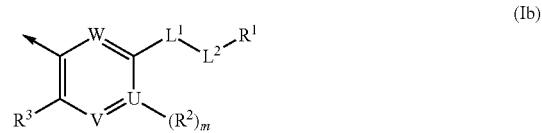

[wherein, U represents a nitrogen atom or carbon atom (herein, when U represents a nitrogen atom, m represents 0, and when U represents a carbon atom, m represents 1), W represents —CR$^3$= or a nitrogen atom, V represents —CH= or a nitrogen atom, and when the formula (Ib) has a plurality of $R^3$s, the groups represented by them may be the same or different, and other symbols represent the same meaning as described above.];

[10] the compound, N-oxide thereof, prodrug thereof, pharmaceutically acceptable salt thereof, or solvate thereof, according to the preceding item [1], wherein the compound represented by the general formula (I) is the compound represented by the general formula (II)

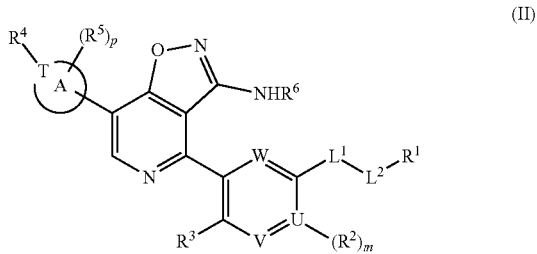

(II)

[wherein, all symbols have the same meanings as described above.];
[11] the compound, N-oxide thereof, prodrug thereof, pharmaceutically acceptable salt thereof or solvate thereof, according to any one of the preceding items [1] to [10], wherein T is a nitrogen atom;
[12] the compound, N-oxide thereof, prodrug thereof, pharmaceutically acceptable salt thereof or solvate thereof, according to any one of the preceding items [9] to [11], wherein U is a carbon atom;
[13] the compound, N-oxide thereof, prodrug thereof, pharmaceutically acceptable salt thereof or solvate thereof, according to any one of the preceding items [1], [3], [5] and [7] to [12], wherein Ring A is pyrazole, triazole (e.g., 1,2,3-triazole and 1,2,4-triazole), tetrazole, oxazole, isoxazole, imidazole, thiazole or isothiazole;
[14] the compound, N-oxide thereof, prodrug thereof, pharmaceutically acceptable salt thereof or solvate thereof, according to the preceding item [1], wherein the compound represented by the general formula (I) is the compound represented by the general formula (III):

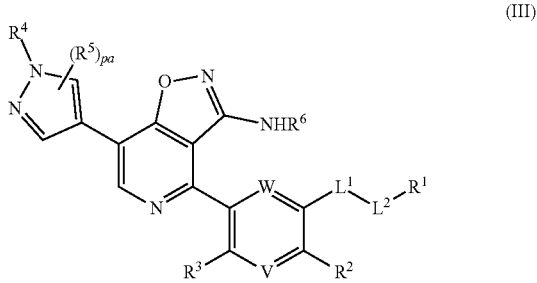

(III)

[wherein, pa represents an integer of 0 to 2, and other symbols represent the same meanings as described above.];
[15] the compound, N-oxide thereof, prodrug thereof, pharmaceutically acceptable salt thereof or solvate thereof, according to any one of the preceding items [1] to [14], wherein $L^2$ in the general formula (I), general formula (II) and general formula (III) (hereinafter, may be abbreviated as "the general formula (I) or the like") is a bond or C1-3 alkylene group;
[16] the compound, N-oxide thereof, prodrug thereof, pharmaceutically acceptable salt thereof or solvate thereof, according to any one of the preceding items [1] to [15], wherein $L^1$ in the general formula (I) or the like is —O—, —CONH—, —CO—, —CO$_2$—, —S—, —SO$_2$— or —SO—;
[17] the compound, N-oxide thereof, prodrug thereof, pharmaceutically acceptable salt thereof or solvate thereof, according to any one of the preceding items [1] to [15], wherein $L^1$ in the general formula (I) or the like is —CONH— (provided that the left side of the group is bound to Ring B), —CO—, —CO$_2$—, —S—, —SO$_2$— or —SO—;
[18] the compound, N-oxide thereof, prodrug thereof, pharmaceutically acceptable salt thereof or solvate thereof, according to any one of the preceding items [1] to [17], wherein $R^1$ is a hydrogen atom, hydroxyl group, C1-4 alkyl group or carboxy group;
[19] the compound, N-oxide thereof, prodrug thereof, pharmaceutically acceptable salt thereof or solvate thereof, according to any one of the preceding items [1] to [17], wherein $R^1$ is a hydrogen atom or C1-4 alkyl group;
[20] the compound, N-oxide thereof, prodrug thereof, pharmaceutically acceptable salt thereof or solvate thereof, according to any one of the preceding items [1] to [19], wherein $R^2$ is a nitro group or $NR^{2a}R^{2b}$;
[21] the compound, N-oxide thereof, prodrug thereof, pharmaceutically acceptable salt thereof or solvate thereof, according to any one of the preceding items [1] to [20], wherein both of $R^{2a}$ and $R^{2b}$ are hydrogen atoms;
[22] the compound, N-oxide thereof, prodrug thereof, pharmaceutically acceptable salt thereof or solvate thereof, according to any one of the preceding items [1] to [21], wherein $R^3$ is a hydrogen atom, halogen atom or hydroxyl group;
[23] the compound, N-oxide thereof, prodrug thereof, pharmaceutically acceptable salt thereof or solvate thereof, according to any one of the preceding items [1] to [22], wherein $R^4$ is a hydrogen atom;
[24] the compound, N-oxide thereof, prodrug thereof, pharmaceutically acceptable salt thereof or solvate thereof, according to any one of the preceding items [1] to [23], wherein $R^6$ is a hydrogen atom;
[25] the compound, N-oxide thereof, prodrug thereof, pharmaceutically acceptable salt thereof or solvate thereof, according to any one of the preceding items [1] to [24], wherein p and pa are zero or 1;
[26] the compound, N-oxide thereof, prodrug thereof, pharmaceutically acceptable salt thereof or solvate thereof, according to the preceding item [1], wherein the compound represented by the general formula (I) is the compound selected from the group consisting of:
(1) 4-(4-amino-2-fluoro-5-methoxyphenyl)-7-(1H-pyrazol-4-yl)isoxazolo[5,4-c]pyridin-3-amine,
(2) 4-(4-amino-2-fluoro-5-methoxyphenyl)-7-(1H-pyrazol-4-yl)isoxazolo[4,5-c]pyridin-3-amine,
(3) 4-(4-amino-3-methoxy phenyl)-7-(1H-pyrazol-4-yl)isoxazolo[4,5-c]pyridin-3-amine,
(4) 4-(4-amino-2-fluoro-5-(methylthio)phenyl)-7-(1H-pyrazol-4-yl)isoxazolo[4,5-c]pyridin-3-amine,
(5) 4-(4-amino-2-fluoro-5-(methoxy-d$_3$)phenyl)-7-(1H-pyrazol-4-yl)isoxazolo[4,5-c]pyridin-3-amine, (6) 4-(4-amino-2-fluoro-5-(methyl sulfonyl)phenyl)-7-(1H-pyrazol-4-yl)isoxazolo[4,5-c]pyridin-3-amine, (7) 4-(4-amino-5-(ethylthio)-2-fluorophenyl)-7-(1H-pyrazol-4-yl)isoxazolo[4,5-c]pyridin-3-amine, (8) 4-(4-amino-2-fluoro-5-(methylsulfinyl)phenyl)-7-(1H-pyrazol-4-yl)isoxazolo[4,5-c]pyridin-3-amine, (9) 4-(4-amino-2-fluoro-3-methoxyphenyl)-7-(1H-pyrazol-4-yl)isoxazolo[4,5-c]pyridin-3-amine,

(10) methyl 2-amino-5-(3-amino-7-(1H-pyrazol-4-yl)isoxazolo[4,5-c]pyridin-4-yl)-4-fluorobenzoate,

(11) 2-amino-5-(3-amino-7-(1H-pyrazol-4-yl)isoxazolo[4,5-c]pyridin-4-yl)-4-fluorobenzoic acid,

(12) 2-amino-5-(3-amino-7-(1H-pyrazol-4-yl)isoxazolo[4,5-c]pyridin-4-yl)-4-fluorobenzamide,

(13) 4-(4-amino-2-fluoro-5-methoxyphenyl)-7-(3-methyl-1H-pyrazol-4-yl)isoxazolo[4,5-c]pyridin-3-amine,

(14) 1-(2-amino-5-(3-amino-7-(1H-pyrazol-4-yl)isoxazolo[4,5-c]pyridin-4-yl)-4-fluorophenyl)ethan-1-one,

(15) 4-(4-amino-2-chloro-5-(methylthio)phenyl)-7-(1H-pyrazol-4-yl)isoxazolo[4,5-c]pyridin-3-amine,

(16) ethyl 2-amino-5-(3-amino-7-(1H-pyrazol-4-yl)isoxazolo[4,5-c]pyridin-4-yl)-4-fluorobenzoate,

(17) 2-amino-5-(3-amino-7-(1H-pyrazol-4-yl)isoxazolo[4,5-c]pyridin-4-yl)-4-fluoro-N-methylbenzamide,

(18) 1-(2-amino-5-(3-amino-7-(1H-pyrazol-4-yl)isoxazolo[4,5-c]pyridin-4-yl)-4-fluorophenyl)propan-1-one,

(19) 2-amino-5-(3-amino-7-(1H-pyrazol-4-yl)isoxazolo[4,5-c]pyridin-4-yl)-N-ethyl-4-fluorobenzamide,

(20) 1-(2-amino-5-(3-amino-7-(1H-pyrazol-4-yl)isoxazolo[4,5-c]pyridin-4-yl)phenyl)ethan-1-one,

(21) methyl 2-amino-5-(3-amino-7-(1H-pyrazol-4-yl)isoxazolo[4,5-c]pyridin-4-yl)benzoate,

(22) 2-amino-5-(3-amino-7-(1H-pyrazol-4-yl)isoxazolo[4,5-c]pyridin-4-yl)-N-propylbenzamide,

(23) 1-(2-amino-5-(3-amino-7-(1H-pyrazol-4-yl)isoxazolo[4,5-c]pyridin-4-yl)-4-fluorophenyl)butan-1-one,

(24) 2-amino-5-(3-amino-7-(1H-pyrazol-4-yl)isoxazolo[4,5-c]pyridin-4-yl)-4-fluoro-N-propylbenzamide,

(25) 1-(2-amino-5-(3-amino-7-(1H-pyrazol-4-yl)isoxazolo[4,5-c]pyridin-4-yl)phenyl)butan-1-one,

(26) 2-hydroxyethyl 2-amino-5-(3-amino-7-(1H-pyrazol-4-yl)isoxazolo[4,5-c]pyridin-4-yl)-4-fluorobenzoate,

(27) 2-amino-5-(3-amino-7-(1H-pyrazol-4-yl)isoxazolo[4,5-c]pyridin-4-yl)benzamide,

(28) 2-amino-5-(3-amino-7-(1H-pyrazol-4-yl)isoxazolo[4,5-c]pyridin-4-yl)-N-methylbenzamide,

(29) 1-(2-amino-5-amino-7-(1H-pyrazol-4-yl)isoxazolo[4,5-c]pyridin-4-yl)-4-hydroxyphenyl)ethan-1-one,

(30) 2-amino-5-(3-amino-7-(1H-pyrazol-4-yl)isoxazolo[4,5-c]pyridin-4-yl)-N-ethylbenzamide,

(31) 1-(2-amino-5-amino-7-(1H-pyrazol-4-yl)isoxazolo[4,5-c]pyridin-4-yl)phenyl)propan-1-one,

(32) 2-amino-5-amino-7-(1H-pyrazol-4-yl)isoxazolo[4,5-c]pyridin-4-yl)-4-chloro-N-ethylbenzamide,

(33) 4-(2-fluoro-5-methoxy-4-nitrophenyl)-7-(1H-pyrazol-4-yl)isoxazolo[4,5-c]pyridin-3-amine,

(34) (2-amino-5-(3-amino-7-(1H-pyrazol-4-yl)isothiazolo[4,5-c]pyridin-4-yl)-4-fluorophenyl)ethan-1-one, and

(35) (4-amino-2-fluoro-5-(trifluoromethyl)phenyl)-7-(1H-pyrazol-4-yl)isoxazolo[4,5-c]pyridin-3-amine;

[1-1] a compound represented by the general formula (I-1):

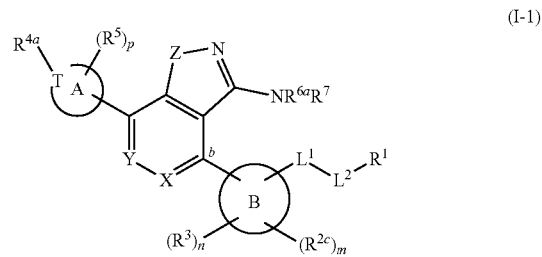

(I-1)

[wherein, $R^{2c}$ represents a hydrogen atom, hydroxyl group, halogen atom, oxo group, nitro group, cyano group, C1-4 alkoxy group or —$CH_2NR^{2d}R^{2e}$ or $NR^{2d}R^{2e}$ (herein, $R^{2d}$ is a hydrogen atom, C1-4 alkyl group or $R^{FR}$, and $R^{2c}$ represents a hydrogen atom), $R^{4a}$ represents a hydrogen atom, C1-4 alkyl group, carboxy group or $R^{FR}$, $R^{6a}$ represents a hydrogen atom, C1-4 alkyl group or $R^{FR}$, and $R^{FR}$ represents:

(i) —$(CR^{Fb}_2)_qOP(=O)(OR^{Fa})_2$ [wherein, $R^{Fa}$ represents each independently a hydrogen atom, C1-4 alkyl group, C3-6 cycloalkyl group, —$(CH_2)_2OH$ or —$CH_2OCO_2CH(CH_3)_2$, $R^{Fb}$ represents a hydrogen atom or methyl group, and q represents an integer of 1 or 2 (herein, the groups represented by a plurality of $R^{Fb}$s may be the same or different).] (hereinafter, the group —$(CR^{Fb}_2)_qOP(=O)(OR^{Fa})_2$ may be collectively referred to as a "phosphonooxyalkyl group"), or (ii) a free radical group producing a compound represented by the general formula (I), N-oxide thereof, pharmaceutically acceptable salt thereof or solvate thereof, as a result of decomposition in vivo, and other symbols represent the same meanings as defined above, provided that two or more of $R^{2d}$, $R^{4a}$ and $R^{6a}$ do not represent $R^{FR}$, simultaneously.], an N-oxide thereof, a pharmaceutically acceptable salt thereof or a solvate thereof;

[1-2] the compound, N-oxide thereof, pharmaceutically acceptable salt thereof or solvate thereof, according to the preceding item [1-1], wherein Ring A is (a) a C5-6 monocyclic carbocycle or (b) a 5 to 6-membered monocyclic heterocycle containing 1 to 4 heteroatoms selected from an oxygen atom, nitrogen atom and sulfur atom;

[1-3] the compound, N-oxide thereof, pharmaceutically acceptable salt thereof or solvate thereof, according to the preceding item [1-1] or [1-2], wherein Ring B is (a) a C5-6 monocyclic carbocycle or (b) a 5 to 6-membered monocyclic heterocycle containing 1 to 4 heteroatoms selected from an oxygen atom, nitrogen atom and sulfur atom;

[1-4] the compound, N-oxide thereof, pharmaceutically acceptable salt thereof or solvate thereof, according to the preceding item [1-1] or [1-3], wherein Ring A is (a) a benzene ring or (b) a 5 to 6-membered monocyclic aromatic heterocycle containing 1 to 4 heteroatoms selected from an oxygen atom, nitrogen atom and sulfur atom;

[1-5] the compound, N-oxide thereof, pharmaceutically acceptable salt thereof or solvate thereof, according to any one of the preceding items [1-1], [1-2] and [1-4], wherein Ring B is (a) a benzene ring or (b) a 5 to 6-membered monocyclic aromatic heterocycle containing 1 to 4 heteroatoms selected from an oxygen atom, nitrogen atom and sulfur atom;

[1-6] the compound, N-oxide thereof, pharmaceutically acceptable salt thereof or solvate thereof, according to any one of the preceding items [1-1], [1-3] and [1-5], wherein Ring A is a to 6-membered monocyclic aromatic nitrogen-containing heterocycle containing 1 to 4 nitrogen atoms, without any other heteroatoms;

[1-7] the compound, N-oxide thereof, pharmaceutically acceptable salt thereof or solvate thereof, according to any one of the preceding items [1-1] to [1-6], wherein Z is an oxygen atom;

[1-8] the compound, N-oxide thereof, pharmaceutically acceptable salt thereof or solvate thereof, according to any one of the preceding items [1-1] to [1-7], wherein X is a nitrogen atom and Y is —CH═;

[1-9] the compound, N-oxide thereof, pharmaceutically acceptable salt thereof, or solvate thereof, according to any one of the preceding items [1-1] to [1-8], wherein

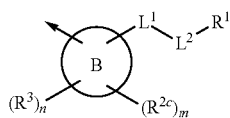

[wherein, the arrow is bound to the carbon atom represented by b in the general formula (I-1), and other symbols represent the same meanings as described above.] of the general formula (I-1) is the group represented by the formula (Ib-1):

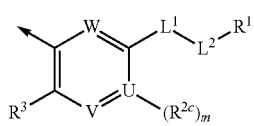

(Ib-1)

[wherein, all symbols represent the same meaning as described above.];

[1-10] the compound, N-oxide thereof, pharmaceutically acceptable salt thereof, or solvate thereof, according to the preceding item [1-1], wherein the compound represented by the general formula (I-1) is the compound represented by the general formula (II-1):

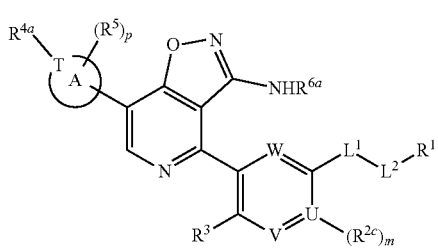

(II-1)

[wherein, all symbols represent the same meanings as described above.];

[1-11] the compound, N-oxide thereof, pharmaceutically acceptable salt thereof or solvate thereof, according to any one of the preceding items [1-1] to [1-10], wherein T is a nitrogen atom;

[1-12] the compound, N-oxide thereof, pharmaceutically acceptable salt thereof or solvate thereof, according to any one of the preceding items [1-9] to [1-11], wherein U is a carbon atom;

[1-13] the compound, N-oxide thereof, pharmaceutically acceptable salt thereof or solvate thereof, according to any one of the preceding items [1-1], [1-3], [1-5] and [1-7] to [1-12], wherein Ring A is pyrazole, triazole (e.g., 1,2,3-triazole and 1,2,4-triazole), tetrazole, oxazole, isoxazole, imidazole, thiazole or isothiazole;

[1-14] the compound, N-oxide thereof, pharmaceutically acceptable salt thereof or solvate thereof, according to the preceding item [1-1], wherein the compound represented by the general formula (I-1) is the compound represented by the general formula (III-1):

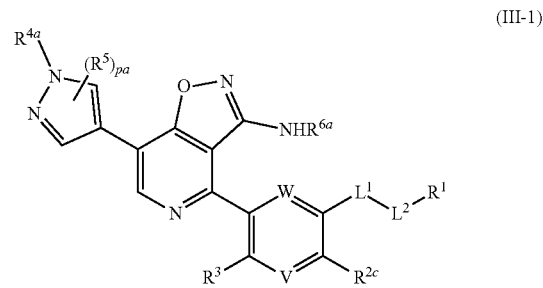

(III-1)

[wherein, all symbols represent the same meanings as described above.];

[1-15] the compound, N-oxide thereof, pharmaceutically acceptable salt thereof or solvate thereof, according to any one of the preceding items [1-1] to [1-14], wherein $L^2$ in the general formula (I-1), general formula (II-1) and general formula (III-1) (hereinafter, may be abbreviated as "the general formula (I-1) or the like") is a bond or C1-3 alkylene group;

[1-16] the compound, N-oxide thereof, pharmaceutically acceptable salt thereof or solvate thereof, according to any one of the preceding items [1-1] to [1-15], wherein $L^1$ in the general formula (I-1) or the like is —O—, —CONH—, —CO—, —CO$_2$—, —S—, —SO$_2$— or —SO—;

[1-17] the compound, N-oxide thereof, pharmaceutically acceptable salt thereof or solvate thereof, according to any one of the preceding items [1-1] to [1-15], wherein $L^1$ in the general formula (I-1) or the like is —CONH— (provided that the left side of the group is bound to Ring B), —CO—, —CO$_2$—, —S—, —SO$_2$— or —SO—;

[1-18] the compound, N-oxide thereof, pharmaceutically acceptable salt thereof or solvate thereof, according to any one of the preceding items [1-1] to [1-17]; wherein $R^1$ is a hydrogen atom, hydroxyl group, C1-4 alkyl group or carboxy group;

[1-19] the compound, N-oxide thereof, pharmaceutically acceptable salt thereof or solvate thereof, according to any one of the preceding items [1-1] to [1-17]; wherein $R^1$ is a hydrogen atom or C1-4 alkyl group;

[1-20] the compound, N-oxide thereof, pharmaceutically acceptable salt thereof or solvate thereof, according to any one of the preceding items [1-1] to [1-19], wherein $R^{2e}$ is a nitro group or $NR^{2d}R^{2e}$;

[1-21] the compound, N-oxide thereof, pharmaceutically acceptable salt thereof or solvate thereof, according to any one of the preceding items [1-1] to [1-20], wherein $R^3$ is a hydrogen atom, halogen atom or hydroxyl group;

[1-22] the compound, N-oxide thereof, pharmaceutically acceptable salt thereof or solvate thereof, according to any one of the preceding items [1-1] to [1-21], wherein $R^{2d}$ is a hydrogen atom or $R^{FR}$;

[1-23] the compound, N-oxide thereof, pharmaceutically acceptable salt thereof or solvate thereof, according to any one of the preceding items [1-1] to [1-22], wherein both of $R^{4a}$ and $R^{6a}$ are hydrogen atoms;

[1-24] the compound, N-oxide thereof, pharmaceutically acceptable salt thereof or solvate thereof, according to any one of the preceding items [1-1] to [1-21], wherein $R^{4a}$ is a hydrogen atom or $R^{FR}$;

[1-25] the compound, N-oxide thereof, pharmaceutically acceptable salt thereof or solvate thereof, according to any one of the preceding items [1-1] to [1-21] and [1-24], wherein both of $R^{2d}$ and $R^{6a}$ are hydrogen atoms;

[1-26] the compound, N-oxide thereof, pharmaceutically acceptable salt thereof or solvate thereof, according to any one of the preceding items [1-1] to [1-21], wherein $R^{6a}$ is a hydrogen atom or $R^{FR}$;

[1-27] the compound, N-oxide thereof, pharmaceutically acceptable salt thereof or solvate thereof according to any one of the preceding items [1-1] to [1-21] and [1-26], wherein both of $R^{2d}$ and $R^{4a}$ are hydrogen atoms;

[1-28] the compound, N-oxide thereof, pharmaceutically acceptable salt thereof or solvate thereof, according to any one of the preceding items [1-1] to [1-27], wherein $R^{FR}$ is $-(CR^{Fb}{}_2)_qOP(=O)(OR^{Fa})_2$ [wherein, all symbols represent the same meanings as described above.];

[1-29] the compound, N-oxide thereof, pharmaceutically acceptable salt thereof or solvate thereof, according to the preceding item [1-28], wherein $-(CR^{Fb}{}_2)_qOP(=O)(OR^{Fa})_2$ represented by $R^{FR}$ is $-CH_2OP(=O)(OH)_2$, $-CH(CH_3)OP(=O)(OH)_2$ or $CH_2OP(=O)(OH)(OCH_2OCO_2CH(CH_3)_2)$;

[1-30] the pharmaceutically acceptable salt of the compound or the solvate thereof, according to any one of the preceding items [1-1] to [1-28], wherein $R^{FR}$ is $-(CR^{Fb}{}_2)_qOP(=O)(OR^{Fa})_2$ and the pharmaceutically acceptable salt described in any one of the preceding items [1-1] to [1-28] is an alkali metal salt (e.g., a lithium salt, sodium salt or potassium salt), alkaline earth metal salt (e.g., a calcium salt), magnesium salt, zinc salt, ammonium salt or organic amine salt, formed together with the same group;

[1-31] the pharmaceutically acceptable salt of the compound or the solvate thereof, according to the preceding item [1-30], wherein the organic amine salt is an aliphatic amine salt (e.g., methylamine salt, dimethylamine salt, cyclopentylamine salt, trimethylamine salt, triethylamine salt, dicyclohexylamine salt, monoethanolamine salt, diethanolamine salt, triethanolamine salt, procaine salt, meglumine salt, tris(hydroxymethyl) aminomethane salt or ethylenediamine salt, etc.), aralkylamine salt (e.g., benzylamine salt, phenethylamine salt, N, N-dibenzylethylenediamine salt or benetamine salt, etc.), heterocyclic aromatic amine salt (e.g., piperidine salt, pyridine salt, picoline salt, quinoline salt or isoquinoline salt, etc.), quaternary ammonium salt (e.g., tetramethylammonium salt, tetraethylammonium salt, benzyltrimethylammonium salt, benzyltriethylammonium salt, benzyltributylammonium salt, methyltrioctylammonium salt or tetrabutylammonium salt, etc.), basic amino acid salt (e.g., arginine salt or lysine salt, etc.) or N-methyl-D-glucamine salt;

[1-32] the compound, N-oxide thereof, pharmaceutically acceptable salt thereof or solvate thereof, according to any one of the preceding items [1-1] to [1-31], wherein p and pa are zero or 1;

[1-33] the compound, N-oxide thereof, pharmaceutically acceptable salt thereof or solvate thereof, according to the preceding item [1-1], wherein the compound represented by the general formula (I-1) is the compound selected from the group consisting of:

(1) 4-(4-amino-2-fluoro-5-methoxyphenyl)-7-(1H-pyrazol-4-yl)isoxazolo[5,4-c]pyridin-3-amine,
(2) 4-(4-amino-2-fluoro-5-methoxyphenyl)-7-(1H-pyrazol-4-yl)isoxazolo[4,5-c]pyridin-3-amine,
(3) 4-(4-amino-3-methoxy phenyl)-7-(1H-pyrazol-4-yl)isoxazolo[4,5-c]pyridin-3-amine, (4) 4-(4-amino-2-fluoro-5-(methylthio)phenyl)-7-(1H-pyrazol-4-yl)isoxazolo[4,5-c]pyridin-3-amine,
(5) 4-(4-amino-2-fluoro-5-(methoxy-$d_3$)phenyl)-7-(1H-pyrazol-4-yl)isoxazolo[4,5-c]pyridin-3-amine,
(6) 4-(4-amino-2-fluoro-5-(methyl sulfonyl)phenyl)-7-(1H-pyrazol-4-yl)isoxazolo[4,5-c]pyridin-3-amine,
(7) 4-(4-amino-5-(ethylthio)-2-fluorophenyl)-7-(1H-pyrazol-4-yl)isoxazolo[4,5-c]pyridin-3-amine,
(8) 4-(4-amino-2-fluoro-5-(methylsulfinyl)phenyl)-7-(1H-pyrazol-4-yl)isoxazolo[4,5-c]pyridin-3-amine,
(9) 4-(4-amino-2-fluoro-3-methoxyphenyl)-7-(1H-pyrazol-4-yl)isoxazolo[4,5-c]pyridin-3-amine,
(10) methyl 2-amino-5-(3-amino-7-(1H-pyrazol-4-yl)isoxazolo[4,5-c]pyridin-4-yl)-4-fluorobenzoate,
(11) 2-amino-5-(3-amino-7-(1H-pyrazol-4-yl)isoxazolo[4,5-c]pyridin-4-yl)-4-fluorobenzoic acid,
(12) 2-amino-5-(3-amino-7-(1H-pyrazol-4-yl)isoxazolo[4,5-c]pyridin-4-yl)-4-fluorobenzamide,
(13) 4-(4-amino-2-fluoro-5-methoxyphenyl)-7-(3-methyl-1H-pyrazol-4-yl)isoxazolo[4,5-c]pyridin-3-amine,
(14) methyl 2-amino-5-(3-amino-7-(1-((phosphonooxy)methyl)-1H-pyrazol-4-yl)isoxazolo[4,5-c]pyridin-4-yl)-4-fluorobenzoate,
(15) 1-(2-amino-5-(3-amino-7-(1H-pyrazol-4-yl)isoxazolo[4,5-c]pyridin-4-yl)-4-fluorophenyl)ethan-1-one,
(16) 4-(4-amino-2-chloro-5-(methylthio)phenyl)-7-(1H-pyrazol-4-yl)isoxazolo[4,5-c]pyridin-3-amine,
(17) ethyl 2-amino-5-(3-amino-7-(1H-pyrazol-4-yl)isoxazolo[4,5-c]pyridin-4-yl)-4-fluorobenzoate,
(18) (4-(4-(5-acetyl-4-amino-2-fluorophenyl)-3-aminoisoxazolo[4,5-c]pyridin-7-yl)-1H-pyrazol-1-yl)methyl dihydrogen phosphate,
(19) ethyl 2-amino-5-(3-amino-7-(1-((phosphonooxy)methyl)-1H-pyrazol-4-yl)isoxazolo[4,5-c]pyridin-4-yl)-4-fluorobenzoate,
(20) 2-amino-5-(3-amino-7-(1H-pyrazol-4-yl)isoxazolo[4,5-c]pyridin-4-yl)-4-fluoro-N-methylbenzamide,
(21) 1-(2-amino-5-(3-amino-7-(1H-pyrazol-4-yl)isoxazolo[4,5-c]pyridin-4-yl)-4-fluorophenyl)propan-1-one,
(22) 2-amino-5-(3-amino-7-(1H-pyrazol-4-yl)isoxazolo[4,5-c]pyridin-4-yl)-N-ethyl-4-fluorobenzamide,
(23) 1-(2-amino-5-(3-amino-7-(1H-pyrazol-4-yl)isoxazolo[4,5-c]pyridin-4-yl)phenyl)ethan-1-one,
(24) methyl 2-amino-5-(3-amino-7-(1H-pyrazol-4-yl)isoxazolo[4,5-c]pyridin-4-yl)benzoate,

(25) 2-amino-5-(3-amino-7-(1H-pyrazol-4-yl)isoxazolo[4,5-c]pyridin-4-yl)-N-propylbenzamide,
(26) 1-(2-amino-5-(3-amino-7-(1H-pyrazol-4-yl)isoxazolo[4,5-c]pyridin-4-yl)-4-fluorophenyl)butan-1-one,
(27) 2-amino-5-(3-amino-7-(1H-pyrazol-4-yl)isoxazolo[4,5-c]pyridin-4-yl)-4-fluoro-N-propylbenzamide,
(28) 1-(2-amino-5-(3-amino-7-(1H-pyrazol-4-yl)isoxazolo[4,5-c]pyridin-4-yl)phenyl)butan-1-one,
(29) 2-hydroxyethyl 2-amino-5-(3-amino-7-(1H-pyrazol-4-yl)isoxazolo[4,5-c]pyridin-4-yl)-4-fluorobenzoate,
(30) 2-amino-5-(3-amino-7-(1H-pyrazol-4-yl)isoxazolo[4,5-c]pyridin-4-yl)benzamide,
(31) 2-amino-5-(3-amino-7-(1H-pyrazol-4-yl)isoxazolo[4,5-c]pyridin-4-yl)-N-methylbenzamide,
(32) (4-(3-amino-4-(4-amino-5-(ethylcarbamoyl)-2-fluorophenyl)isoxazolo[4,5-c]pyridin-7-yl)-1H-pyrazol-1-yl)methyl dihydrogen phosphate,
(33) 1-(2-amino-5-(3-amino-7-(1H-pyrazol-4-yl)isoxazolo[4,5-c]pyridin-4-yl)-4-hydroxyphenyl)ethan-1-one,
(34) 2-amino-5-(3-amino-7-(1H-pyrazol-4-yl)isoxazolo[4,5-c]pyridin-4-yl)-N-ethylbenzamide, (35) 1-(2-amino-5-(3-amino-7-(1H-pyrazol-4-yl)isoxazolo[4,5-c]pyridin-4-yl)phenyl)propan-1-one,
(36) 2-amino-5-(3-amino-7-(1H-pyrazol-4-yl)isoxazolo[4,5-c]pyridin-4-yl)-4-chloro-N-ethylbenzamide,
(37) (4-(3-amino-4-(4-amino-2-fluoro-5-(methylthio)phenyl)isoxazolo[4,5-c]pyridin-7-yl)-1H-pyrazol-1-yl)methyl dihydrogen phosphate,
(38) (4-(3-amino-4-(4-amino-2-fluoro-5-propionylphenyl)isoxazolo[4,5-c]pyridin-7-yl)-1H-pyrazol-1-yl)methyl dihydrogen phosphate,
(39) (4-(4-(3-acetyl-4-aminophenyl)-3-aminoisoxazolo[4,5-c]pyridin-7-yl)-1H-pyrazol-1-yl)methyl dihydrogen phosphate,
(40) 4-(2-fluoro-5-methoxy-4-nitrophenyl)-7-(1H-pyrazol-4-yl)isoxazolo[4,5-c]pyridin-3-amine,
(41) (4-(3-amino-4-(4-amino-2-fluoro-5-(methylsulfonyl)phenyl)isoxazolo[4,5-c]pyridin-7-yl)-1H-pyrazol-1-yl)methyl dihydrogen phosphate,
(42) (4-(3-amino-4-(4-amino-5-(ethyl carbamoyl)-2-chlorophenyl)isoxazolo[4,5-c]pyridin-7-yl)-1H-pyrazol-1-yl)methyl dihydrogen phosphate, (43) 1-(2-amino-5-(3-amino-7-(1H-pyrazol-4-yl)isothiazolo[4,5-c]pyridin-4-yl)-4-fluorophenyl)ethan-1-one, and
(44) 4-(4-amino-2-fluoro-5-(trifluoromethyl)phenyl)-7-(1H-pyrazol-4-yl)isoxazolo[4,5-c]pyridin-3-amine;
[1-34] the compound, N-oxide thereof, pharmaceutically acceptable salt thereof or solvate thereof, according to the preceding item [1-1], wherein the compound represented by the general formula (I-1) is the compound selected from the group consisting of:
(1) methyl 2-amino-5-(3-amino-7-(1-((phosphonooxy)methyl)-1H-pyrazol-4-yl)isoxazolo[4,5-c]pyridin-4-yl)-4-fluorobenzoate,
(2) (4-(4-(5-acetyl-4-amino-2-fluorophenyl)-3-aminoisoxazolo[4,5-c]pyridin-7-yl)-1H-pyrazol-1-yl)methyl dihydrogen phosphate,
(3) ethyl 2-amino-5-(3-amino-7-(1-((phosphonooxy)methyl)-1H-pyrazol-4-yl)isoxazolo[4,5-c]pyridin-4-yl)-4-fluorobenzoate,
(4) (4-(3-amino-4-(4-amino-5-(ethyl carbamoyl)-2-fluorophenyl)isoxazolo[4,5-c]pyridin-7-yl)-1H-pyrazol-1-yl)methyl dihydrogen phosphate,
(5) (4-(3-amino-4-(4-amino-2-fluoro-5-(methylthio)phenyl)isoxazolo[4,5-c]pyridin-7-yl)-1H-pyrazol-1-yl)methyl dihydrogen phosphate,
(6) (4-(3-amino-4-(4-amino-2-fluoro-5-propionylphenyl)isoxazolo[4,5-c]pyridin-7-yl)-1H-pyrazol-1-yl)methyl dihydrogen phosphate,
(7) (4-(4-(3-acetyl-4-aminophenyl)-3-aminoisoxazolo[4,5-c]pyridin-7-yl)-1H-pyrazol-1-yl)methyl dihydrogen phosphate,
(8) (4-(3-amino-4-(4-amino-2-fluoro-5-(methylsulfonyl)phenyl)isoxazolo[4,5-c]pyridin-7-yl)-1H-pyrazol-1-yl)methyl dihydrogen phosphate, and
(9) (4-(3-amino-4-(4-amino-5-(ethyl carbamoyl)-2-chlorophenyl)isoxazolo[4,5-c]pyridin-7-yl)-1H-pyrazol-1-yl)methyl dihydrogen phosphate;
[1-35] the pharmaceutically acceptable salt of the compound or the solvate thereof, according to any one of the preceding items [1-1] to [1-34], wherein the pharmaceutically acceptable salt of the compound described in any one of the preceding items [1-1] to [1-34] is an alkali metal salt (e.g., a lithium salt, sodium salt or potassium salt);
[1-36] the solvate of the compound or the pharmaceutically acceptable salt thereof, according to any one of the preceding items [1-1] to [1-35], wherein the solvate of the compound or the pharmaceutically acceptable salt thereof described in any one of the preceding items [1-1] to [1-35] is a hydrate;
[2-1] a pharmaceutical composition containing the compound represented by the general formula (I), general formula (II) or general formula (III), an N-oxide thereof, a prodrug thereof, a pharmaceutically acceptable salt thereof or a solvate thereof and a pharmaceutically acceptable carrier;
[2-2] a pharmaceutical composition containing the compound represented by the general formula (I-1), general formula (II-1) or general formula (III-1), an N-oxide thereof, a pharmaceutically acceptable salt thereof or a solvate thereof and a pharmaceutically acceptable carrier;
[2-3] the pharmaceutical composition according to the preceding item [2-1] or [2-2], further containing one or more kinds of other anti-cancer drugs as an active ingredient;
[3-1] an agent for suppressing the progression of, suppressing the recurrence of and/or treating cancer or infectious disease, containing the compound represented by the general formula (I), general formula (II) or general formula (III), an N-oxide thereof, a prodrug thereof, a pharmaceutically acceptable salt thereof or a solvate thereof as an active ingredient;
[3-2] an agent for suppressing the progression of, suppressing the recurrence of and/or treating cancer or infectious disease, containing the compound represented by the general formula (I-1), general formula (II-1) or general formula (III-1), an N-oxide thereof, a pharmaceutically acceptable salt thereof or a solvate thereof as an active ingredient;
[3-3] the agent according to the preceding item [3-1] or [3-2], wherein the cancer is solid cancer or blood cancer;
[3-4] the agent according to the preceding item [3-3], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell cancer (e.g., clear cell renal cell cancer), breast cancer, ovarian cancer (e.g., serous ovarian cancer and ovarian clear cell adenocarcinoma), nasopharyngeal cancer, uterine cancer (e.g., cervical cancer and endometrial cancer), anal cancer (e.g., anal canal cancer), colorectal cancer (e.g., high-frequency microsatellite instability (hereinafter, abbreviated as "MSI-H") and/or defective mismatch repair (hereinafter, abbreviated as "dMMR") positive colorectal cancer), rectal cancer, colon cancer, hepatocellular carcinoma, esophageal cancer, gastric cancer, esophagogastric junction cancer, pancreatic cancer, urine urothelial cancer (e.g., bladder cancer, upper urinary tract cancer, ureteral cancer, renal pelvis cancer and urethral cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine system cancer, thyroid cancer, parathyroid cancer, adrenal carcinoma, spinal tumor, neuroblastoma, medulloblastoma, ocular retinoblastoma, neuroendocrine tumor, brain tumor (e.g., glioma (e.g., glioblastoma and gliosarcoma) and meningioma) and squamous cell carcinoma;

[3-5] the agent according to the preceding item [3-3], wherein the solid cancer is bone/soft tissue sarcoma (e.g., Ewing sarcoma, pediatric rhabdomyosarcoma, endometrial leiomyosarcoma, chondrosarcoma, lung sarcoma, osteosarcoma and congenital fibrosarcoma) or Kaposi's sarcoma;

[3-6] the agent according to the preceding item [3-3], wherein the blood cancer is one or more cancers selected from multiple myeloma, malignant lymphoma (e.g., non-Hodgkin lymphoma (e.g., follicular lymphoma, precursor B-cell lymphoblastic lymphoma, chronic B lymphocytic leukemia, nodal marginal zone B-cell lymphoma, diffuse large B-cell lymphoma, MALT lymphoma, splenic primary marginal zone B-cell lymphoma, hairy cell leukemia, primary mediastinal large B-cell lymphoma, Burkitt lymphoma, mantle cell lymphoma, mycosis fungoides, Sezary syndrome, chronic or acute lymphocytic leukemia, precursor T-cell lymphoblastic lymphoma, chronic T lymphocytic leukemia, large granular T cell leukemia, large granular NK cell leukemia, peripheral T-cell lymphoma, extranodal NK/T-cell lymphoma, adult T-cell leukemia, angiocentric lymphoma, intestinal T-cell lymphoma, Hodgkin-like/Hodgkin-related anaplastic large cell lymphoma, B-cell lymphoblastic leukemia, T-cell lymphoblastic leukemia and lymphoplasmacytoid lymphoma) and Hodgkin lymphoma (e.g., classic Hodgkin lymphoma and nodular lymphoid predominant Hodgkin lymphoma)), leukemia (e.g., acute myelogenous leukemia and chronic myelogenous leukemia), central nervous system malignant lymphoma, myelodysplastic syndromes and myeloproliferative syndromes;

[3-7] the agent according to the preceding item [3-1] or [3-2], wherein the cancer is pediatric cancer or unknown primary cancer;

[3-8] the agent according to any one of the preceding items [3-1] to [3-7], wherein the cancer is the cancer on which the therapeutic effects of other anti-cancer drugs are insufficient or not sufficient;

[3-9] the agent according to any one of the preceding items [3-1] to [3-8], wherein the cancer is worsened after treatment with other anti-cancer drugs;

[3-10] the agent according to any one of the preceding items [3-1] to [3-7], wherein a patient with cancer has not been treated with other anti-cancer drugs;

[3-11] the agent according to any one of the preceding items [3-1] to [3-10], which is prescribed in postoperative adjuvant therapy or preoperative adjuvant therapy;

[3-12] the agent according to any one of the preceding items [3-1] to [3-11], wherein the cancer is incurable or unresectable, metastatic, recurrent, refractory and/or distant metastatic;

[3-13] the agent according to any one of the preceding items [3-1] to [3-12], wherein the ratio of PD-L1-expressing tumor cells among tumor cells in tumor tissue (hereinafter, abbreviated as "TPS") or the numerical value obtained by dividing the number of PD-L1 positive cells (tumor cells, lymphocytes and macrophages) by the total number of tumor cells and multiplying by 100 (hereinafter, abbreviated as "CPS") is 50% or more, 25% or more, 10% or more, 5% or more, or 1% or more;

[3-14] the agent according to any one of the preceding items [3-1] to [3-12], wherein TPS is less than 50%, less than 25%, less than 10%, less than 5% or less than 1%;

[3-15] the agent according to any one of the preceding items [3-1] to [3-14], wherein the cancer has MSI-H and/or dMMR;

[3-16] the agent according to any one of the preceding items [3-1] to [3-14], wherein the cancer does not have MSI-H and/or dMMR, or has low frequency microsatellite instability (hereinafter, abbreviated as "MSI-L");

[3-17] the agent according to any one of the preceding items [3-4] to [3-16], wherein malignant melanoma or non-small cell lung cancer is BRAF V600E mutation-positive;

[3-18] the agent according to any one of the preceding items [3-4] to [3-16], wherein malignant melanoma or non-small cell lung cancer is BRAF V600E wild-type;

[3-19] the agent according to any one of the preceding items [3-4] to [3-18], wherein non-small cell lung cancer is EGFR gene mutation positive and/or ALK fusion gene positive;

[3-20] the agent according to any one of the preceding items [3-4] to [3-18], wherein non-small cell lung cancer is EGFR gene mutation negative and/or ALK fusion gene negative;

[3-21] the agent according to any one of the preceding items [3-1] to [3-20], wherein tumor mutation burden (hereinafter, abbreviated as "TMB".) of the cancer is high frequency (10 mutations or more per $10^6$ bases);

[3-22] the agent according to any one of the preceding items [3-1] to [3-20], wherein TMB of the cancer is low frequency (less than 10 mutations per $10^6$ bases);

[3-23] the agent according to any one of the preceding items [3-1] to [3-22], which is characterized by further being administered in combination with one or more kinds of other anti-cancer drugs;

[4-1] the agent according to the preceding item [3-1] or [3-2], wherein the infectious disease is a condition caused by viral infection, parasitic infection, bacterial infection or fungal infection;

[4-2] the agent according to the preceding item [4-1], wherein the virus infection disease is the infection disease caused by adenovirus, arenavirus, bunyavirus, calicivirus, coronavirus, Filovirus, hepadnavirus, herpesvirus, orthomyxovirus, papovavirus, paramyxovirus, parvovirus, picomavirus, poxvirus, reovirus, retrovirus, rhabdovirus, togavirus, papillomavirus (e.g., human papillomavirus (HPV)), human immunodeficiency virus (HIV), poliovirus, hepatitis virus (e.g., hepatitis A virus (HAV), hepatitis B virus (HBV), hepatitis C virus (HCV), hepatitis D virus (HDV) and hepatitis E virus (HEV)), smallpox virus (e.g., variola major and variola minor), vaccinia virus, influenza virus, rhinovirus, dengue virus, equine encephalitis virus, rubella virus, yellow fever virus, Norwalk virus, human T-cell leukemia virus (HTLV-I), hairy cell leukemia virus (HTLV-II), California encephalitis virus, hanta virus (hemorrhagic fever), rabies virus, Ebola virus, Marburg virus, measles virus, mumps virus, respiratory syncytial virus (RSV), herpes simplex type 1 (oral herpes), herpes simplex type 2 (genital herpes), herpes zoster (varicella-zoster virus), cytomegalovirus (CMV), Epstein-Barr virus (EBV), flavivirus, foot-and-mouth disease virus, Chikungunya virus, Lassa virus, arenavirus or oncovirus;

[5-1] a method for suppressing the progression of, suppressing the recurrence of and/or treating cancer or infectious disease, comprising administering an effective dose of the compound represented by the general formula (I), an N-oxide thereof, a prodrug thereof, a pharmaceutically acceptable salt thereof or a solvate thereof to a patient in need thereof;

[5-2] a method for suppressing the progression of, suppressing the recurrence of and/or treating cancer or infectious disease, comprising administering an effective dose of the compound represented by the general formula (I-1), an N-oxide thereof, a pharmaceutically acceptable salt thereof or a solvate thereof to a patient in need thereof;

[6-1] a compound represented by the general formula (I), an N-oxide thereof, a prodrug thereof, a pharmaceutically acceptable salt thereof or a solvate thereof for use in suppressing the progression of, suppressing the recurrence of and/or treating cancer or infectious disease;

[6-2] a compound represented by the general formula (I-1), an N-oxide thereof, a pharmaceutically acceptable salt thereof or a solvate thereof for use in suppressing the progression of, suppressing the recurrence of and/or treating cancer or infectious disease;

[7-1] use of a compound represented by the general formula (I), an N-oxide thereof, a prodrug thereof, a pharmaceutically acceptable salt thereof or a solvate thereof in manufacturing a drug for suppressing the progression of, suppressing the recurrence of and/or treating cancer or infectious disease;

[7-2] use of a compound represented by the general formula (I-1), an N-oxide thereof, a pharmaceutically acceptable salt thereof or a solvate thereof in manufacturing a drug for suppressing the progression of, suppressing the recurrence of and/or treating cancer or infectious disease;

[8-1] the pharmaceutical composition according to the preceding item [2-3] or the agent according to any one of the preceding items [3-8] to [3-10] and [3-23], wherein the other anti-cancer drugs described in the preceding item [2-3], [3-8] to [3-10] or [3-23] are one or more kinds of agents selected from an alkylating agent, platinum preparation, antimetabolite (e.g., antifolate, pyridine metabolism inhibitor and purine metabolism inhibitor), ribonucleotide reductase inhibitor, nucleotide analog, topoisomerase inhibitor, microtubule polymerization inhibitor, microtubule depolymerization inhibitor, antitumor antibiotic, cytokine preparation and anti-hormonal drug;

[8-2] the pharmaceutical composition according to the preceding item [2-3] or the agent according to any one of the preceding items [3-8] to [3-10] and [3-23], wherein the other anti-cancer drug described in the preceding item [2-3], [3-8] to [3-10] or [3-23] is a molecular targeting drug;

[8-3] the pharmaceutical composition according to the preceding item [8-2] or the agent according to the preceding item [8-2], wherein the molecular targeting drug is one or more kinds of agents selected from an ALK inhibitor, BCR-ABL inhibitor, EGFR inhibitor, B-Raf inhibitor, VEGFR inhibitor, FGFR inhibitor, c-Met inhibitor, Axl inhibitor, Mek inhibitor, CDK inhibitor, Btk inhibitor, PI3K-δ/γ inhibitor, JAK-1/2 inhibitor, TGFbR1 inhibitor, Cancer cell sternness kinase inhibitor, Syk/FLT3 dual inhibitor, ATR inhibitor, Wee1 kinase Inhibitor, multi-tyrosine kinase inhibitor, mTOR inhibitor, HDAC inhibitor, PARP inhibitor, aromatase inhibitor, EZH2 inhibitor, galectin-3 inhibitor, STAT3 inhibitor, DNMT inhibitor, SMO inhibitor, Hsp90 inhibitor, γ-tubulin specific inhibitor, HIF2α inhibitor, glutaminase inhibitor, E3 ligase inhibitor, Nrf2 activator, arginase inhibitor, cell cycle inhibitor, IAP antagonist, anti-Her2 antibody, anti-EGFR antibody, anti-VEGF antibody, anti-VEGFR2 antibody, anti-CD20 antibody, anti-CD30 antibody, anti-CD38 antibody, anti-DR5 antibody, anti-CA125 antibody, anti-DLL4 antibody, anti-fucosyl GM1 antibody, anti-gpNMB antibody, anti-Mesothelin antibody, anti-MMP9 antibody, anti-GD2 antibody, anti-c-Met antibody, anti-FOLR1 antibody, anti-Ang2-VEGF bispecific antibody, anti-CD30-CD16A bispecific antibody, anti-CD79b antibody, anti-FAP antibody/IL-2 fusion protein, anti-CEA antibody/IL-2 fusion protein, anti-CEA-CD3 bispecific antibody, anti-DLL3 antibody, anti-CD3-CD19 bispecific antibody and anti-CD20-CD3 bispecific antibody;

[8-4] the pharmaceutical composition according to the preceding item [2-3] or the agent according to any one of the preceding items [3-8] to [3-10] and [3-23], wherein the other anti-cancer drug described in the preceding item [2-3], [3-8] to [3-10] or [3-23] is a cancer immunotherapeutic drug;

[8-5] the pharmaceutical composition according to the preceding item [8-4] or the agent according to the preceding item [8-4], wherein the cancer immunotherapeutic drug is one or more kinds of agents selected from an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-MR antibody, anti-BTLA antibody, anti-TIGIT antibody, anti-VISTA antibody, anti-CD137 antibody, anti-CSF-1R antibody/CSF-1R inhibitor, anti-OX40 antibody, anti-HVEM antibody, anti-CD27 antibody, anti-GITR antibody, anti-CD28 antibody, anti-CCR4 antibody, anti-B7-H3 antibody, anti-ICOS agonistic antibody, anti-CD4 antibody, anti-DEC-205 antibody/NY-ESO-1 fusion protein, anti-SLAMF7 antibody, anti-CD73 antibody, anti-CD122 antibody, anti-CD40 agonistic antibody, IDO inhibitor, TLR agonist, Adenosine A2A receptor antagonist, anti-NKG2A antibody, anti-CSF-1 antibody, immunopotentiator, IL-15 super agonist, soluble LAG3, CD47 antagonist and IL-12 antagonist;

[8-6] the pharmaceutical composition according to the preceding item [8-5] or the agent according to the preceding item [8-5], wherein the anti-PD-1 antibody is the antibody selected from Nivolumab, Cemiplimab, Pembrolizumab, Spartalizumab, Tislelizumab, AMP-514, Dostarlimab, Toripalimab, Camrelizumab, Genolimzumab, Sintilimab, STI-A1110, ENUM 388D4, ENUM 244C8, GLS010, MGA012, AGEN2034, CS1003, HLX10, BAT-1306, AK105, AK103, BI 754091, LZMO09, CMAB819, Sym021, GB226, SSI-361, JY034, HX008, ABBV181, BCD-100, ISU106, PF-06801591, CX-188, JNJ-63723283 and AB122;

[8-7] the pharmaceutical composition according to the preceding item [8-5] or the agent according to the preceding item [8-5], wherein the anti-PD-L1 antibody is the antibody selected from Atezolizumab, Avelumab, Durvalumab, BMS-936559, STI-1014, KNO35, LY3300054, HLX20, SHR-1316, CS1001, MSB2311, BGB-A333, KL-A167, CK-301, AK106, AK104, ZKAB001, FAZ053, CBT-502, JS003 and CX-072;

[9-1] a STING agonistic agent containing the compound represented by the general formula (I), general formula (II) or general formula (III), an N-oxide thereof, a prodrug thereof, a pharmaceutically acceptable salt thereof or a solvate thereof as an active ingredient;

[9-2] a STING agonistic agent containing the compound represented by the general formula (I-1), general formula (II-1) or general formula (III-1), an N-oxide thereof, a pharmaceutically acceptable salt thereof or a solvate thereof as an active ingredient;

[10-1] an IFN-β production inducer containing the compound represented by the general formula (I), general formula (II) or general formula (III), an N-oxide thereof, a prodrug thereof, a pharmaceutically acceptable salt thereof or a solvate thereof as an active ingredient; and

[10-2] an IFN-β production inducer containing the compound represented by the general formula (I-1), general formula (II-1) or general formula (III-1), an N-oxide thereof, a pharmaceutically acceptable salt thereof or a solvate thereof as an active ingredient.

Advantage Effects of Invention

Since the compound of the present invention has the agonistic activity to STING, it can be used as an active ingredient of the agent for suppressing the progression of, suppressing the recurrence of and/or treating cancer or infectious disease.

DESCRIPTION OF EMBODIMENTS

Figure 1:
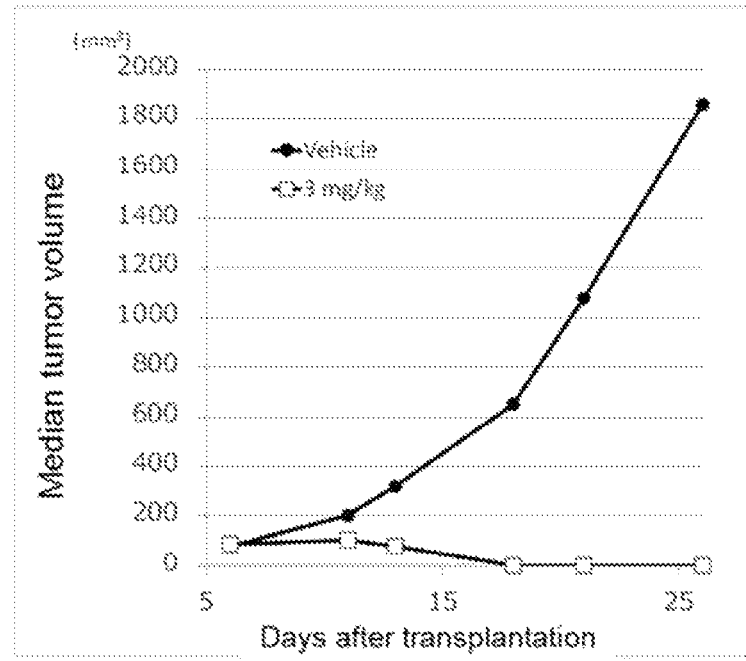
FIG. 1 It shows the antitumor activity of the compound of the present invention (the compound shown in Example 1) in a subcutaneous tumor model bearing mouse colon cancer cell line MC38. A vehicle and the compound of the present invention (n=6) were administered 7 days after the MC38 transplantation, respectively, and the change in tumor volume was continuously measured until 26 days after the transplantation.

In the present specification, examples of the "halogen atom" include a fluorine atom, chlorine atom, bromine atom and iodine atom.

In the present specification, examples of the "C1-4 alkyl group" include a methyl group, ethyl group, n-propyl group, isopropyl group, n-butyl group, isobutyl group, sec-butyl group and tert-butyl group.

In the present specification, examples of the "C1-5 alkyl group" include a methyl group, ethyl group, n-propyl group, isopropyl group, n-butyl group, isobutyl group, sec-butyl group, tert-butyl group, pentyl group, isopentyl group and 2,3-dimethylpropyl group.

In the present specification, the "C1-3 alkylene group" is a methylene group, ethylene group or propylene group.

In the present specification, examples of the "C1-4 alkoxy group" include a methoxy group, ethoxy group, n-propoxy group, isopropoxy group, n-butoxy group, isobutoxy group, sec-butoxy group and tert-butoxy group.

In the present specification, examples of the "C1-4 haloalkyl group" include a fluoromethyl group, chloromethyl group, bromomethyl group, iodomethyl group, difluoromethyl group, trifluoromethyl group, 1-fluoroethyl group, 2-fluoroethyl group, 2-chloroethyl group, pentafluoroethyl group, 1-fluoropropyl group, 2-chloropropyl group, 3-fluoropropyl group, 3-chloropropyl group, 4,4,4-trifluorobutyl group and 4-bromobutyl and the like.

In the present specification, examples of the "C1-4 haloalkoxy group" include a trifluoromethoxy group, trichloromethoxy group, chloromethoxy group, bromomethoxy group, fluoromethoxy group, iodomethoxy group, difluoromethoxy group, dibromomethoxy group, 2-chloroethoxy group, 2,2,2-trifluoroethoxy group, 2,2,2-trichloroethoxy group, 3-bromopropoxy group, 3-chloropropoxy group, 2,3-dichloropropoxy group and the like.

In the present specification, examples of the "C3-6 cycloalkyl group" include a cyclopropyl group, cyclobutyl group, cyclopentyl group and cyclohexyl group.

In the present specification, examples of the "C3-7 cycloalkyl group" include a cyclopropyl group, cyclobutyl group, cyclopentyl group, cyclohexyl group and cycloheptyl group.

In the present specification, examples of the "C3-7 cycloalkylene group" include a cyclopropylene group, cyclobutylene group, cyclopentylene group, cyclohexylene group and cycloheptylene group.

In the present specification, examples of the "C1-4 alkoxycarbonyl group" include a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, and tert-butoxycarbonyl group.

In the present specification, examples of the "C5-6 monocyclic carbocycle" include a cyclopentane, cyclohexane, cyclopentene, cyclohexene, cyclopentadiene, cyclohexadiene, benzene and the like.

In the present specification, examples of the "5 to 7-membered monocycle" include a cyclopentane, cyclohexane, cyclopentene, cyclohexene, cyclopentadiene, cyclohexadiene, benzene, cycloheptane, cycloheptene, cycloheptadiene, pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, oxolane, dioxolane, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxothiane, dioxothiane, oxathiane, dioxane, thiopyran, dihydrothiopyran, tetrahydrothiopyran, dithiane, azepine, diazepine, oxepin, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepin, tetrahydrooxepin, perhydrooxepin, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the present specification, examples of the "8 to 10-membered bicycle" include a pentalene, perhydropentalene, indene, perhydroindene, indane, azulene, perhydroazulene, naphthalene, dihydronaphthalene, tetrahydronaphthalene, perhydronaphthalene, thienopyrazole, thienoimidazole, pyrazolothiazole, indole, isoindole, indolizine, benzofuran, isobenzofuran, benzothiophene, isobenzothiophene, indazole, purine, benzoxazole, benzothiazole, benzimidazole, imidazopyridine, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzoimidazole, perhydrobenzoimidazole, dioxaindane, benzodithiolane, dithianaphthalene, quinoline, isoquinoline, quinolidine, phthalazine, pteridine, naphthyridine, quinoxaline, quinazoline, cinnoline, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzoxazine, dihydrobenzothiazine, pyrazinomorpholine, benzodioxane, chroman, benzodithiane and the like.

In the present specification, examples of the "5 to 6-membered monocyclic heterocycle containing 1 to 4 heteroatoms selected from an oxygen atom, nitrogen atom and sulfur atom" include a pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, oxolane, dioxolane, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxothiane, dioxothiane, oxathiane, dioxane, thiopyran, dihydrothiopyran, tetrahydrothiopyran, dithiane and the like.

In the present specification, examples of the "5 to 6-membered monocyclic aromatic heterocycle containing 1 to 4 heteroatoms selected from an oxygen atom, nitrogen atom and sulfur atom" include a pyrrole, imidazole, triazole, tetrazole, pyrazole, furan, thiophene, oxazole, isoxazole, thiazole, isothiazole, furazan, oxadiazole, thiadiazole, pyridine, pyrazine, pyrimidine, pyridazine and the like.

In the present specification, examples of the "5 to 6-membered monocyclic aromatic nitrogen-containing heterocycle containing 1 to 4 nitrogen atoms and without any other heteroatoms" include a pyrrole, imidazole, triazole, tetrazole, pyrazole, pyridine, pyrazine, pyrimidine, pyridazine and the like.

In the present specification, examples of the "3 to 7-membered monocyclic non-aromatic heterocycle" include an oxirane, aziridine, thiirane, azetidine, oxetane, thietane, pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrothiadiazole, tetrahydrothiadiazole, oxolane, dioxolane, dithiolane, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxothiane, dioxothiane, oxathiane, dioxane, dithiane, azepine, diazepine, oxepin, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepin, tetrahydrooxepin, perhydrooxepin, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the specification of the present invention, examples of the "free radical group producing a compound represented by the general formula (I), N-oxide thereof, pharmaceutically acceptable salt thereof or solvate thereof, as a result of decomposition in vivo" include the group defined as $R^{FR}$.

Ring A in the general formula (I), (I-1), (II) or (II-1) of the present invention is preferably a 5 to 6-membered monocyclic aromatic heterocycle containing 1 to 4 heteroatoms selected from an oxygen atom, nitrogen atom and sulfur atom, more preferably pyrazole, triazole (e.g., 1,2,3-triazole and 1,2,4-triazole), tetrazole, oxazole, isoxazole, imidazole, thiazole or isothiazole, and furthermore preferably, pyrazole, while Ring B of the general formula (I) or (I-1) of the present invention is preferably (i) a C5-6 monocyclic carbocycle or (ii) a 5 to 6-membered monocyclic heterocycle containing 1 to 4 heteroatoms selected from an oxygen atom, nitrogen atom and sulfur atom, and more preferably benzene.

Further, Z in the general formula (I) or (I-1) of the present invention is preferably an oxygen atom, Y is preferably —CH═, and X is preferably a nitrogen atom.

$L^2$ in the general formula (I) or the like, the formula (Ib), the general formula (I-1) or the like or the formula (Ib-1) of the present invention is preferably a bond or C1-3 alkylene group, and more preferably, a bond, and $L^1$ is preferably —O—, —CONH—, —CO—, —CO$_2$—, —S—, —SO$_2$— or —SO—, and more preferably —CONH— (provided that the left side of the group is bond to the Ring B), —CO—, —CO$_2$—, —S—, —SO$_2$— or —SO—, $R^1$ is preferably a hydrogen atom, hydroxyl group, C1-4 alkyl group or carboxy group, more preferably a hydrogen atom or C1-4 alkyl group, and furthermore preferably a hydrogen atom, methyl group, ethyl group or n-propyl group, $R^2$ and $R^{2c}$ are preferably a nitro group and $NR^{2a}R^{2b}$ and $NR^{2d}R^{2e}$, respectively, more preferably an amino group, and $R^3$ is preferably a hydrogen atom, halogen atom or hydroxyl group, and more preferably a halogen atom.

In the general formula (I) or the like, the formula (Ib), the general formula (I-1) or the like or the formula (Ib-1) of the present invention, m is preferably 1 and p and pa are preferably zero or 1, and more preferably zero. In the formula (Ib) or (Ib-1) or the general formula (II), (II-1), (III) or (III-1) of the present invention, n is preferably 2 or 1.

$R^{2a}$, $R^4$ and $R^6$ in the general formula (I) or the like of the present invention are preferably hydrogen atoms, and $R^{2d}$, $R^{4a}$ and $R^{6a}$ in the general formula (I-1) or the like are preferably hydrogen atoms or phosphonooxyalkyl group, and the phosphonooxyalkyl group is preferably —CH$_2$OP(═O)(OH)$_2$, —CHCH$_3$OP(═O)(OH)$_2$ or CH$_2$OP(═O)(OH)(OCH$_2$OCO$_2$CH(CH$_3$)$_2$), and more preferably —CH$_2$OP(═O)(OH)$_2$. However, two or more of $R^{2d}$, $R^{4a}$ and $R^{6a}$ do not represent the phosphonooxyalkyl groups, simultaneously.

W in the formula (Ib), formula (Ib-1), general formula (II), general formula (II-1), general formula (III) or general formula (III-1) of the present invention is preferably —CH═ and V is preferably —CH═.

U in the formula (Ib), formula (Ib-1), general formula (II) or general formula (II-1) of the present invention is preferably a carbon atom.

T in the general formula (I), (I-1), (II) or (II-1) of the present invention is preferably a nitrogen atom.

The compound represented by the general formula (I) of the present invention, N-oxide thereof, prodrug thereof, pharmaceutically acceptable salt thereof or solvate thereof is preferably a compound represented by the general formula (II), N-oxide thereof, prodrug thereof, pharmaceutically acceptable salt thereof, or solvate thereof, more preferably a compound represented by the general formula (III), N-oxide thereof, prodrug thereof, pharmaceutically acceptable salt thereof or solvate thereof.

Furthermore, the compounds represented by the general formula (I), N-oxides thereof, prodrugs thereof, pharmaceutically acceptable salts thereof, or solvates thereof are preferable, for example, the compounds (1) to (35) described in the preceding item [26], N-oxides thereof, prodrugs thereof, pharmaceutically acceptable salts thereof, or solvates thereof.

In addition, the compound represented by the general formula (I-1) of the present invention, N-oxide thereof, pharmaceutically acceptable salt thereof or solvate thereof is preferably the compound represented by the general formula (II-1), N-oxide thereof, pharmaceutically acceptable salt thereof or solvate thereof, more preferably a compound represented by the general formula (III-1), N-oxide thereof, pharmaceutically acceptable salt thereof or solvate thereof.

Furthermore, the compounds represented by the general formula (I-1), N-oxides thereof, pharmaceutically acceptable salts thereof, or solvates thereof are preferably, for example, the compounds of (1) to (44) described in the preceding item [1-33], N-oxides thereof, pharmaceutically acceptable salts thereof, or solvates thereof. Further, the solvates of the compounds described in the preceding item [1-33] are preferably hydrates of the compounds of (1) to (44) described in the preceding item [1-33] or pharmaceutically acceptable salts thereof (e.g., alkali metal salts (e.g., lithium salt, sodium salt and potassium salt, etc.)).

[Isomers]

Unless otherwise specified in the present invention, examples of isomers include all of them. For example, alkyl groups include straight and branched ones. Further, geometric isomers (E-form, Z-form, cis-form, trans-form) in double bonds, rings and condensed rings, optical isomers due to the presence of an asymmetric carbon atom and the like (R, S-form, α, β configuration, enantiomers, diastereomers), optically active substances having optical activity (D, L, d, l isomers), polar substances (high polar substances, low polar substances) by chromatographic separation, equilibrium compounds, rotamers, and these mixtures in any proportion, racemic mixtures, are all included in the present invention. In addition, the present invention also includes all isomers due to tautomers.

Further, the optical isomers in the present invention are not limited to 100% pure ones, and may contain less than 50% other optical isomers.

In the present invention, unless otherwise specified, as being apparent to those skilled in the art, the symbols: ╱ represents that it is connected to the other side of the paper (that is, α arrangement), ╱ represents that it is connected to the front side of the paper (that is, β arrangement), ∕ represents that it is α-configuration, β-configuration or a mixture thereof in any ratio, and ══════ represents a single bond or double bond.

[N-Oxide Forms]

The compound represented by the general formula (I) or the like or the general formula (I-1) or the like can be converted into an N-oxide form thereof by a known method. The N-oxide form means a compound represented by the general formula (I) or the like or the general formula (I-1) or the like in which the nitrogen atom isoxidized. Further, these N-oxide forms can become prodrugs thereof, pharmaceutically acceptable salts thereof or solvates thereof, as described in the item [Prodrugs] below, item [Salts] below and item [Solvates] below.

[Prodrugs]

The compound represented by the general formula (I) or the like or N-oxide thereof can be converted into a prodrug thereof by a known method. The prodrug is a compound which is converted into, for example, the compound represented by the general formula (I) or the like or N-oxide form thereof by a reaction with enzymes or gastric acid or the like in vivo. For example, the compound represented by the general formula (I-1) or the like or N-oxide thereof in which any one of Red, $R^{4a}$ and $R^{6a}$ is the preceding $R^{FR}$ can be administered as a prodrug of the compound represented by the general formula (I) or the like or N-oxide form thereof, and the prodrugs are preferably, for example, the compounds in items (14), (18), (19), (32), (37) to (39), (41) and (42) described in the preceding item [1-33]. The prodrugs of the compounds represented by the general formula (I) or N-oxide form thereof may be changed to the corresponding compound represented by the general formula (I) or the like or N-oxide thereof under physiological conditions as described in Hirokawa Shoten, 1990, "Development of Pharmaceuticals", Volume 7, "Molecular Design," pages 163-198.

Examples of other prodrugs of the compound represented by the general formula (I) or the like or N-oxide form thereof include, in the case that the compound represented by the general formula (I) or the like or N-oxide form thereof has a 5 to 6-membered monocyclic aromatic nitrogen-containing heterocycle containing 1 to 4 nitrogen atoms and no other heteroatom, the compounds in which a nitrogen atom on the nitrogen-containing heterocycle is acylated, alkylated or phosphorylated (e.g., a compound in which the nitrogen atom on the nitrogen-containing heterocycle in the compound represented by the general formula (I) or the like is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated or tert-butylated etc.), in the case that the compound represented by the general formula (I) or the like has an amino group, the compounds in which the amino group is acylated, alkylated or phosphorylated (e.g., the compound in which the amino group in the compound represented by the general formula (I) or the like is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated or tert-butylated, etc.), in the case that the compound represented by the general formula (I) or the like has a hydroxyl group, the compounds in which the hydroxyl group is acylated, alkylated, phosphorylated or borated (e.g., the compound in which the hydroxyl group in the compound represented by the general formula (I) or the like is acetylated, palmitoylated, propanoylated, pivaloylated, succinylated, fumarylated, alanylated or dimethylaminomethylcarbonylated, etc.), and in the case that the compound represented by the general formula (I) or the like has a carboxy group, the compounds in which the carboxy group is esterified or amidated (e.g., the compound in which the carboxy group of the compound represented by the general formula (I) or the like is ethylesterified, phenylesterified, carboxymethylesterified, dimethylaminomethylesterified, pivaloyloxymethylesterified, 1-{(ethoxycarbonyl)oxy}ethylesterified, phthalidylesterified, (5-methyl-2-oxo-1,3-dioxolen-4-yl)methylesterified, 1-{[(cyclohexyloxy)carbonyl]oxy}ethylesterified or methylamidated etc.) and the like. These compounds per se can be produced by a method known. In addition, the prodrug of the compound represented by the general formula (I) or the like or N-oxide form thereof may become a pharmaceutically acceptable salt thereof or solvate thereof, as described in the item [Salts] below and item [Solvate] below.

[Salts]

The compound represented by the general formula (I) or the like, N-oxide thereof or prodrug thereof and the compound represented by the general formula (I-1) or the like or N-oxide thereof can be converted into the corresponding acceptable salt by a known method. Herein, examples of the pharmaceutically acceptable salts include an alkali metal salt (e.g., lithium salt, sodium salt and potassium salt, etc.), alkaline earth metal salt (e.g., calcium salt, magnesium salt and barium salt, etc.), ammonium salt, organic amine salt (e.g., aliphatic amine salt (e.g., methylamine salt, dimethylamine salt, cyclopentylamine salt, trimethylamine salt, triethylamine salt, dicyclohexylamine salt, monoethanolamine salt, diethanolamine salt, triethanolamine salt, procaine salt, meglumine salt, tris(hydroxymethyl)aminomethane salt, and ethylenediamine salt, etc.), aralkylamine salt (e.g., benzylamine salt, phenethylamine salt, N N-dibenzylethylenediamine salt and benetamine salt, etc.), heterocyclic aromatic amine salt (e.g., piperidine salt, pyridine salt, picoline salt, quinoline salt and isoquinoline salt, etc.), quaternary ammonium salt (e.g., tetramethylammonium salt, tetraethylammonium salt, benzyltrimethylammonium salt, benzyltriethylammonium salt, benzyltributylammonium salt, methyltrioctylammonium salt and tetrabutylammonium salt, etc.), basic amino acid salt (e.g., arginine salt, lysine salt, etc.) and N-methyl-D-glucamine salts, etc.), acid adduct salt (e.g., inorganic acid salt (e.g. hydrochloride salt, hydrobromide salt, hydroiodide salt, sulphate, phosphate and nitrate etc.) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate, etc.), etc.) and the like. The pharmaceutically acceptable salt is preferably water-soluble.

In particular, among the compounds represented by the general formula (I-1) or the like in which any one of $R^{2d}$, $R^{4a}$ and $R^{6a}$ is the above-mentioned phosphonooxyalkyl group, examples of ones which form a salt along with the same group include the above-mentioned alkali metal salt, the above-mentioned alkaline earth metal salt, magnesium salt, zinc salt, ammonium salt, organic amine salt and the like, and among these salts, the alkali metal salt is preferably a sodium salt and potassium salt, the alkaline earth metal salt is preferably a calcium salt, and the organic amine salt is preferably a basic amino acid salt (e.g., arginine salt (e.g., L-arginine salt), lysine salt (e.g., L-lysine salt), etc.), meglumine salt, tris(hydroxymethyl)aminomethane salt and the like.

[Solvates]

The compound represented by the general formula (I) or the like, N-oxide thereof, prodrug thereof or pharmaceutically acceptable salt thereof and the compound represented by the general formula (I-1) or the like, N-oxide thereof or pharmaceutically acceptable salt thereof can also be converted into a solvate by a known method. The solvate is preferably low toxicity and water soluble. Examples of suitable solvates include a solvate with a solvent such as water and alcohols (e.g., ethanol etc.). Herein, a hydrate may be in the form of, for example, a polyhydrate such as a monohydrate or pentahydrate, or low hydrate such as a hemihydrate. Examples of the forms of the hydrates of the compound of the present invention include a monohydrate, dihydrate, trihydrate and di- to tri-hydrate. Further, examples of the forms of these hydrates include a clathrate hydrate. These hydrates can be obtained by precipitating the compound represented by the general formula (I), N-oxide thereof, prodrug thereof or pharmaceutically acceptable salts thereof, or the compound represented by the general formula (I-1), N-oxide thereof or pharmaceutically acceptable salt thereof from, for example, a water-containing organic solvent.

[Co-Crystal]

The compound represented by the general formula (I) or the like, N-oxide thereof, prodrug thereof, pharmaceutically acceptable salt thereof or solvate thereof, and the compound represented by the general formula (I-1) or the like, N-oxide thereof, pharmaceutically acceptable salt thereof, or solvate thereof can be co-crystallized with an appropriate co-crystal forming agent. The co-crystal is preferably a pharmaceutically acceptable one which can be co-crystallized with a pharmaceutically acceptable co-crystal forming agent. A co-crystal is defined as a crystal in which two or more different molecules are formed by intermolecular interactions different from ionic bonds. Further, the co-crystal may be a complex of a neutral molecule and a salt. The co-crystal can be prepared by known methods, for example, by melt crystallization, recrystallization from solvent or by physically grinding components together. Examples of the appropriate co-crystal forming agents include those described in WO2006/007448, such as 4-aminobenzoic acid, 4-aminopyridine, adenine, alanine, acetylsalicylic acid and the like.

[Radioisotopes]

The compound represented by the general formula (I) or the like, N-oxide thereof, prodrug thereof, pharmaceutically acceptable salt thereof or solvate thereof and the compound represented by the general formula (I-1) or the like, N-oxide thereof, pharmaceutically acceptable salt thereof or solvate thereof may be labeled with an isotope or the like (e.g., $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I, etc.). The examples include the compound in which all or part of hydrogen atoms constituting one or more groups among R', $R^2$, $R^3$, $R^4$, $R^5$, $R^6$ and $R^7$ in the general formula (I) or $R^1$, $R^{2c}$, $R^3$, $R^{4a}$, $R^5$, $R^{6a}$ and $R^7$ in the general formula (I-1) were replaced with heavy water atoms or tritium atoms, for example, 4-(4-amino-2-fluoro-5-(methoxy-d$_3$)phenyl)-7-(1H-pyrazol-4-yl)isoxazolo[4,5-c]pyridin-3-amine and the like. In the present specification, "methyl-d$_3$" and "methoxy-d$_3$" represent a triduteriomethyl group and triduteriomethoxy group, respectively.

[Method for Producing Compounds of the Present Invention]

The compound of the present invention can be produced by appropriately improving known methods, for example, the methods described in Comprehensive Organic Transformations: A Guide to Functional Group Preparations, 2nd Edition (Richard C. Larock, John Wiley & Sons Inc, 1999), the methods below, the methods shown in Examples and the like and then using them in combination.

Among the compounds represented by the general formula (I) or the like, the compound represented by the general formula (IV):

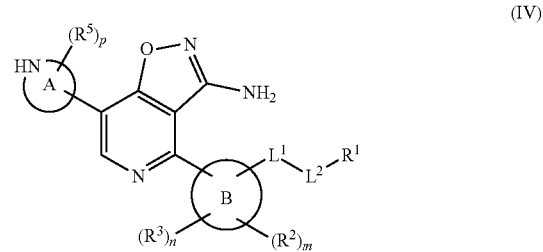

[wherein, all symbols have the same meanings as described above.] can be produced by the method represented by the following Reaction Scheme 1.

Reaction Scheme 1

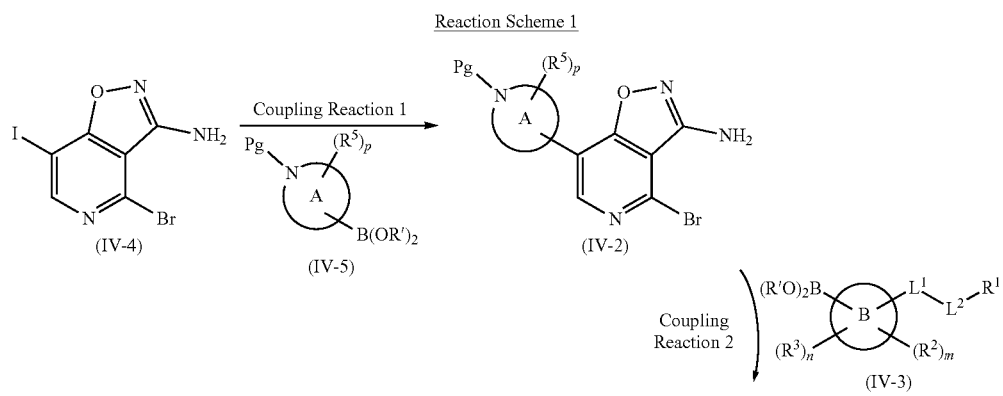

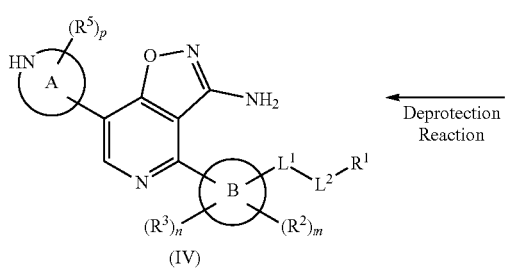

(IV)

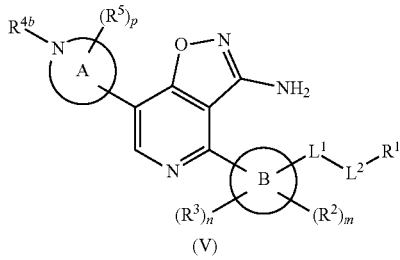

(V)

[wherein, Pg represents a protecting group for an amino group (e.g., a tert-butoxycarbonyl group, benzyloxycarbonyl group, fluorenylcarbonyl group, trityl group, o-nitrobenzenesulfenyl group or acetyl group), and R' represents each independently a hydrogen atom, C1-5 alkyl group, C3-6 cycloalkyl group, hydroxyl group or halogen atom, herein when R' represents a C1-5 alkyl group, two R's may form a dioxaborolane ring together with the adjacent oxygen atom and boron atom, and other symbols have the same meanings as described above.]

Coupling Reaction 1 in Reaction Scheme 1 can be carried out by the known Suzuki coupling reaction, for example, at 0 to 200° C., under the presence or absence of 0.01 to 100 mol % of a palladium catalyst (e.g., tetrakistriphenylphosphine palladium, bis(triphenylphosphine)palladium(II)dichloride, tris(dibenzylideneacetone)dipalladium, palladium acetate, palladium acetylacetonate, [1,1'-bis(diphenylphosphino)ferrocene]dichloropalladium dichloromethane complex or bis[di-tert-butyl(4-dimethylaminophenyl)phosphine]palladium, etc.) and 0.01 to 400 mol % of a phosphine ligand (e.g., triphenylphosphine, tri-tert-butylphosphine, tricyclohexylphosphine or di(1-adamantyl)-n-butylphosphine or the like), in an organic solvent (e.g. dichloromethane, chloroform, dioxane, ethyl acetate, methanol, ethanol, isopropyl alcohol, tetrahydrofuran, dimethylformamide or N-methylpyrrolidone, etc.) alone or a mixed solvent with water, under the presence or absence of 1 to 10 equivalents of a base (e.g., potassium carbonate, sodium carbonate, cesium carbonate, sodium hydroxide, potassium hydroxide, sodium phosphate, potassium triethylamine phosphate or N,N-diisopropylethylamine or the like), in the presence of 1 to 10 equivalents of a boric acid reagent.

Further, Coupling Reaction 1 can also be carried out by a known coupling reaction using an organometallic reagent, for example, the Negishi reaction using a zinc reagent instead of a boric acid reagent, the Still reaction using a tin reagent instead of the boric acid reagent, the Hiyama coupling using a silicon reagent instead of the boric acid reagent, and the Kumada reaction using a Grignard reagent instead of the boric acid reagent and a nickel catalyst instead of a palladium catalyst are also performed.

Coupling Reaction 2 in Reaction Scheme 1 is also performed by the known Suzuki coupling reaction, the Negishi reaction, the Still reaction, the Hiyama coupling, the Kumada reaction, or the like.

The deprotection reaction in Reaction Scheme 1 can be carried out by a known deprotection reaction under acidic conditions, for example, at 0 to 100° C. in an organic solvent (e.g., dichloromethane, chloroform, dioxane, ethyl acetate, methanol, isopropyl alcohol, tetrahydrofuran or anisole, etc.), in an organic acid (e.g., acetic acid, trifluoroacetic acid, methanesulfonic acid or p-tosylic acid, etc.) or inorganic acid (e.g., hydrochloric acid or sulfuric acid, etc.) or a mixture thereof (e.g., hydrogen bromide/acetic acid etc.), and in the presence or absence of 2,2,2-trifluoroethanol.

The compound represented by the general formula (I-1) or the like in which none of $R^{2d}$, $R^{4a}$ and $R^{6a}$ represents the preceding R' may be produced by the method represented by the preceding Reaction Scheme 1.

Further, among the compounds represented by the general formula (I-1) or the like, the compound represented by the general formula (V):

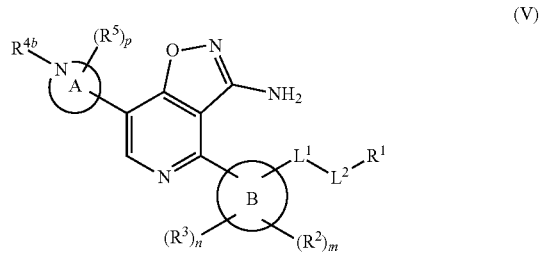

(V)

[wherein, $R^{4b}$ represents $—(CR^{Fb}_2)_q OP(=O)(OR^{Fa'})_2$, $R^{Fa'}$ represents each independently a hydrogen atom, C1-4 alkyl group, C3-6 cycloalkyl group, $—(CH_2)_2OH$ or $—CH_2OCO_2CH(CH_3)_2$ and other symbols have the same meanings as described above.] is produced by subjecting the compound represented by the general formula (IV) to the following alkylation reaction, and if $R^{Fa'}$ is a protecting group, being subjected it to a deprotection reaction, if necessary.

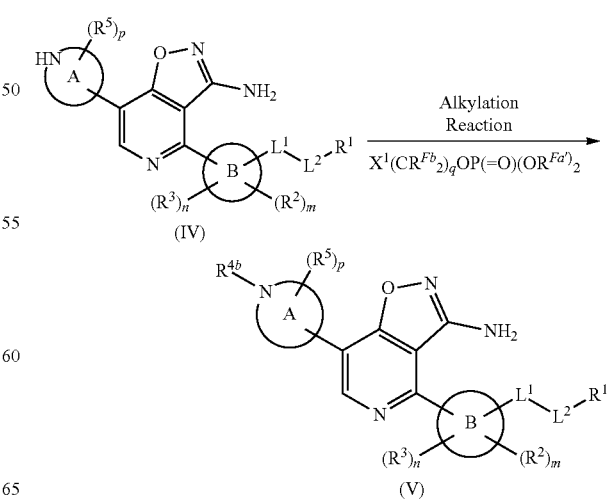

[wherein, $X^1$ represents a halogen atom, and other symbols have the same meanings as described above.]

Herein, the alkylation reaction is known, and for example, is carried out by reacting $X^1$ $(CR^{Fb})_qOP(=O)(OR^{Fa1})_2$ with the compound represented by the general formula (IV), in an organic solvent (e.g., dichloromethane, chloroform, dioxane, ethyl acetate, methanol, ethanol, isopropyl alcohol, tetrahydrofuran, dimethylformamide, N-methylpyrrolidone and dimethyl sulfoxide, etc.), in the presence of an inorganic base (potassium carbonate, sodium carbonate, cesium carbonate, sodium hydroxide or potassium hydroxide, etc.) or organic base (e.g., triethylamine, N, N-diisopropylamine, lithium diisopropylamide, lithium bis(trimethylsilyl)amide, sodium bis(trimethylsilyl)amide, potassium bis(trimethylsilyl)amide, tert-butylimino-tris(dimethylamino)phosphorane, tert-butylimino-tri(pyridino)phosphorane or 1,4-diazabicyclo[2.2.2]octane, etc.). Further, in the case that $R^{Fa1}$ is a protecting group, the deprotection reaction of $R^{Fa1}$ is also known, and for example, it can be carried out by the known deprotection reaction under acidic conditions or hydrogenation reaction in the presence of palladium-carbon catalyst or the like. In addition, in the case that $R^{Fa1}$ represents a protecting group, it corresponds to a protective group for a hydroxyl group, of which examples include a methyl group, trityl group, methoxymethyl group, 1-ethoxyethyl group, methoxyethoxymethyl group, 2-tetrahydropyranyl group, trimethylsilyl group, triethylsilyl group, tert-butyldimethylsilyl group, tert-butyldiphenylsilyl group, acetyl group, pivaloyl group, benzoyl group, benzyl group, p-methoxybenzyl group, allyloxycarbonyl group or 2,2,2-trichloroethoxycarbonyl group or the like. Further, the hydrogenation reaction in the presence of a palladium-carbon catalyst or the like is carried out, for example, at room temperature to 120° C., under a hydrogen gas atmosphere of 1 to 20 atm, in an organic solvent (e.g., methanol, ethanol, tetrahydrofuran, dioxane, ethyl acetate or isopropyl alcohol, etc.), in the presence of 0.01 to 100 mol % of catalyst (e.g., palladium-carbon, platinum-carbon, palladium hydroxide-carbon or rhodium-carbon, etc.).

The compound represented by the general formula (IV-4) in Reaction Scheme 1 can be produced by the method represented by the following Reaction Scheme 2.

Reaction Scheme 2

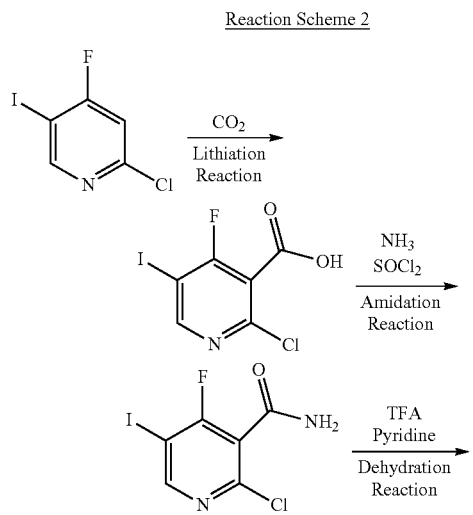
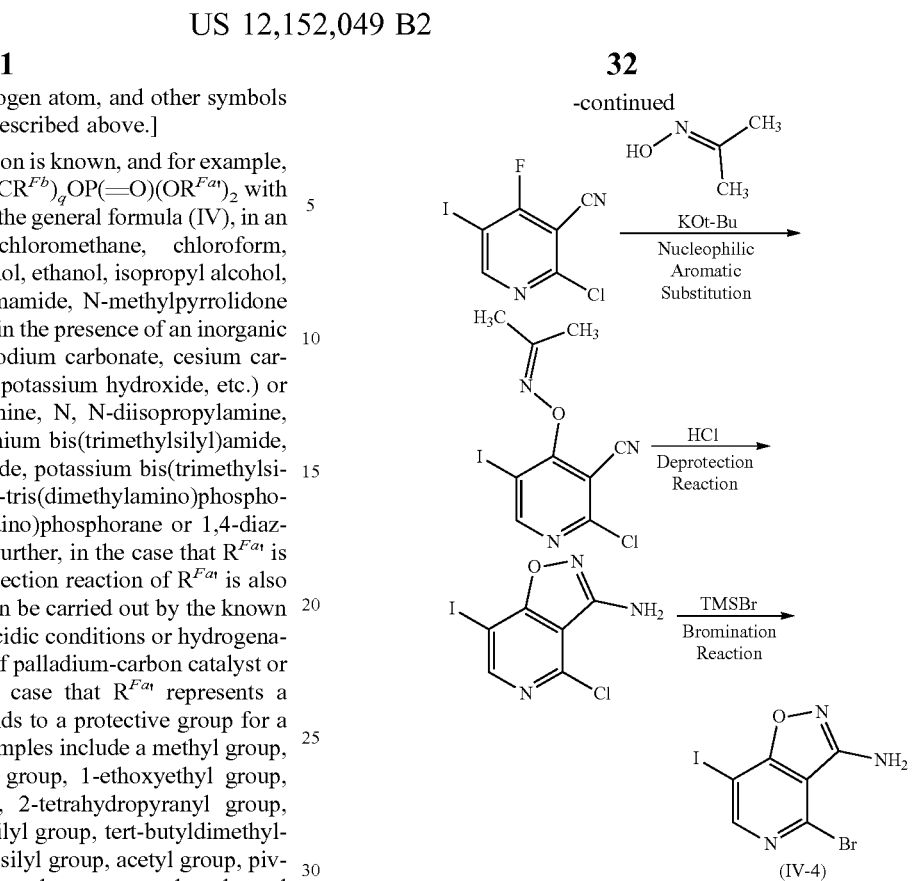

The lithiation reaction in Reaction Scheme 2 can be carried out by a known method, for example, by reacting a base (e.g., lithium diisopropylamide, n-butyllithium or tert-butyllithium, etc.) in an organic solvent (e.g., tetrahydrofuran, diethylether, dioxane, dichloromethane, dichloroethane, n-hexane or toluene, or a mixed solvent thereof, etc.), at −78° C. to room temperature, followed by addition of carbon dioxide (e.g., carbon dioxide gas or dry ice, etc.), and then reacting it at −78° C. to room temperature.

The amidation reaction in Reaction Scheme 2 can be carried out by a known method, for example, by reacting it to an acid halide agent (e.g., oxalyl chloride or thionyl chloride, etc.) at −78° C. to reflux temperature in an organic solvent (e.g., chloroform, dichloromethane, diethylether, tetrahydrofuran or dimethoxyethane, etc.) or under solvent-free condition, and then reacting the obtained acid halide at −78° C. to reflux temperature, with addition of ammonia (e.g., ammonia gas, ammonia water or ammonia methanol solution, etc.), in the presence or absence of a base (e.g., pyridine, triethylamine, dimethylaniline or N, N-dimethylaminopyridine, etc.).

The dehydration reaction in Reaction Scheme 2 can be carried out by a known method, for example, by reacting it at −78° C. to the reflux temperature, in the presence or absence of a solvent (e.g., chloroform, dichloromethane, diethylether, tetrahydrofuran or dimethoxyethane, etc.), in the presence or absence of a base (e.g., pyridine, triethylamine, dimethylaniline, N, N-dimethylaminopyridine or N, N-diisopropylethylamine, etc.), in the presence of a dehydrating agent (e.g., thionylchloride, trifluoroacetic anhydride, acetic anhydride, diphosphorus pentoxide or (methoxycarbonylsulfamoyl)triethylammonium hydroxide inner salt, etc.).

The nucleophilic aromatic substitution reaction in Reaction Scheme 2 can be carried out by a known method, for example, by reacting it at room temperature to 120° C., in an organic solvent (e.g., N, N-dimethylacetamide, N, N-dimethylformamide, tetrahydrofuran, acetonitrile, 2-propanol or dimethyl sulfoxide or a mixed solvent thereof, etc.), in the presence of 1 to 10 equivalents of acetoxime and a base (e.g., tert-butoxy potassium, tert-butoxy sodium, potassium carbonate, cesium carbonate, sodium hydrogen carbonate or tripotassium phosphate, etc.).

The deprotection reaction in Reaction Scheme 2 can be carried out by a known method, for example, a deprotection reaction under acidic condition. For example, it can be carried out at 0 to 100° C., in an organic solvent (e.g., dichloromethane, chloroform, dioxane, ethylacetate, methanol, isopropyl alcohol, tetrahydrofuran or anisole, etc.), in an organic acid (e.g., acetic acid, trifluoroacetic acid, methanesulfonic acid or p-tosylic acid, etc.) or an inorganic acid (e.g., hydrochloric acid or sulfuric acid, etc.) or a mixture thereof (e.g., hydrogen bromide/acetic acid etc.) in the presence or absence of 2,2,2-trifluoroethanol.

The bromination reaction in Reaction Scheme 2 can be carried out by a known method, for example, it can be carried out at −78° C. to 100° C., in an organic solvent (e.g., dichloromethane, chloroform, tetrahydrofuran, acetonitrile, dioxane, ethylacetate or acetic acid, etc.), in the presence or absence of 1 to 10 equivalents of a brominating agent (e.g., trimethylsilylbromide (TMSBr), bromine, hydrobromic acid or phosphorus tribromide, etc.) and 0.1 to 100 mol % of catalyst (e.g., copper (II) bromide or lithium bromide, etc.).

In the respective reactions in the present specification, the compounds used as a starting material, compounds or reagents to be added, for example, the compound represented by the general formula (IV-3) or general formula (IV-5) and the compound used in the alkylation reaction or Reaction Scheme 2 are known or can be produced according to known methods or the methods described in Examples.

Among the compounds used in the present invention, the compounds having optical activity can be produced by using starting materials or reagents having optical activity, by optically resolving a racemic intermediate and then conducing to the compound to be used in the present invention, or by optically resolving a racemic compound. This method of optical resolution is known, and for example, there is a method or the like to form a salt/complex with other optically active compounds and perform recrystallization, and then to isolate the desired compound or directly separate using a chiral column etc.

In the respective reactions in the present specification, the reaction involving heating can be performed using a water bath, oil bath, sand bath or microwave, as being apparent to those skilled in the art.

In the respective reactions in the present specification, a solid-phase supported reagent supported on a high-molecular polymer (e.g., polystyrene, polyacrylamide, polypropylene or polyethylene glycol, etc.) may be used as appropriate.

In the respective reactions in the present specification, the reaction products can be purified by conventional purification methods, for example, methods such as distillation under normal pressure or reduced pressure, high performance liquid chromatography using silica gel or magnesium silicate, thin layer chromatography, ion exchange resin, scavenger resin or column chromatography, washing, recrystallization and the like. Purification may be carried out for respective reactions or may be carried out after the completion of some reactions.

[Toxicity]

The compound of the present invention has sufficiently low toxicity and can be safely used as a pharmaceutical.

[Application to Pharmaceuticals]

Since the compound of the present invention has agonistic activity to STING, it can be prescribed as an effective agent for suppressing the progression of, suppressing the recurrence of or treating cancer or infectious disease.

In the present specification, examples of the term "treating cancer" include therapies (a) to decrease the proliferation of cancer cells, (b) to reduce symptoms caused by cancer, to improve the quality of life of a patient with cancer, (c) to reduce the dose of other already administered anti-cancer drugs or cancer therapeutic adjuvants and/or (d) to prolong the survival of a patient with cancer. And, the term "suppressing the progress of cancer" means to delay the progress of cancer, to stabilize symptoms associated with cancer, and to reverse the progress of symptoms. The term "suppressing the recurrence of cancer" means to prevent the recurrence of cancer in a patient of which cancer lesion had been completely or substantially eliminated or removed by cancer therapy or cancer resection surgery.

Further, in the present invention, the compound of the present invention can be prescribed to (a) a patient with cancer on which the therapeutic effects of other anti-cancer drugs are insufficient or not sufficient, or patient with cancer worsened after treatment with other anti-cancer drugs, (b) a patient with incurable or unresectable, metastatic, recurrent, refractory and/or distant metastatic cancer, (c) a patient with cancer of which TPS or CPS is 50% or more, 25% or more, 10% or more, 5% or more, or 1% or more, (d) a patient with MSI-H or dMMR cancer (e) a patient with BRAF V600E mutation-positive malignant melanoma or non-small cell lung cancer, (f) a patient with EGFR gene mutation-positive or ALK fusion gene-positive cancer, or (g) a patient with TMB high frequency cancer.

Further, on the other hand, the compound of the present invention may be required to be prescribed to (a) a patent with cancer which has not been treated with any anti-cancer drugs, (b) a patient with cancer in which TPS or CPS is less than 50%, less than 25%, less than 10%, less than 5% or less than 1%, (c) a patient with cancer without MSI-H and/or dMMR or with MSI-L, (d) a patient with BRAF V600 wild type malignant melanoma or non-small cell lung cancer, (e) a patient with EGFR gene mutation-negative and/or ALK fusion gene-negative non-small cell lung cancer, or (f) a patient with TMB low frequency cancer.

Furthermore, it also can be prescribed as a postoperative adjuvant therapy for preventively suppressing the recurrence or metastasis after surgical resection of cancer or as preoperative adjuvant therapy performed before surgical resection.

Herein, examples of "other anti-cancer drugs" include the anti-cancer drugs listed in the section [Combination and Combination preparation] below, that are, drugs exemplified, respectively, as alkylating agents, platinum preparations, antimetabolite antagonists (e.g., folate metabolism, pyridine metabolism inhibitors and purine metabolism inhibitors), ribonucleotide reductase inhibitors, nucleotide analogs, topoisomerase inhibitors, microtubule polymerization inhibitors, microtubule depolymerization inhibitors, antitumor antibiotics, cytokine preparations, anti-hormonal drugs, molecular targeting drugs, and cancer immunotherapeutic drugs. Further, "the therapeutic effects of other anti-cancer drugs are insufficient or not sufficient" means, for example, the case to be determined as stable (SD) or progression (PD) according to RECIST by even treatment with already-existing anti-cancer drugs.

Examples of cancers of which the progression and/or recurrence can be suppressed and/or which can be treated with the compound of the present invention include any solid cancers and blood cancers. Among solid cancers, examples of epithelial cell cancers include malignant melanoma (e.g., malignant melanoma in skin, oral mucosal epithelium, or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell cancer (e.g., clear cell renal cell cancer), breast cancer, ovarian cancer (e.g., serous ovarian cancer and ovarian clear cell adenocarcinoma), nasopharyngeal cancer, uterine cancer (e.g., cervical cancer and endometrial cancer), anal cancer (e.g., anal canal cancer), colorectal cancer (e.g., MSI-H and/or dMMR positive colorectal cancer), rectal cancer, colon cancer, hepatocellular carcinoma, esophageal cancer, gastric cancer, esophagogastric junction cancer, pancreatic cancer, urine urothelial cancer (e.g., bladder cancer, upper urinary tract cancer, ureteral cancer, renal pelvis cancer and urethral cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, small intestine cancer, endocrine system cancer, thyroid cancer, parathyroid cancer, adrenal carcinoma, spinal tumor, neuroblastoma, medulloblastoma, ocular retinoblastoma, neuroendocrine tumor, brain tumor (e.g., glioma (e.g., glioblastoma and gliosarcoma) and meningioma), squamous cell carcinoma and the like.

Among solid cancers, examples of sarcomas include bone/soft tissue sarcomas (e.g., Ewing sarcoma, pediatric rhabdomyosarcoma, endometrial leiomyosarcoma, chondrosarcoma, lung sarcoma, osteosarcoma and congenital fibrosarcoma), Kaposi's sarcoma and the like.

Examples of blood cancers include multiple myeloma, malignant lymphoma (e.g., non-Hodgkin lymphoma (e.g., follicular lymphoma, precursor B-cell lymphoblastic lymphoma, chronic B lymphocytic leukemia, nodal marginal zone B-cell lymphoma, diffuse large B-cell lymphoma, MALT lymphoma, splenic primary marginal zone B-cell lymphoma, hairy cell leukemia, primary mediastinal large B-cell lymphoma, Burkitt lymphoma, mantle cell lymphoma, mycosis fungoides, Sézary syndrome, chronic or acute lymphocytic leukemia, precursor T cell lymphoblastic lymphoma, chronic T lymphocytic leukemia, large granular T-cell leukemia, large granular NK-cell leukemia, peripheral T-cell lymphoma, extranodal NK/T-cell lymphoma, adult T-cell leukemia, angiocentric lymphoma, intestinal T-cell lymphoma, Hodgkin-like/Hodgkin-related anaplastic large cell lymphoma, B-cell lymphoblastic leukemia, T-cell lymphoblastic leukemia and lymphoplasmacytoid lymphoma) and Hodgkin lymphoma (e.g., classic Hodgkin lymphoma and nodular lymphoid predominant Hodgkin lymphoma)), leukemia (e.g., acute myelogenous leukemia and chronic myelogenous leukemia), central nervous system malignant lymphoma, myelodysplastic syndromes, myeloproliferative syndromes and the like.

Further, examples of cancers of which the progression and/or recurrence can be suppressed and/or which can be treated with the compound of the present invention include pediatric cancers and unknown primary cancers, as well.

Examples of infectious diseases of which the progression and/or recurrence can be suppressed and/or which can be treated with the compound of the present invention include symptoms caused by viral infection, parasitic infection, bacterial infection or fungal infection.

Examples of viral infections include infectious diseases which are caused by adenovirus, arenavirus, bunyavirus, calicivirus, coronavirus, Filovirus, hepadnavirus, herpesvirus, orthomyxovirus, papovavirus, paramyxovirus, parvovirus, picornavirus, poxvirus, reovirus, retrovirus, rhabdovirus, togavirus, papillomavirus (e.g., human papillomavirus (HPV)), human immunodeficiency virus (HIV), poliovirus, hepatitis virus (e.g., hepatitis A virus (HAV), hepatitis B virus (HBV), hepatitis C virus (HCV), hepatitis D virus (HDV) and hepatitis E virus (HEV)), smallpox virus (e.g., variola major and variola minor), vaccinia virus, influenza virus, rhinovirus, dengue virus, equine encephalitis virus, rubella virus, yellow fever virus, Norwalk virus, human T-cell leukemia virus (HTLV-I), hairy cell leukemia virus (HTLV-II), California encephalitis virus, hanta virus (hemorrhagic fever), rabies virus, Ebola virus, Marburg virus, measles virus, mumps virus, respiratory syncytial virus (RSV), herpes simplex type 1 (oral herpes), herpes simplex type 2 (genital herpes), herpes zoster (varicella-zoster virus), cytomegalovirus (CMV), Epstein-Barr virus (EBV), flavivirus, foot-and-mouth disease virus, Chikungunya virus, Lassa virus, arenavirus or oncovirus.

Examples of parasitic infection include acanthamoeba keratitis, amebiasis, ascariasis, babesiosis, valantidiosis, roundworm raccoon infection, Chagas disease, fascioliasis, cochliomyia, cryptosporidiosis, diphyllobothriasis, dracunculiasis, echinococcosis, elephantiasis, enterobiasis, liver fluke disease, hypertrophic liver fluke disease, filariasis, giardiasis, gnathostomiasis, hymenolepiasis, isosporosis, Katayama fever, leishmaniasis, Lyme disease, malaria, metagonimosis, flystrike, onchocerciasis, *Pediculus humanus* capitis, scabies, schistosomiasis, maladie du sommeil, strongyloidiasis, pork tapeworm, toxocariasis, toxoplasmosis, trichinellosis, trichocephaliasis and the like.

Examples of bacterial infection include infectious diseases caused by infection with tubercle bacillus, anthrax, pathogenic bacterium, food poisoning bacterium, salmonella, staphylococcus, streptococcus, tetanus bacillus, mycobacteria, tetanus bacterium, plague bacterium, anthrax and antibiotic-resistant bacteria such as methicillin-resistant *Staphylococcus aureus* (MRSA), *Clostridium difficile*, or other infectious bacterias.

Examples of fungal infection include infectious diseases caused by infection with *Aspergillus, Blastomyces dermatitisdis, Candida* yeast (e.g., *Candida albicans*), *Coccidioides, Cryptococcus neoformans, Cryptococcus gatti*, dermatophyte, *Fusarium*, histoplasmosis capsulati, mucoromycotina, *Pneumocystis jiroveci, Sprothrix schenckii, Exerohyrum* or *Cladosporium*.

[Combination or Combination Preparation]

In order to (a) suppress the progression, and/or recurrence of and/or enhance the therapeutic effect on cancer or infectious disease, (b) decrease the dose of other combined drugs, and/or (c) reduce the side effects of other combined drugs, (d) enhance immunoenhancing effects of other combined drugs, that is, as an adjuvant, the compound of the present invention or pharmaceutical composition containing the compound of the present invention as an active ingredient (hereinafter, abbreviated as "the compound of the present invention or the like") may be used in combination with one or more kinds of other drugs. In the present invention, the formulation which is prescribed in combination with other drugs may be of a combination preparation which both components are mixed in one preparation or of separated preparations. The combination can compensate the effects in preventing, suppressing the progression of, suppressing the recurrence of and/or treating disease with other drugs, and reduce the dose or frequency of its administration. In the case that the compound of the present invention or the like and other drugs are administered separately, both may be administered simultaneously for a certain period, and then only the compound of the present invention or the like or other drugs may be administered alone. Further, the compound of the present invention or the like may be administered initially, followed by administration with other drugs, or other drugs may be administered initially, followed by administration with the compound of the present invention or the like. In the above administration, there may be a certain period in which both drugs are administered, simultaneously. Further, the administration methods of the respective drugs may be the same or different. Depending on the nature of the drug, it can also be provided as a kit containing the compound of the present invention and other drugs. Herein, the dose of other drugs can be appropriately selected based on a dose clinically used. Further, other drugs may be administered in combination of two or more kinds of other drugs at an appropriate ratio. Furthermore, examples of other drugs include those which would be found in the future, as well as those which have been found to date.

In cancer treatment, examples of anti-cancer drugs which can be used in combination with the compound of the present invention or the like include an alkylating agent (e.g., dacarbazine, Nimustine, Temozolomide, Fotemustine, bendamustine, Cyclophosphamide, Ifosfamide, Carmustine, Chlorambucil and Procarbazine, etc.), platinum preparation (e.g., Cisplatin, Carboplatin, Nedaplatin and oxaliplatin, etc.), antimetabolite (e.g., folic acid antimetabolites (e.g., Pemetrexed, leucovorin and Methotrexate etc.), pyridine metabolism inhibitor (e.g., TS-1) (Registered trademark), 5-fluorouracil, UFT, Carmofur, Doxifluridine, FdUrd, Cytarabine and Capecitabine, etc.), purine metabolism inhibitor (e.g., Fludarabine, Cladribine and Nelarabine, etc.), ribonucleotide reductase inhibitor, nucleotide analogue (e.g., Gemcitabine etc.)), topoisomerase inhibitor (e.g., Irinotecan, Nogitecan and Etoposide, etc.), microtubule polymerization inhibitor (e.g., Vinblastine, Vincristine, Vindesine, Vinorelbine, Eribulin, etc.), microtubule depolymerization inhibitor (e.g., Docetaxel and Paclitaxel), antitumor antibiotic (e.g., Bleomycin, Mitomycin C, Doxorubicin, Daunorubicin, Idarubicin, Etoposide, Mitoxantrone, Vinblastine, Vincristine, Peplomycin, Amrubicin, Aclarubicin and Epirubicin, etc.), cytokine preparation (e.g., IFN-α2a, IFN-α2b, peg IFN-α2b, natural IFN-β and interleukin-2, etc.), anti-hormonal drug (e.g., Tamoxifen, Fulvestrant, Goserelin, Leuprorelin, Anastrozole, Letrozole and Exemestane, etc.), molecularly targeted drug, cancer immunotherapeutic drug and other antibody drugs, etc.

Herein, examples of the molecular targeting drug include an ALK inhibitor (e.g., Crizotinib, Ceritinib, Ensartinib, Alectinib and Lorlatinib), BCR-ABL inhibitor (e.g., Imatinib and Dasatinib), EGFR inhibitor (e.g., Erlotinib, EGF816, Afatinib, Osimertinib mesylate, Gefitinib and Rociletinib), B-Raf inhibitor (e.g., Sorafenib, Vemurafenib, TAK-580, Dabrafenib, Encorafenib, LXH254, Emurafenib and BGB-3111), VEGFR inhibitor (e.g., Bevacizumab, Apatinib, Lenvatinib, Aflibercept and Axitinib), FGFR inhibitor (e.g., AZD4547, B-701, FGF401 and INCB054828), c-Met inhibitor (e.g., Savolitinib, merestinib, Capmatinib, INC280 and Glesatinib), Axl inhibitor (e.g., ONO-7475 and BGB324), Mek inhibitor (e.g., Cobimetinib, Binimetinib, Selumetinib and Trametinib), CDK inhibitor (e.g., Dinaciclib, Abemaciclib, Palbociclib and trilaciclib), Btk inhibitor (e.g., ONO-4059, Ibrutinib and Acalabrutinib), PI3K-δ/γ inhibitor (e.g., TGR-1202, INCB050465 and IPI-549), JAK-1/2 inhibitor (e.g., Itacitinib and Ruxolitinib), ERK inhibitor (e.g., SCH 900353), TGFbR1 inhibitor (e.g., Galunisertib), Cancer cell stemness kinase inhibitor (e.g., Amcasertib), FAK inhibitor (e.g., Defactinib), Syk/FLT3 dual inhibitor (e.g., TAK-659), ATR inhibitor (e.g., AZD6738), Wee1 kinase inhibitor (e.g., AZD1775), Multi-tyrosine kinase inhibitor (e.g., Sunitinib, Pazopanib, Cabozantinib, Regorafenib, Nintedanib, Sitravatinib and Midostaurin), mTOR inhibitor (e.g., Temsirolimus, Everolimus, Vistusertib, Irinotecan), HDAC inhibitor (e.g., Vorinostat, Romideps). Entinostat, Chidamide, Mocetinostat, Citarinostat, Panobinostat, Valproate), PARP inhibitor (e.g., Niraparib, Olaparib, Veliparib, Rucaparib, Beigene-290), aromatase inhibitor (e.g., Exemestane, Letrozole), EZHaze inhibitor (e.g., tazemetostat), Galectin-3 inhibitor (e.g., GR-MD-02), STAT3 inhibitor (e.g., Napabucasin), DNMT inhibitor (e.g., Azacitidine), SMO inhibitor (e.g., Vismodegib), Hsp90 inhibitor (e.g., XL888), γ-tubulin specific inhibitor (e.g., Glaziovianin A, Plinabulin), HIF2α inhibitor (e.g., PT2385), glutaminase inhibitor (e.g., CB-839), E3 ligase inhibitor (e.g., Avadomide), Nrf2 activator (e.g., Omaveloxolone), arginase inhibitor (e.g., CB-1158), Cell cycle inhibitor (e.g., Trabectedin), Ephrin B4 inhibitor (e.g., sEphB4-HAS), IAP antagonist (e.g., Birinapant), anti-Her2 antibody (e.g., Trastuzumab, Trastuzumab emtansine, Pertuzumab and Margetuximab), anti-EGFR antibody (e.g., Cetuximab, Panitumumab, Necitumumab and Nimotuzumab). Anti-VEGF antibody (e.g., Bevacizumab), anti-VEGFR2 antibody (e.g., Ramucirumab), anti-CD20 antibody (e.g., Rituximab, Ofatumumab, Ublituximab and Obinutuzumab), anti-CD30 antibody (e.g., Brentuximab Vedotin), anti-CD38 antibody (e.g., Daratumumab), Anti-DR5 antibody (e.g., DS-8273a), anti-CA125 antibody (e.g., Oregovomab), anti-DLL4 antibody (e.g., Demcizumab), anti-fucosyl GM1 antibody (e.g., BMS-986012), anti-gpNMB antibody (e.g., Glembatumumab vedotin), anti-Mesothelin antibody (e.g., BMS-986148), anti-MMP9 antibody (e.g., Andecaliximab), anti-GD2 antibody (e.g., Dinutuximab-(3), anti-c-Met antibody (e.g., ABT-399), anti-FOLR1 antibody (e.g., Miryetuximab soravtansine), anti-Ang2-VEGF bispecific antibody (e.g., Vanucizumab), Anti-CD30-CD16A bispecific antibody (e.g., AFM13), anti-CD79b antibody (e.g., Polatuzumab Vedotin), anti-FAP antibody/IL-2 fusion protein (e.g., RO6874281), anti-CEA antibody/IL-2 fusion protein (e.g., Cergutuzumab amunaleukin), anti-CEA-CD3 bispecific antibody (e.g., RO6958688), anti-DLL3 antibody (e.g., Rovalpituzumab tesirine), anti-CD3-CD19 bispecific antibody (e.g., Blinatumomab), anti-CD20-CD3 bispecific antibody (e.g., REGN1979) and the like.

Examples of cancer immunotherapeutic agents include an anti-PD-1 antibody (e.g., Nivolumab, Cemiplimab (REGN-2810), Pembrolizumab (MK-3475), Spartalizumab (PDR-001), Tislelizumab (BGB-A317), AMP-514 (MEDI0680), Dostarlimab (ANB011/TSR-042), Tripalimab (JS001), Camrelizumab (SHR-1210), Genolimzumab (CBT-501), Sintilimab (IBI308), STI-A1110, ENUM 388D4, ENUM 244C8, GLS010, MGA012, AGEN2034, CS1003, HLX10, BAT-1306, AK105, AK103, BI 754091, LZMO09, CMAB819, Sym021, GB226, SSI-361, JY034, HX008, ABBV181, BCD-100, PF-06801591, CX-188, JNJ-63723283 and AB122, etc.), anti-PD-L1 antibody (e.g., Atezolizumab (RG7446/MPDL3280A), Avelumab (PF-06834635/MSB0010718C), Durvalumab (MEDI4736), BMS-936559, STI-1014, KNO35, LY3300054, HLX20, SHR-1316, CS1001, MSB2311, BGB-A333, KL-A167, CK-301, AK106, AK104, ZKAB001, FAZ053, CBT-502, JS003 and CX-072, etc.), PD-1 antagonist (e.g., each compound of AUNP-12 and BMS-M1 to BMS-M10 (see WO2014/151634, WO2016/039749, WO2016/057624, WO2016/077518, WO2016/100285, WO2016/100608, WO2016/126646, WO2016/149351, WO2017/151830 and WO2017/176608), BMS-1, BMS-2, BMS-3, BMS-8, BMS-37, BMS-200, BMS-202, BMS-230, BMS-242, BMS-1001 and BMS-1166 (see WO2015/034820, WO2015/160641, WO2017/066227 and Oncotarget. 2017 Sep. 22; 8 (42): 72167-72181.), Each compound of Incyte-1 to Incyte-6 (see WO2017/070089, WO2017/087777, WO2017/106634, WO2017/112730, WO2017/192961 and WO2017/205464), CAMC-1 to CAMC-4 (see WO2017/202273, WO2017/202274, WO2017/202275 and WO2017/202276), RG_1 (see WO2017/118762) and DPPA-1 (see Angew. Chem. Int. Ed. 2015, 54, 11760-11764), etc.), PD-L1/VISTA antagonist (e.g., CA-170 etc.), PD-L1/TIM3 antagonist (e.g., CA-327 etc.), anti-PD-L2 antibody, PD-L1 fusion protein, PD-L2 fusion protein (e.g., AMP-224 etc.), anti-CTLA-4 antibody (e.g., Ipilimumab (MDX-010), AGEN1884 and Tremelimumab, etc.), anti-LAG-3 antibody (e.g., Relatlimab (BMS-986016/ONO-4482), LAG525, REGN3767 and MK-4280, etc.), LAG-3 fusion protein (e.g., IMP321 etc.), anti-Tim3 antibody (e.g., MBG453 and TSR-022, etc.), anti-MR antibody (e.g., Lirilumab (BMS-986015/ONO-4483), IPH2101, LY3321367 and MK-4280, etc.), anti-BTLA antibody, anti-TIGIT antibody (e.g., Tiragolumab (MTIG-7192A/RG-6058/RO-7092284) and BMS-986207 (ONO-4686), etc), anti-VISTA antibody (e.g., JNJ-61610588 etc.), anti-CD137 antibody (e.g., Urelumab (ONO-4481/BMS-663513) and Utomilumab (PF-05082566), etc.), anti-CSF-1R antibody/CSF-1R inhibitor (e.g., Cabiralizumab (FPA008/BMS-986227/ONO-4687), Emactuzumab (RG7155/RO5509554), LY3022855, MCS-110, IMC-CS4, AMG820, Pexidartinib, BLZ945 and ARRY-382, etc.), anti-OX40 antibody (e.g., MEDI6469, PF-04518600, MEDI0562, MEDI6383, Efizonerimod, GSK3174998, BMS-986178 and MOXR0916, etc.), anti-HVEM antibody, anti-CD27 antibody (e.g., Varlilumab (CDX-1127) etc.), anti-GITR antibody (e.g., MK-4166, INCAGN01876, GWN323 and TRX-518, etc.), anti-CD28 antibody, anti-CCR4 antibody (e.g., Mogamulizumab etc.), anti-B7-H3 antibody (e.g., Enoblituzumab etc.), anti-ICOS agonist antibody (e.g., JTX-2011 and GSK3359609, etc.), anti-CD4 antibody (e.g., MTRX-1011A, TRX-1, Ibalizumab, huB-F5, Zanolimumab, 4162W94, Clenoliximab, Keliximab, AD-519, PRO-542, Cedelizumab, TNX-355, Dacetuzumab, Tregalizumab, Priliximab, MDX-CD4, CAMPATH-9 and IT1208, etc.), anti-DEC-205 antibody/NY-ESO-1 fusion protein (e.g., CDX-1401 etc.), Anti-SLAMF7 antibody (e.g., Elotuzumab etc.), anti-CD73 antibody (e.g., Oleclumab and BMS-986179, etc.), anti-CD122 antibody (e.g., NKTR-214 etc.), anti-CD40 agonist antibody (e.g., ABBV-428, APX005M and RO7009789, etc.), IDO inhibitor (e.g., Epacadostat, Indoximod and BMS-986205, etc.), TLR agonist (e.g., Motolimod, CMP-001, G100, IMO-2125, SD-101 and MEDI9197, etc.), adenosine A2A receptor antagonist (e.g., Preladenant, AZD4635, PBF 509 and CPI-444, etc.), anti-NKG2A antibody (e.g., Monalizumab etc.), anti-CSF-1 antibody (e.g., PD0360324 etc.), immunopotentiator (e.g., PV-10 etc.), IL-15 super agonist (e.g., ALT-803 etc.), soluble LAG3 (e.g., IMP321 etc.), CD47 antagonist (e.g., ALX148 etc.) and IL-12 antagonist (e.g., M9241 etc.) and the like. Incidentally, Nivolumab can be produced according to the method described in WO2006/121168, Pembrolizumab can be produced according to the method described in WO2008/156712, BMS-936559 can be produced according to the method described in WO2007/005874, and Ipilimumab can be produced according to the method described in WO2001/014424.

Further, examples of other antibody drugs include an anti-IL-10 antibody (e.g., Canakinumab etc.), anti-CCR2 antibody (e.g., Plozalizumab etc.) and the like.

[Prescription]

In order to use the compound of the present invention or the like, or the combination of the compound of the present invention and other drugs for the above purpose, it is usually administered systemically or locally, orally or parenterally. The dose varies depending on age, weight, symptoms, therapeutic effects, administration methods, treatment time and the like, but usually, it is orally administered once per adult in the range of 1 ng to 2,000 mg once a day or several times a day, or it is parenterally administered once per adult in the range of 0.1 ng to 200 mg once a day or several times a day, or intravenously administered continuously in the range of 30 minutes to 24 hours per day. Of course, as described above, since the dose varies depending on various conditions, a dose smaller than the above dose may be sufficient, or a dose exceeding the range may be required.

[Formulation]

When a compound of the present invention or the like or a combination of the compound of the present invention and other drugs is administered, a solid preparation or liquid preparation for oral administration, a sustained-release preparation or controlled-release preparation for oral administration, or an injection, infusion, external preparation, inhalant, suppository or the like for parenteral administration is used.

Examples of the solid preparation for oral administration include tablets, pills, capsules, powders, granules and the like, and examples of capsules include hard capsules, soft capsules and the like.

The solid preparation may be prepared, for example, by formulating the compound of the present invention along with a pharmaceutically acceptable carrier. Herein, examples of the pharmaceutically acceptable carrier used for formulating the solid preparations include an excipient (e.g., lactose, mannitol, glucose, microcrystalline cellulose and starch), binder (e.g., hydroxylpropylcellulose, polyvinylpyrrolidone and magnesium aluminometasilicate, etc.), disintegrant (e.g., calcium fibrin glycolate etc.), lubricant (e.g., magnesium stearate etc.), stabilizer, solubilizer (e.g., glutamic acid and aspartic acid, etc.) and the like. If necessary, it may be coated with a coating agent (e.g., sucrose, gelatin, hydroxypropylcellulose or hydroxypropylmethylcellulose phthalate, etc.), or may be coated with two or more layers. Further, it may be contained in a capsule containing gelatin.

The liquid preparation for oral administration may be in any form such as aqueous solution, suspension, emulsion, syrup, elixir or the like. For example, the compound of the present invention may be dissolved, suspended or emulsified in a diluent (e.g., purified water, ethanol or a mixed solution thereof or the like) to prepare a preparation. Further, the liquid preparation may contain a wetting agent, suspending agent, emulsifying agent, sweetening agent, flavoring agent, aromatic agent, preservative, buffering agent or the like.

The sustained-release preparation for oral administration may contain, for example, a gel-forming substance, and examples of the gel-forming substances include a gum arabic, agar, polyvinylpyrrolidone, sodium alginate, propylene glycol alginate, carboxyvinyl polymer, carboxymethyl cellulose, sodium carboxymethyl cellulose, guar gum, gelatin, hydroxypropyl methyl cellulose, hydroxypropyl cellulose, polyvinyl alcohol, methyl cellulose, hydroxyethyl methyl cellulose or the like.

The injection or infusion for parenteral administration may be in the form of aqueous solution, suspension or emulsion, and may be formulated as a solid formulation with a pharmaceutically acceptable carrier so that it can be dissolved, suspended or emulsified by adding a solvent (e.g., distilled water for injection, physiological saline, glucose solution and isotonic solution (e.g., a solution of sodium chloride, potassium chloride, glycerin, mannitol, sorbitol, boric acid, borax or propylene glycol, etc.), etc.) when needed. Herein, examples of the "pharmaceutically acceptable carrier" include a stabilizer (e.g., various amino acids, albumin, globulin, gelatin, mannitol, glucose, dextran, ethylene glycol, propylene glycol, polyethylene glycol, ascorbic acid, sodium hydrogen sulfite, sodium thiosulfate, sodium edetate, sodium citrate and dibutylhydroxytoluene, etc.), solubilizer (e.g., alcohol (e.g., ethanol etc.)), polyalcohol (e.g., propylene glycol, polyethylene glycol, etc.) and nonionic surfactant (e.g., Polysorbate 20 (registered trademark), Polysorbate 80 (registered trademark) and HCO-50, etc.), etc.), suspending agent (e.g., glyceryl monostearate, aluminium monostearate, methyl cellulose, carboxymethyl cellulose, hydroxymethyl cellulose and sodium lauryl sulfate, etc.), emulsifier (e.g., gum arabic, sodium alginate and tragacanth, etc.), soothing agent (e.g., benzyl alcohol, chlorobutanol and sorbitol, etc.), buffer (e.g., phosphate buffer, acetate buffer, borate buffer, carbonate buffer, citrate buffer, Tris buffer, glutamate buffer and epsilon aminocaproate buffer, etc.), preservative (e.g., methyl paraoxybenzoate, ethyl paraoxybenzoate, propyl paraoxybenzoate, butyl paraoxybenzoate, chlorobutanol, benzyl alcohol, benzalkonium chloride, dehydro sodium acetate, sodium edetate, boric acid and borax, etc.), antiseptic agent (e.g., benzalkonium chloride, paraoxybenzoic acid and chlorobutanol, etc.), pH adjuster (e.g., hydrochloric acid, sodium hydroxide, phosphoric acid and acetic acid, etc.), antioxidant and the like. As the antioxidant, for example, (1) a water-soluble antioxidant such as ascorbic acid, cysteine hydrochloride, sodium bisulfate, sodium metabisulfite, sodium sulfite or the like, (2) an oil-soluble antioxidant such as ascorbyl palmitate, butylated hydroxyanisole, butylated hydroxytoluene, lecithin, propyl gallate, α-tocopherol or the like, and (3) a metal chelating agent such as citric acid, ethylenediaminetetraacetic acid, sorbitol, tartaric acid, phosphoric acid or the like, can be used.

The injection or infusion can be produced by sterilizing it in the final step or by an aseptic operation method, for example, filtering with a filter or the like, and then filling a sterile container. And, the injection or infusion may be used by dissolving a sterile powder obtained by vacuum drying and freeze-drying (which may contain a powder of pharmaceutically acceptable carrier) in a suitable solvent before use.

Examples of the forms of external preparation for parenteral administration include a propellant, inhalant, spray, aerosol, ointment, gel, cream, poultice, patch, liniment, nasal drop, and the like.

Such a propellant, inhalant and spray may contain a stabilizer such as sodium bisulfite other than commonly used diluents and buffers giving isotonicity, for example, an isotonic agent such as sodium chloride, sodium citrate or citric acid. The method for producing the sprays is described in, for example, U.S. Pat. Nos. 2,868,691 and 3,095,355, in detail.

Examples of the inhalants include an inhalant liquid and inhalant powder, and the liquid may be in a form of being dissolved or suspended in water or other appropriate mediums before use. These inhalants can be manufactured according to known methods, for example, in the case of the inhalant liquid, they can be prepared by appropriately mixing a preservative (e.g., benzalkonium chloride and paraben, etc.), coloring agent, buffer (e.g., sodium phosphate and sodium acetate, etc.), isotonicity agent (e.g., sodium chloride and concentrated glycerin, etc.), thickener (e.g., carboxyvinyl polymer etc.), absorption enhancer and the like, if necessary, and in the case of the inhalant powder, they can be prepared by appropriately mixing a lubricant (e.g., stearic acid and salt thereof, etc.), binder (e.g., starch and dextrin, etc.), excipient (e.g., lactose and cellulose, etc.), coloring agent, preservative (e.g., benzalkonium chloride and paraben, etc.), absorption enhancer and the like, if necessary. When administering the inhalant liquid, a nebulizer (e.g., atomizer and nebulizer, etc.) is usually used, while when administering the inhalant powder, an inhaler for a powdered medicine is usually used.

The ointment is prepared in a known or commonly used formulation, for example, can be prepared by mixing or melting the compound of the present invention in an ointment base. Herein, the ointment base can be selected from known or commonly used ones, which is used by mixing with, for example, one or more kinds selected from a higher fatty acid or higher fatty acid ester (e.g., adipic acid, myristic acid, palmitic acid, stearic acid, oleic acid, adipic acid ester, myristic acid ester, palmitic acid ester, stearic acid ester and oleic acid ester, etc.), waxes (e.g., beeswax, whale wax and ceresin, etc.), surfactant (e.g., polyoxyethylene alkyl ether phosphate etc.), higher alcohol (e.g., cetanol, stearyl alcohol and cetostearyl alcohol, etc.), silicone oil (e.g., dimethyl polysiloxane etc.), hydrocarbons (e.g., hydrophilic petrolatum, white petrolatum, purified lanolin and liquid paraffin, etc.), glycols (e.g., ethylene glycol, diethylene glycol, propylene glycol, polyethylene glycol and macrogol, etc.), vegetable oil (e.g., castor oil, olive oil, sesame oil and turpentine oil, etc.), animal oil (e.g., mink oil, egg yolk oil, squalane and squalene, etc.), water, absorption promoter and anti-rash agent. Further, it may contain a moisturizing agent, preservative, stabilizer, antioxidant, flavoring agent or the like.

The gel is prepared in a known or commonly used formulation, for example, can be prepared by melting the compound of the present invention in a gel base. Herein, the gel base is selected from known or commonly used ones, which is used by mixing with, for example, one or more kinds selected from a lower alcohol (e.g., ethanol and isopropyl alcohol, etc.), gelling agent (e.g., carboxymethyl cellulose, hydroxyethyl cellulose, hydroxypropyl cellulose and ethyl cellulose, etc.), neutralizing agent (e.g., triethanolamine and diisopropanolamine, etc.), surfactant (e.g., polyethylene glycol monostearate etc.), gums, water, absorption promoter and anti-rash agent. Further, it may contain a preservative, antioxidant, flavoring agent or the like.

The cream is prepared in a known or commonly used formulation, for example, can be prepared by melting or emulsifying the compound of the present invention in a cream base. Herein, the cream base is selected from known or commonly used ones, which is used by mixing with, for example, one or more kinds selected from a higher fatty acid ester, lower alcohol, hydrocarbons, polyhydric alcohol (e.g., propylene glycol and 1,3-butylene glycol, etc.), higher alcohol (e.g., 2-hexyldecanol and cetanol, etc.), emulsifier (e.g., polyoxyethylene alkyl ethers and fatty acid esters, etc.), water, absorption promoter and anti-rash agent. Further, it may contain a preservative, antioxidant, flavoring agent or the like.

The poultice is prepared in a known or commonly used formulation, for example, can be prepared by melting the compound of the present invention in a poultice base and spreading and coating it on a support as a kneaded product. Herein, the poultice base is selected from known or commonly used ones, which is used by mixing with, for example, one or more kinds selected from a thickener (e.g., polyacrylic acid, polyvinylpyrrolidone, arabic gum, starch, gelatin and methylcellulose, etc.), wetting agent (e.g., urea, glycerin and propylene glycol, etc.), filler (e.g., kaolin, zinc oxide, talc, calcium and magnesium, etc.), water, solubilizing agent, tackifier, and anti-rash agent. Further, it may contain a preservative, antioxidant, flavoring agent or the like.

The patch is prepared in a known or commonly used formulation, for example, can be prepared by melting the compound of the present invention in a patch base and spreading and coating it on a support. Herein, the patch base is selected from known or commonly used ones, which is used by mixing with, for example, one or more kinds selected from a polymer base, fats and oils, higher fatty acid, tackifier and anti-rash agent. Further, it may contain a preservative, antioxidant, flavoring agent or the like.

The liniment is prepared in a known or commonly used formulation, for example, can be prepared by dissolving, suspending or emulsifying the compound of the present invention in one or more kinds selected from water, an alcohol (e.g., ethanol and polyethylene glycol, etc.), higher fatty acid, glycerin, soap, emulsifier, suspending agent and the like. Further, it may contain a preservative, antioxidant, flavoring agent or the like.

The contents of all patent documents and non-patent documents or references explicitly cited in the present specification may be incorporated herein as part of the present specification.

The present invention will be described in more detail by the following Examples, but the scope of the present invention is not limited thereto. Various changes or modifications can be made by those skilled in the art based on the description of the present invention, and these changes or modifications are also included in the present invention.

EXAMPLE

Hi-flash SI or Hi-flash NH in parentheses shown in the section of medium pressure preparative liquid chromatography represents the type of column used (Hi-flash SI: silica gel (manufactured by Yamazen Co., Ltd.), Hi-flash NH: aminopropyl group-supporting silica gel (manufactured by Yamazen Co., Ltd.)).

LC-MS/ELSD was performed under the following conditions:

[Column: YMC Triart C18 (particle size: $1.9 \times 10^{-6}$ m; column length: $30 \times 2.0$ mm ID); flow rate: 1.0 mL/min; column temperature: 40° C.; mobile phase (A): 0.1% trifluoroacetic acid solution; mobile phase (B): 0.1% trifluoroacetic acid-acetonitrile solution; gradient (show the ratio of mobile phase (A):mobile phase (B)): [0 min] 95:5; [0.1 min] 95:5; [1.2 min] 5:95; [1.4 min] 5:95; [1.41 min] 95:5; [1.5 min] 95:5; and detector: UV (PDA), ELSD, MS]

Numerical values shown at NMR are the $^1$H-NMR-measured values (chemical shift values) when the measurement solvent described in the parentheses is used.

The compound names used in the present specification are named by using computer programs: ACD/Name (registered trademark) (version 6.00, manufactured by Advanced Chemistry Development Inc.), Chemdraw Ultra (version 12.0, manufactured by Cambridge Soft) or Lexichem Toolkit (version 1.4.2, manufactured by OpenEye Scientific Software), which generally names according to IUPAC rules, or named according to the IUPAC nomenclature.

Reference Example 1: Lithium 2-chloro-4-fluoro-5-iodonicotinate

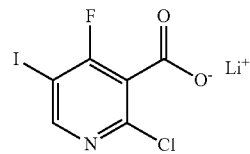 [SMILES: O=C([O-])c1c(Cl)ncc(I)c1F ; [Li+]]

2-chloro-4-fluoro-5-iodopyridine (CAS No. 1370534-60-3) (13.4 g) was dissolved in tetrahydrofuran (hereinafter, abbreviated as THF) (50 mL) and cooled to −78° C. Then, lithium diisopropylamide (1 mol/L THF solution, 50 mL) was added dropwise thereto over 30 minutes. After stirring at −78° C. for 1.5 hours, finely crushed dry ice (11.4 g) was added thereto, which was stirred at −78° C. for 30 minutes. The reaction solution was warmed to room temperature and the resulting precipitate was collected by filtration to give the title compound (16.5 g) having the following physical property value.

LCMS retention time (min): 0.63;
MS (ESI, Pos.): 302 (M+H)$^+$;
$^1$H-NMR (DMSO-d$_6$): δ 8.44 (d, J=9.0 Hz, 1H).

Reference Example 2: 2-chloro-4-fluoro-5-iodonicotinonitrile

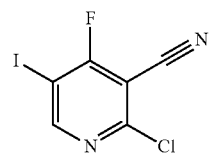 [SMILES: N#Cc1c(Cl)ncc(I)c1F]

A mixture of the compound (16.0 g) prepared in Reference Example 1, N, N-dimethylformamide (hereinafter, abbreviated as DMF) (0.20 mL) and thionyl chloride (38.0 mL) was stirred at 80° C. for 3.5 hours. The reaction solution was concentrated, and the THF solution dissolving the residue obtained therefrom (100 mL) was cooled to 0° C., to which saturated aqueous ammonia (28%, 10.8 mL) was added dropwise with stirring. After stirring for 30 minutes, tap water was added to the reaction mixture, which was extracted with ethyl acetate. The organic layer was washed with saturated saline, dried over sodium sulfate, and concentrated. The residue obtained therefrom was used in the next step without purification.

The crude product obtained by the above operation was dissolved in THF (174 mL), to which pyridine (21.1 mL) and trifluoroacetic anhydride (10.9 mL) were added under ice cooling, of which the mixture was stirred at 0° C. for 1 hour. A saturated aqueous sodium hydrogen carbonate solution was added to the reaction solution, of which the mixture was extracted with ethyl acetate. The organic layer was washed with saturated saline, dried over sodium sulfate, and concentrated. The residue obtained therefrom was purified by silica gel chromatography (Hi-flash SI) (hexane:ethyl acetate=0:100 to 70:30) to give the title compound (5.82 g) having the following physical property value.

LCMS retention time (min): 0.92;
MS (ESI, Pos.): 283 (M+H)⁺;
¹H-NMR (CDCl₃): δ 8.83 (d, J=7.7 Hz, 1H).

Reference Example 3: 2-chloro-5-iodo-4-((propan-2-ylideneamino)oxy)nicotinonitrile

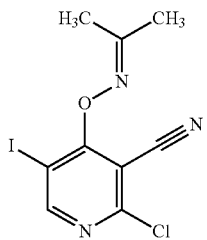

Sodium tert-butoxide (9.02 g) was added to the THF solution (100 mL) dissolving propan-2-one oxime (6.86 g) at room temperature, of which the mixture was stirred for 1 hour (hereinafter, this solution is referred to as an oxime solution). The oxime solution was added dropwise to THF solution (90 mL) dissolving the compound (26.5 g) produced in Reference Example 2 over 15 minutes under ice cooling. After the temperature of the reaction solution was raised to room temperature, it was further stirred for 30 minutes. A saturated ammonium chloride aqueous solution was added thereto, of which the mixture was extracted with ethyl acetate. The organic layer was washed with saturated saline, dried over sodium sulfate, and concentrated. The residue obtained therefrom was purified by silica gel column chromatography (Hi-flash SI) (hexane:ethyl acetate=70:30) to give the title compound (31.1 g) having the following physical property value.

LCMS retention time (min): 1.02;
¹H-NMR (CDCl₃): δ 8.67 (s, 1H), 2.21 (s, 3H), 2.13 (s, 3H).

Reference Example 4: 4-chloro-7-iodoisoxazolo[4,5-c]pyridin-3-amine

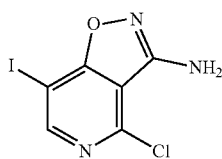 [SMILES: Nc1noc2c(I)cnc(Cl)c12]

5 mol/L hydrochloric acid (70 mL) was added to ethanol solution (70 mL) dissolving the compound (4.66 g) produced in Reference Example 3, of which the mixture was stirred at 70° C. for 1 hour. The solid formed in the reaction solution was collected by filtration to give the title compound (2.93 g) having the following physical property value.

LCMS retention time (min): 0.76;
MS (ESI, Pos.): 296 (M+H)⁺;
¹H-NMR (DMSO-d₆): δ 8.65 (s, 1H), 6.59 (s, 2H).

Reference Example 5: 4-bromo-7-iodoisoxazolo[4,5-c]pyridin-3-amine

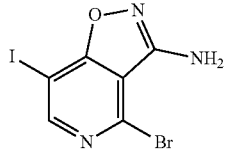 [SMILES: Nc1noc2c(I)cnc(Br)c12]

Bromotrimethylsilane (14.9 mL) was added to propionitrile solution (55.5 mL) dissolving the compound (5.55 g) produced in Reference Example 4 at room temperature, which was stirred at 105° C. for 3 hours. The reaction solution was cooled to room temperature, to which saturated aqueous sodium hydrogen carbonate solution was added, of which the mixture was extracted with ethyl acetate. The organic layer was washed with saturated saline, dried over sodium sulfate, and concentrated. To the residue obtained therefrom, hexane-ethyl acetate mixed solvent (4:1, 50 mL) was added, of which the mixture was stirred for 30 minutes. The precipitate therein was collected by filtration to give the title compound (4.78 g) having the following physical property value.

LCMS retention time (min): 0.81;
MS (ESI, Pos.): 340 (M+H)⁺;
¹H-NMR (CDCl₃): δ 8.64 (s, 1H), 6.48 (s, 2H).

Reference Example 6: 4-bromo-7-(1-(tetrahydro-2H-pyran-2-yl)-1H-pyrazol-4-yl)isoxazolo[4,5-c]pyridin-3-amine

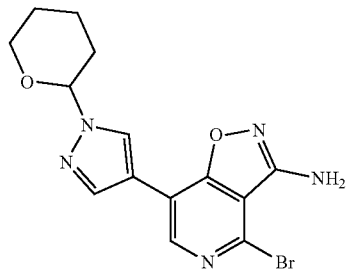 [SMILES: Nc1noc2c(-c3cnn(C4CCCCO4)c3)cnc(Br)c12]

Under nitrogen atmosphere, 1-(tetrahydro-2H-pyran-2-yl)-4-(4,4,5,5-tetramethyl-1,3,2-dioxaborolan-2-yl)-1H-pyrazole (1.73 g)(CAS No. 1003846-21-6), [1,1'-bis(diphenylphosphino)ferrocene]palladium(II) dichloride (484 mg) and 2 mol/L tripotassium phosphate aqueous solution (5.9 mL) was added to 1,4-dioxane solution (25 mL) dissolving the compound (2.01 g) prepared in Reference Example 5 (2.01 g), of which the mixture was stirred at 90° C. for 4 hours. The reaction solution was cooled to room temperature, diluted with ethyl acetate, and the insoluble material therein was filtered through a short silica gel pad. Water was added to the obtained filtrate, of which the mixture was extracted with ethyl acetate. The organic layer was washed with saturated brine, dried over sodium sulfate, and concentrated. To the residue obtained therefrom, methanol (10 mL) was added, of which the mixture was stirred for 30 minutes.

The precipitate therein was collected by filtration to give the title compound (1.50 g) having the following physical property value.

LCMS retention time (min): 0.80;
MS (ESI, Pos.): 364 (M+H)⁺.

Reference Example 7:
(5-bromo-4-fluoro-2-nitrophenyl)(methyl)sulfane

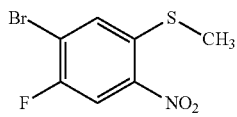

(1-bromo-2,5-fluoro-2-nitrophenyl)(methyl)sulfane (CAS No. 167415-27-2) (2.00 g) was dissolved in DMF solution (20 mL) and cooled to 0° C. An aqueous solution (4.2 mL) dissolving sodium thiomethoxide (707 mg) was added dropwise thereto, of which the mixture was stirred under ice cooling for 1.5 hours. The resulting precipitate therein was collected by filtration and dried to give the title compound (1.17 g) having the following physical property value.

LCMS retention time (min): 1.05;
$^1$H-NMR (CDCl$_3$): δ 8.06 (d, J=8.0 Hz, 1H), 7.52 (d, J=6.0 Hz, 1H), 2.52 (s, 3H).

Reference Example 8:
4-bromo-5-fluoro-2-(methylthio)aniline

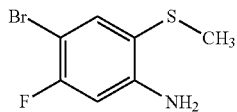

Iron powder (1.23 g) was added to acetic acid solution (12 mL) dissolving the compound (1.17 g) produced in Reference Example 7, of which the mixture was stirred at 90° C. for 1 hour. The reaction solution was cooled to room temperature, filtered through Celite (Registered trademark), and the obtained filtrate was concentrated. The residue obtained therefrom was purified by silica gel column chromatography (Hi-flash NH) (hexane:ethyl acetate=90:10 to 70:30) to give the title compound (1.06 g) having the following physical property value.

LCMS retention time (min): 1.01;
MS (ESI, Pos.): 236 (M+H)⁺;
$^1$H-NMR (CDCl$_3$): δ 7.52 (d, J=7.5 Hz, 1H), 6.50 (d, J=10.5 Hz, 1H), 4.45 (brs, 2H), 2.31 (s, 3H).

Reference Example 9:
4-bromo-5-fluoro-2-(methylsulfonyl)aniline

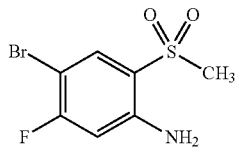

Under ice cooling, metachloroperbenzoic acid (containing about 30% water) (1.41 g) was added to dichloromethane solution (8.0 mL) dissolving the compound (500 mg) produced in Reference Example 8. After stirring it under ice-cooling for 1 hour, 10% sodium thiosulfate aqueous solution and saturated sodium hydrogencarbonate aqueous solution were added thereto to stop its reaction, of which the mixture was extracted with ethyl acetate. The organic layer was washed with saturated brine, dried over sodium sulfate, and concentrated. The residue obtained therefrom was purified by silica gel column chromatography (Hi-flash SI) (hexane:ethyl acetate=90:10 to 50:50) to give the title compound (487 mg) having the following physical property value.

LCMS retention time (min): 0.82;
MS (ESI, Pos.): 268 (M+H)⁺.

Reference Example 10:
1-(2-amino-5-bromo-4-fluorophenyl)ethan-1-one

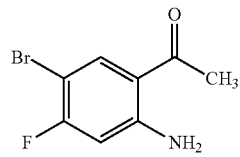

Under nitrogen atmosphere, 4-bromo-5-fluoro-2-iodoaniline (CAS No. 1219741-79-3) (810 mg), copper (I) iodide (48.8 mg), tributyl(1-ethoxyvinyl)tin (1.04 mL) and acetonitrile (10 mL) were mixed, of which the mixture solution was deaerated. Bis(triphenylphosphine)palladium (II) dichloride (180 mg) was added thereto, of which the mixture was stirred at 80° C. for 5 hours. The reaction solution was directly purified by silica gel column chromatography (Hi-flash SI) (hexane:ethyl acetate=100:0 to 70:30) to give the title compound (547 mg) having the following physical property value.

LCMS retention time (min): 0.91;
MS (ESI, Pos.): 232 (M+H)⁺.

Reference Example 11:
2-amino-5-bromo-N-ethyl-4-fluorobenzamide

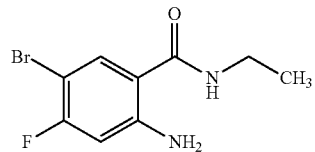

A mixture of 2-amino-5-bromo-4-fluorobenzoic acid (CAS No. 143945-65-7) (2.20 g), 1-[bis(dimethyl amino)methylene]-1H-1,2,3-triazolo[4,5-b]pyridinium 3-oxide-hexafluorophosphate (HATU: CAS No. 148893-10-1) (4.60 g), N, N-diisopropylethylamine (2.4 mL) and DMF (47 mL) was stirred at room temperature for 2 hours. To the reaction solution, saturated aqueous sodium hydrogen carbonate solution was added, of which the mixture was extracted with ethyl acetate. The organic layer was washed with saturated saline, dried over sodium sulfate, and concentrated. The residue obtained therefrom was purified by silica gel column chromatography (Hi-flash SI) (hexane:ethyl acetate=90:10 to 60:40) to give the title compound (2.08 g) having the following physical property value.

LCMS retention time (min): 0.84;
MS (ESI, Pos.): 261 (M+H)+.

Reference Example 12: 5-fluoro-2-(methyl sulfonyl)-4-(4,4,5,5-tetramethyl-1,3,2-dioxaborolan-2-yl) aniline

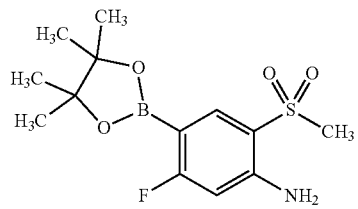

Under nitrogen atmosphere, 1,4-dioxane (8.0 mL) was added to a mixture of the compound (487 mg) produced in Reference Example 9, bis(pinacolato)diboron (922 mg) and potassium acetate (713 mg), of which the mixture was degassed. [1,1'-bis(diphenylphosphino)ferrocene]dichloropalladium dichloromethane complex (148 mg) was added thereto, of which the mixture was stirred at 90° C. overnight. The reaction mixture was filtered through Celite (registered trademark), and the obtained filtrate was concentrated. The residue obtained therefrom was purified by silica gel column chromatography (Hi-flash SI) (hexane:ethyl acetate=100:0 to 80:20) to give the title compound (342 mg) having the following physical property value.

LCMS retention time (min): 0.91;
MS (ESI, Pos.): 316 (M+H)+.

Reference Examples 12(1) to 12(5)

In place of 4-bromo-5-fluoro-2-(methylsulfonyl)aniline of Reference Example 9, the bromoaryl compound corresponding to it was used, and by subjecting it to the same operation as in Reference Example 12, the title compound having the following physical property value was obtained.

Reference Example 12(1): methyl 2-amino-4-fluoro-5-(4,4,5,5-tetramethyl-1,3,2-dioxaborolan-2-yl)benzoate

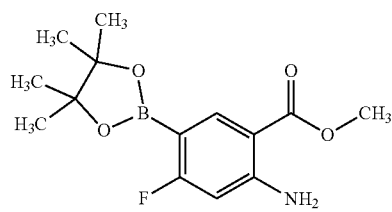

LCMS retention time (minutes): 1.04;
MS (ESI, Pos.): 296 (M+H)+.

Reference Example 12(2): 5-fluoro-2-(methylthio)-4-(4,4,5,5-tetramethyl-1,3,2-dioxaborolan-2-yl)aniline

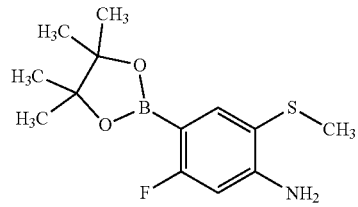

LCMS holding time (min): 1.06;
MS (ESI, Pos.): 284 (M+H)+.

Reference Example 12(3): 1-(2-amino-4-fluoro-5-(4,4,5,5-tetramethyl-1,3,2-dioxaborolan-2-yl)phenyl)ethan-1-one

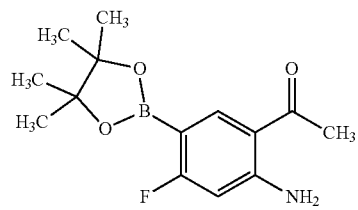 [SMILES: CC(=O)c1cc(B2OC(C)(C)C(C)(C)O2)c(F)cc1N]

LCMS retention time (min): 0.99;
MS (ESI, Pos.): 280 (M+H)+.

Reference Example 12(4): 2-amino-N-ethyl-4-fluoro-5-(4,4,5,5-tetramethyl-1,3,2-dioxaborolan-2-yl)benzamide

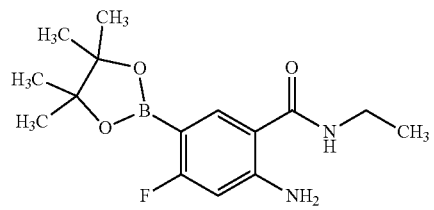 [SMILES: CCNC(=O)c1cc(B2OC(C)(C)C(C)(C)O2)c(F)cc1N]

LCMS retention time (minutes): 0.91;
MS (ESI, Pos.): 309 (M+H)+.

Reference Example 12(5): 2-amino-4-chloro-N-ethyl-5-(4,4,5,5-tetramethyl-1,3,2-dioxaborolan-2-yl)benzamide

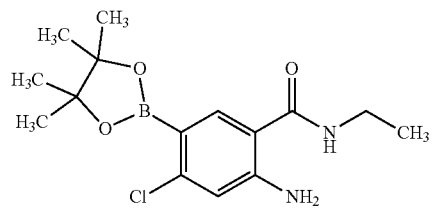 [SMILES: CCNC(=O)c1cc(B2OC(C)(C)C(C)(C)O2)c(Cl)cc1N]

LCMS holding time (minutes): 1.14;
MS (ESI, Pos.): 325 (M+H)+.

Reference Example 13: methyl 2-amino-5-(3-amino-7-(1-(tetrahydro-2H-pyran-2-yl)-1H-pyrazol-4-yl)isoxazolo[4,5-c]pyridin-4-yl)-4-fluorobenzoate

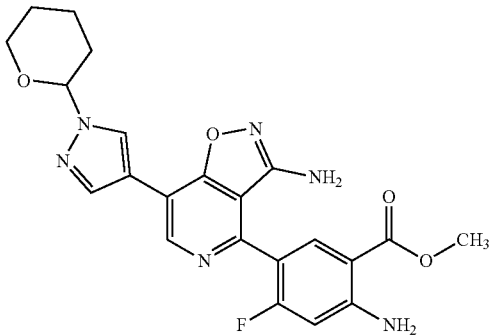 [SMILES: COC(=O)c1cc(-c2ncc(-c3cnn(C4CCCCO4)c3)c3onc(N)c23)c(F)cc1N]

Under nitrogen atmosphere, the boronic acid ester (89.1 mg) produced in Reference Example 12(1) and bis[di-tert-butyl(4-dimethylaminophenyl)phosphine]palladium (19.4 mg) and 2 mol/L sodium carbonate aqueous solution (0.27 mL) were added to DMF solution (1.37 mL) dissolving the compound (100 mg) produced in Reference Example 6, of which the mixture was stirred at 110° C. for 2 hours. After cooling it to room temperature, tap water was added thereto, of which the mixture was extracted with ethyl acetate. The organic layer was washed with saturated saline, dried over sodium sulfate, and concentrated. The residue obtained therefrom was purified by silica gel column chromatography (Hi-flash SI) (hexane:ethyl acetate=95:5 to 20:80) to give the title compound (110 mg) having the following physical property value.

LCMS retention time (min): 0.75;
MS (ESI, Pos.): 453 (M+H)+.

Example 1: methyl 2-amino-5-(3-amino-7-(1H-pyrazol-4-yl)isoxazolo[4,5-c]pyridin-4-yl)-4-fluorobenzoate

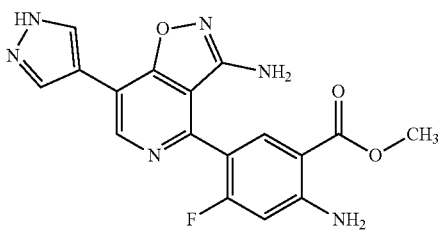 [SMILES: COC(=O)c1cc(-c2ncc(-c3cn[nH]c3)c3onc(N)c23)c(F)cc1N]

Trifluoroacetic acid (4.0 mL) was added to dichloromethane solution (4.0 mL) dissolving the compound (388 mg) produced in Reference Example 13, of which the mixture was stirred at 40° C. for 5 hours. To the reaction solution, saturated sodium hydrogen carbonate was added, of which the mixture was extracted with ethyl acetate. The organic layer was washed with saturated saline, dried over sodium sulfate, and concentrated. The residue obtained therefrom was purified by silica gel column chromatography (Hi-flash SI) (hexane:ethyl acetate=90:10 to 0:100) to give the compound of the present invention (19.6 mg) having the following physical property value.

LCMS retention time (min): 0.59;
MS (ESI, Pos.): 369 (M+H)+;
$^1$H-NMR (CD$_3$OD): δ 8.86 (s, 1H), 8.34 (s, 2H), 8.05 (d, J=8.5 Hz, 1H), 6.66 (d, J=12.5 Hz, 1H), 3.85 (s, 3H).

Example 2: 4-(4-amino-2-fluoro-5-methoxyphenyl)-7-(1H-pyrazol-4-yl)isoxazolo[4,5-c]pyridin-3-amine hydrochloride Under nitrogen atmosphere, 5-fluoro-2-methoxy-4-(4,4,5,5-tetramethyl-1,3,2-dioxaborolan-2-yl)aniline (CAS No. 1326283-60-6) (224 mg), bis[tri-tert-butylphosphine]palladium (65.9 mg), and 2 mol/L tripotassium phosphate aqueous solution (1.1 mL) were added to 1,4-dioxane solution (7.1 mL) dissolving the compound (235 mg) produced in Reference Example 6, of which the mixture was stirred at 110° C. for 3 hours. The reaction solution was directly purified by silica gel column chromatography (Hi-flash SI) (hexane:ethyl acetate=100:0 to 0:100) to give 4-(4-amino-2-fluoro-5-methoxyphenyl)-7-(1-(tetrahydro-2H-pyran-2-yl)-1H-pyrazol-4-yl)isoxazolo[4,5-c]pyridin-3-amine (108 mg) was obtained.

Hydrochloric acid (10% methanol solution, 2.0 mL) was added to THF solution (2.2 mL) dissolving this compound (108 mg), of which the mixture was stirred at room temperature for 2 hours. To the reaction solution, saturated sodium hydrogen carbonate was added, of which the mixture was extracted with ethyl acetate-methanol (9:1). The organic layer was washed with saturated saline, dried over sodium sulfate and concentrated. The residue obtained therefrom was purified by silica gel column chromatography (Hi-flash SI) (ethyl acetate:methanol=100:0 to 90:10). After concentration, the obtained residue was dissolved in methanol (5.0 mL), to which hydrochloric acid (10% methanol solution, 0.8 mL) was added, of which the mixture was concentrated. To the obtained residue, ethyl acetate (50 mL) was added, of which the mixture was stirred under heating reflux for 1 hour and then concentrated to give the compound of the present invention (87 mg) having the following physical property value.

LCMS retention time (min): 0.54;
MS (ESI, Pos.): 341 (M+H)+;
$^1$H-NMR (CD$_3$OD): δ 8.96 (s, 1H), 8.44 (s, 2H), 7.11 (d, J=6.5 Hz, 1H), 6.70 (d, J=12.0 Hz, 1H), 3.93 (s, 3H).

Example 3: 1-(2-amino-5-(3-amino-7-(1H-pyrazol-4-yl)isoxazolo[4,5-c]pyridin-4-yl)-4-fluorophenyl) ethan-1-one Under nitrogen atmosphere, the boronate ester (10.7 g) prepared in Reference Example 12 (3), butyl di-1-adamantylphosphine (984 mg), palladium acetate (308 mg), potassium iodide (456 mg) and 2 mol/L tripotassium phosphate aqueous solution (28 mL) were added to 1-methyl-2-pyrrolidone solution (hereinafter, abbreviated as NMP) (100 mL) dissolving the compound (10.0 g) produced in Reference Example 6, of which the mixture was stirred at 50 to 60° C. for 45 hours. After allowing the reaction solution to cool, insoluble matters therein were removed by filtration while washing with NMP. To the obtained filtrate, tap water (240 mL) was added little by little, of which the mixture was stirred for 40 minutes, and the precipitated solid therein was collected by filtration. The obtained solid was sequentially washed with acetonitrile (80 mL, twice) and methyl tert-butyl ether (80 mL, twice) by slurry washing, and then filtered and dried to give 1-(2-amino-5-(3-amino-7-(1-(tetrahydro-2H-pyran-2-yl)-1H-pyrazol-4-yl)isoxazolo[4,5-c]pyridin-4-yl)-4-fluorophenyl)ethan-1-one (8.52 g).

To this compound (6.00 g), methanol (24 mL) and methanesulfonic acid (3.96 g) were added, of which the mixture was stirred at 55° C. for 3 hours. The reaction mixture was allowed to cool to room temperature, and triethylamine (18 mL) was added thereto, of which the mixture was stirred at 55° C. for 2.5 hours. After allowing it to cool, the resulting precipitate was filtered to obtain a beige powder. To the powder, methanol (40 mL) was added, of which the mixture was washed by slurry washing at room temperature, filtered, and dried to obtain the compound of the present invention (4.50 g) having the following physical property value.

LCMS retention time (min): 0.56;
MS (ESI, Pos.): 353 (M+H)$^+$;
$^1$H-NMR (DMSO-d$_6$): δ 13.3 (s, 1H), 8.97 (s, 1H), 8.47 (s, 1H), 8.23 (s, 1H), 7.98 (d, J=8.5 Hz, 1H), 7.71 (brs, 2H), 6.67 (d, J=13.0 Hz, 1H), 5.73 (s, 2H), 2.52 (s, 3H).

Example 4: 4-(4-amino-2-fluoro-5-(methylthio)phenyl)-7-(1H-pyrazol-4-yl)isoxazolo[4,5-c]pyridin-3-amine hydrochloride To THF solution (1.5 mL) dissolving 4-(4-amino-2-fluoro-5-(methylthio)phenyl)-7-(1-(tetrahydro-2H-pyran-2-yl)-1H-pyrazol-4-yl)isoxazolo[4,5-c]pyridin-3-amine (76.6 mg) obtained by using the boronate ester produced in Reference Example 12(2) in place of methyl 2-amino-4-fluoro-5-(4,4,5,5-tetramethyl-1,3,2-dioxaborolan-2-yl)benzoate prepared in Reference Example 12(1) and subjecting it to the same operation as that in Reference Example 13, hydrochloric acid (10% methanol solution, 1.1 mL) was added at room temperature, of which the mixture was stirred for 1 hour. After the reaction, the resulting precipitate was collected by filtration to obtain the compound of the present invention (76.1 mg) having the following physical property value.

LCMS retention time (min): 0.60;
MS (ESI, Pos.): 357 (M+H)$^+$;
$^1$H-NMR (CD$_3$OD): δ 9.05 (s, 1H), 8.53 (s, 2H), 7.76 (d, J=8.0 Hz, 1H), 6.78 (d, J=13.0 Hz, 1H), 2.41 (s, 3H).

Examples 4(1) to 4(16)

In place of 4-(4-amino-2-fluoro-5-(methylthio)phenyl)-7-(1-(tetrahydro-2H-pyran-2-yl)-1H-pyrazol-4-yl)isoxazolo[4,5-c]pyridin-3-amine, the compound corresponding to it was prepared by a procedure similar to that described in Example 4, and then subjected to a procedure similar to that described in Example 4, following that, to give the compound of the present invention having the following physical property value.

Example 4(1): 4-(4-amino-3-methoxyphenyl)-7-(1H-pyrazol-4-yl)isoxazolo[4,5-c]pyridin-3-amine hydrochloride LCMS retention time (Min): 0.51;
MS (ESI, Pos.): 323 (M+H)$^+$;
$^1$H-NMR (CD$_3$OD): δ 8.99 (s, 1H), 8.49 (s, 2H), 7.52 (s, 1H), 7.42 (d, J=7.0 Hz, 1H), 7.30 (d, J=8.5 Hz, 1H), 4.05 (s, 3H).

Example 4(2): 4-(4-amino-2-fluoro-5-(methoxy-d$_3$)phenyl)-7-(1H-pyrazol-4-yl)isoxazolo[4,5-c]pyridine-3-amine hydrochloride LCMS retention time (min): 0.55;
MS (ESI, Pos.): 344 (M+H)$^+$;
$^1$H-NMR (CD$_3$OD): δ 9.09 (s, 1H), 8.56 (s, 2H), 7.29 (d, J=5.5, 1H), 6.95 (d, J=9.0 Hz, 1H).

Example 4(3): 4-(4-amino-2-fluoro-5-(methylsulfonyl)phenyl)-7-(1H-pyrazol-4-yl)isoxazolo[4,5-c]pyridin-3-amine hydrochloride LCMS retention time (min): 0.55;
MS (ESI, Pos.): 389 (M+H)$^+$;
$^1$H-NMR (CD$_3$OD): δ 9.10 (s, 1H), 8.50 (s, 2H), 8.12 (d, J=8.0, 1H), 6.90 (d, J=12.5 Hz, 1H), 3.17 (s, 3H).

Example 4(4): 4-(4-amino-2-fluoro-3-methoxyphenyl)-7-(1H-pyrazol-4-yl)isoxazolo[4,5-c]pyridin-3-amine hydrochloride HPLC retention time (min): 0.55;
MS (ESI, Pos.): 341 (M+H)$^+$;
$^1$H-NMR (CD$_3$OD): δ 9.04 (s, 1H), 8.49 (s, 2H), 7.24 (dd, J=8.5, 7.5, 1H), 6.84 (d, J=8.5 Hz, 1H), 3.99 (s, 3H).

Example 4(5): 2-amino-5-(3-amino-7-(1H-pyrazol-4-yl)isoxazolo[4,5-c]pyridin-4-yl)-4-fluorobenzamide hydrochloride LCMS retention time (min): 0.50;
MS (ESI, Pos.): 354 (M+H)$^+$;
$^1$H-NMR (DMSO-d$_6$): δ 9.03 (s, 1H), 8.40 (s, 2H), 7.92 (d, J=9.0, 1H), 7.79 (br s, 1H), 7.23 (br s, 1H), 6.64 (d, J=12.0 Hz, 1H), 5.98 (br s, 2H).

Example 4(6): ethyl 2-amino-5-(3-amino-7-(1H-pyrazol-4-yl)isoxazolo[4,5-c]pyridin-4-yl)-4-fluorobenzoate hydrochloride LCMS retention time (min): 0.69;
MS (ESI, Pos.): 383 (M+H)$^+$;
$^1$H-NMR (DMSO-d$_6$): δ 9.01 (s, 1H), 8.38 (s, 2H), 7.99 (d, J=8.5, 1H), 7.30 (br s, 1H), 6.72 (d, J=13.0 Hz, 1H), 5.83 (br s, 2H), 4.28 (q, J=7.0 Hz, 2H), 1.29 (t, J=7.0 Hz, 3H).

Example 4(7): 1-(2-amino-5-(3-amino-7-(1H-pyrazol-4-yl)isoxazolo[4,5-c]pyridin-4-yl)-4-fluorophenyl)propan-1-one hydrochloride LCMS retention time (min): 0.77;
MS (ESI, Pos.): 367 (M+H)$^+$;
$^1$H-NMR (CD$_3$OD): δ 8.94 (s, 1H), 8.38 (s, 2H), 8.20 (d, J=8.5 Hz, 1H), 6.66 (d, J=13.0 Hz, 1H), 2.94 (q, J=7.0 Hz, 2H), 1.09 (t, J=7.0 Hz, 3H).

Example 4(8): 2-amino-5-(3-amino-7-(1H-pyrazol-4-yl)isoxazolo[4,5-c]pyridin-4-yl)-N-ethyl-4-fluorobenzamide hydrochloride LCMS retention time (min): 0.70;
MS (ESI, Pos.): 382 (M+H)$^+$;
$^1$H-NMR (CD$_3$OD): δ 8.98 (s, 1H), 8.41 (s, 2H), 7.85 (d, J=8.0 Hz, 1H), 6.65 (d, J=13.0 Hz, 1H), 3.29 (q, J=7.0 Hz, 2H), 1.11 (t, J=7.0 Hz, 3H).

Example 4(9): 1-(2-amino-5-(3-amino-7-(1H-pyrazol-4-yl)isoxazolo[4,5-c]pyridin-4-yl)phenyl)ethan-1-one hydrochloride LCMS retention time (min): 0.67;
MS (ESI, Pos.): 335 (M+H)$^+$;

¹H-NMR (CD₃OD): δ 8.86 (s, 1H), 8.37 (s, 2H), 8.29 (d, J=2.0 Hz, 1H), 7.64 (dd, J=9.0, 2.0 Hz, 1H), 6.95 (d, J=9.0 Hz, 1H), 2.56 (s, 3H).

Example 4(10): methyl 2-amino-5-(3-amino-7-(1H-pyrazol-4-yl)isoxazolo[4,5-c]pyridin-4-yl)benzoate hydrochloride LCMS retention time (Min): 0.71;
MS (ESI, Pos.): 351 (M+H)⁺;
¹H-NMR (DMSO-d₆): δ 9.00 (s, 1H), 8.45 (s, 2H), 8.21 (s, 1H), 7.71 (d, J=9.0 Hz, 1H), 7.01 (d, J=9.0 Hz, 1H), 6.02 (br s, 2H), 3.84 (s, 3H).

Example 4(11): 2-amino-5-(3-amino-7-(1H-pyrazol-4-yl)isoxazolo[4,5-c]pyridin-4-yl)-N-propylbenzamide hydrochloride LCMS retention time (min): 0.70;
MS (ESI, Pos.): 378 (M+H)⁺;
¹H-NMR (CD₃OD): δ 8.86 (s, 1H), 8.38 (s, 2H), 7.95 (d, J=2.0 Hz, 1H), 7.60 (dd, J=8.5, 2.0 Hz, 1H), 6.94 (d, J=8.5 Hz, 1H), 3.26-3.13 (m, 2H), 1.54 (q, J=7.0 Hz, 2H), 0.90 (t, J=7.0 Hz, 3H).

Example 4(12): 1-(2-amino-5-(3-amino-7-(1H-pyrazol-4-yl)isoxazolo[4,5-c]pyridin-4-yl)-4-fluorophenyl)butan-1-one hydrochloride LCMS retention time (min): 0.90;
MS (ESI, Pos.): 381 (M+H)⁺;
¹H-NMR (CD₃OD): δ 8.94 (s, 1H), 8.37 (s, 2H), 8.20 (d, J=8.0 Hz, 1H), 6.65 (d, J=13.0 Hz, 1H), 2.88 (t, J=7.0 Hz, 2H), 1.65 (q, J=7.5 Hz, 2H), 0.90 (t, J=7.5 Hz, 3H).

Example 4(13): 1-(2-amino-5-(3-amino-7-(1H-pyrazol-4-yl)isoxazolo[4,5-c]pyridin-4-yl)phenyl)butan-1-one hydrochloride LCMS retention time (min): 0.87;
MS (ESI, Pos.): 363 (M+H)⁺;
¹H-NMR (CD₃OD): δ 8.86 (s, 1H), 8.38 (s, 2H), 8.33 (d, J=2.0 Hz, 1H), 7.63 (dd, J=9.0, 2.0 Hz, 1H), 6.96 (d, J=9.0 Hz, 1H), 2.96 (t, J=7.5 Hz, 2H), 1.70-1.64 (m, 2H), 0.92 (t, J=7.0 Hz, 3H).

Example 4(14): 2-hydroxyethyl 2-amino-5-(3-amino-7-(1H-pyrazol-4-yl)isoxazolo[4,5-c]pyridin-4-yl)-4-fluorobenzoate hydrochloride LCMS retention time (min): 0.76;
MS (ESI, Pos.): 399 (M+H)⁺;
¹H-NMR (CD₃OD): δ 8.97 (s, 1H), 8.39 (s, 2H), 8.30 (d, J=8.5 Hz, 1H), 6.69 (d, J=3.0 Hz, 1H), 4.26 (t, J=5.0 Hz, 2H), 3.74 (t, J=5.0 Hz, 2H).

Example 4(15): 2-amino-5-(3-amino-7-(1H-pyrazol-4-yl)isoxazolo[4,5-c]pyridin-4-yl)-N-methylbenzamide hydrochloride LCMS retention time (min): 0.69;
MS (ESI, Pos.): 350 (M+H)⁺;
¹H-NMR (DMSO-d₆): δ 9.04 (s, 1H), 8.56 (d, J=4.5 Hz, 1H), 8.52 (s, 2H), 8.18 (d, J=2.0 Hz, 1H), 7.64 (dd, J=8.5, 2.0 Hz, 1H), 6.94 (d, J=8.5 Hz, 1H), 6.22 (s, 2H), 2.78 (d, J=4.5 Hz, 3H).

Example 4(16): 4-(4-amino-2-chloro-5-(methylthio)phenyl)-7-(1H-pyrazol-4-yl)isoxazolo[4,5-c]pyridin-3-amine hydrochloride LCMS retention time (min): 0.63;
MS (ESI, Pos.): 373 (M+H)⁺;
¹H-NMR (DMSO-d₆): δ 9.08 (s, 1H), 8.43 (s, 2H), 7.40 (s, 1H), 6.93 (s, 1H), 2.37 (s, 3H).

Examples 4(17) to 4(24)

In place of 4-(4-amino-2-fluoro-5-(methylthio)phenyl)-7-(1-(tetrahydro-2H-pyran-2-yl)-1H-pyrazol-4-yl)isoxazolo[4,5-c]pyridin-3-amine, the compound corresponding to it was prepared by a procedure similar to that described in Example 4, and purified by reverse phase HPLC (used column: YMC Triart C18 (30 mm×75 mm); mobile phase: 0.1% TFA/water/acetonitrile=95:5 to 60:40) to obtain the compound of the present invention having the following physical property value.

Example 4(17): 2-amino-5-(3-amino-7-(1H-pyrazol-4-yl)isoxazolo[4,5-c]pyridin-4-yl)-4-fluoro-N-methylbenzamide trifluoroacetate LCMS retention time (min): 0.66;
MS (ESI, Pos.): 368 (M+H)⁺;
¹H-NMR (DMSO-d₆): δ (rotamer mixture) 8.98 (s, 1H), 8.35 (s, 2H), 8.27-8.21 (m, 1H), 7.76 (d, J=8.5 Hz, 1H), 6.61 (d, J=12.5 Hz, 1H), 5.69 (br s, 2H), 2.71 (s, 1.5H), 2.69 (s, 1.5H).

Example 4(18): 4-(4-amino-5-(ethylthio)-2-fluorophenyl)-7-(1H-pyrazol-4-yl)isoxazolo[4,5-c]pyridin-3-amine trifluoroacetate LCMS retention time (min): 0.64;
MS (ESI, Pos.): 371 (M+H)⁺;
¹H-NMR (CD₃OD): δ 8.97 (s, 1H), 8.43 (s, 2H), 7.69 (d, J=8.0 Hz, 1H), 6.73 (d, J=12.5 Hz, 1H), 2.81 (q, J=7.0 Hz, 2H), 1.25 (t, J=7.0 Hz, 3H).

Example 4(19): 2-amino-5-(3-amino-7-(1H-pyrazol-4-yl)isoxazolo[4,5-c]pyridin-4-yl)-4-fluoro-N-propylbenzamide trifluoroacetate LCMS retention time (min): 0.84;
MS (ESI, Pos.): 396 (M+H)⁺;
¹H-NMR (CD₃OD): δ 8.82 (s, 1H), 8.31 (s, 2H), 7.67 (d, J=8.0 Hz, 1H), 7.56 (d, J=12.5 Hz, 1H), 3.26-3.13 (m, 2H), 1.53-1.48 (m, 2H), 0.86 (t, J=7.0 Hz, 3H).

Example 4(20): 2-amino-5-(3-amino-7-(1H-pyrazol-4-yl)isoxazolo[4,5-c]pyridin-4-yl)benzamide trifluoroacetate LCMS retention Time (min): 0.67;
MS (ESI, Pos.): 336 (M+H)⁺;
¹H-NMR (CD₃OD): δ 8.79 (s, 1H), 8.29 (s, 2H), 7.95 (d, J=2.0 Hz, 1H), 7.55 (dd, J=8.5, 2.0 Hz, 1H), 6.88 (d, J=8.5 Hz, 1H).

Example 4(21): 2-amino-5-(3-amino-7-(1H-pyrazol-4-yl)isoxazolo[4,5-c]pyridin-4-yl)-N-ethylbenzamide trifluoroacetate LCMS retention time (min): 0.55;
MS (ESI, Pos.): 364 (M+H)⁺;

$^1$H-NMR (DMSO-d$_6$): δ 8.96 (s, 1H), 8.37 (s, 2H), 8.30 (t, J=6.0 Hz, 1H), 7.96 (d, J=2.5 Hz, 1H), 7.57 (dd, J=11.5, 2.5 Hz, 1H), 6.88 (d, J=11.5 Hz, 1H), 5.84 (brs, 2H), 3.25 (qd, J=9.0, 6.0 Hz, 2H), 1.10 (t, J=9.0 Hz, 3H).

Example 4(22): 1-(2-amino-5-(3-amino-7-(1H-pyrazol-4-yl)isoxazolo[4,5-c]pyridin-4-yl)phenyl)propan-1-one trifluoroacetate HPLC retention time (min): 0.62;
MS (ESI, Pos.): 349 (M+H)$^+$;
$^1$H-NMR (DMSO-d$_6$): δ 8.97 (s, 1H), 8.37 (s, 2H), 8.33 (s, 1H), 8.25 (d, J=2.0 Hz, 1H), 7.76 (dd, J=9.0, 2.0 Hz, 1H), 6.96 (d, J=9.0 Hz, 1H), 6.46 (br s, 2H), 5.94 (brs, 2H), 3.06 (q, J=7.0 Hz, 2H), 1.10 (t, J=7.0 Hz, 3H).

Example 4(23): 2-amino-5-(3-amino-7-(1H-pyrazol-4-yl)isoxazolo[4,5-c]pyridin-4-yl)-4-chloro-N-ethyl-benzamide trifluoroacetate LCMS retention time (min): 0.59;
MS (ESI, Pos.): 398 (M+H)$^+$;
$^1$H-NMR (DMSO-d$_6$): δ 9.00 (s, 1H), 8.38 (s, 2H), 8.32 (t, J=6.5 Hz, 1H), 7.71 (s, 1H), 6.95 (s, 1H), 5.54 (brs, 2H), 3.23 (qd, J=10.0, 6.5 Hz, 2H), 1.08 (t, J=10.0 Hz, 3H).

Example 4(24): 4-(2-fluoro-5-methoxy-4-nitrophenyl)-7-(1H-pyrazol-4-yl)isoxazolo[4,5-c]pyridin-3-amine trifluoroacetate LCMS retention time (min): 0.92;
MS (ESI, Pos.): 371 (M+H)$^+$.

Example 4 (25): 4-(4-amino-2-fluoro-5-(trifluoromethyl)phenyl)-7-(1H-pyrazol-4-yl)isoxazolo[4,5-c]pyridine-3-amine In place of 4-(4-amino-2-fluoro-5-(methylthio)phenyl)-7-(1-(tetrahydro-2H-pyran-2-yl)-1H-pyrazol-4-yl)isoxazolo[4,5-c]pyridin-3-amine, the compound corresponding to it was prepared by a procedure similar to that described in Example 4, and purified by reverse phase HPLC (column used: Xtimate C18 (25 mm×150 mm); mobile phase: 0.225% formic acid/water/acetonitrile=75:25 to 45:55) to obtain the compound of the present invention having the following physical property value.
LCMS retention time (min): 0.90;
MS (ESI, Pos.): 379 (M+H)$^+$;
$^1$H-NMR (DMSO-d$_6$): δ 8.93 (s, 1H), 8.39 (s, 2H), 7.69 (d, J=7.5 Hz, 1H), 6.78 (d, J=12.5 Hz, 1H).

Example 5: 4-(4-amino-2-fluoro-5-(methylsulfinyl)phenyl)-7-(1H-pyrazol-4-yl)isoxazolo[4,5-c]pyridin-3-amine trifluoroacetate The compound (17.2 mg) prepared in Example 4, sodium perborate tetrahydrate (6.16 mg), acetic acid (0.5 mL) and methanol (0.2 mL) were mixed, of which the mixture was stirred at 50° C. for 6 hours. The reaction solution was purified by reverse phase HPLC (used column: YMC Triart C18 (30 mm×75 mm); mobile phase: 0.1% TFA/water/acetonitrile=95:5 to 60:40) to obtain the compound of the present invention (5.0 mg) having the following physical property value.
LCMS retention time (min): 0.50;
MS (ESI, Pos.): 373 (M+H)$^+$;
$^1$H-NMR (DMSO-d$_6$): δ 8.99 (s, 1H), 8.37 (s, 2H), 7.56 (d, J=8.0 Hz, 1H), 6.66 (d, J=12.5 Hz, 1H), 2.79 (s, 3H).

Example 6: 2-amino-5-(3-amino-7-(1H-pyrazol-4-yl)isoxazolo[4,5-c]pyridin-4-yl)-4-fluorobenzoic acid THF (0.2 mL) and methanol (0.1 mL) were added to the compound (20 mg) produced in Example 1, and 2.0 mol/L sodium hydroxide aqueous solution (81 μL) was added dropwise thereto at room temperature, of which the mixture was stirred for 3 hours. The reaction solution was neutralized and purified by reverse phase HPLC (used column: YMC Triart C18 (30 mm×75 mm); mobile phase:0.1% TFA/water/acetonitrile=95:5 to 60:40) to obtain the compound of the present invention (12.1 mg) having physical property value.
LCMS retention time (min): 0.53;
MS (ESI, Pos.): 355 (M+H)$^+$;
$^1$H-NMR (DMSO-d$_6$): δ 8.97 (s, 1H), 8.35 (s, 2H), 7.93 (d, J=8.5 Hz, 1H), 7.23 (br s, 1H), 6.67 (d, J=12.5 Hz, 1H), 5.72 (br s, 2H).

Example 7: 4-(4-amino-2-fluoro-5-methoxyphenyl)-7-(3-methyl-1H-pyrazol-4-yl)isoxazolo[4,5-c]pyridin-3-amine trifluoroacetate In place of 1-(tetrahydro-2H-pyran-2-yl)-4-(4,4,5,5-tetramethyl-1,3,2-dioxaborolan-2-yl)-1H-pyrazole, (1-(tert-butoxy carbonyl)-3-methyl-1H-pyrazol-4-yl)boronic acid was subjected to the same operations as those in Reference Example 6→Reference Example 13→Example 2, to obtain the compound of the present invention having the following physical property value.
LCMS retention time (min): 0.56;
MS (ESI, Pos.): 355 (M+H)$^+$.

Example 8: 1-(2-amino-5-(3-amino-7-(1H-pyrazol-4-yl)isoxazolo[4,5-c]pyridin-4-yl)-4-hydroxyphenyl)ethan-1-one trifluoroacetate To 1,3-dimethyl-2-imidazolidinone solution (3 mL) dissolving 1-(2-amino-5-(3-amino-7-(1-(tetrahydro-2H-pyran-2-yl)-1H-pyrazol-4-yl)isoxazolo[4,5-c]pyridin-4-yl)-4-fluorophenyl)ethan-1-one (150 mg) prepared in the processes described in Example 3, acetohydroxamic acid (258 mg) and potassium carbonate (618 mg) were added, of which the mixture was stirred at 80° C. for 5 hours. After cooling it to room temperature, tap water (15 mL) was added thereto, of which the mixture was extracted with ethyl acetate (20 mL), washed with saturated saline, and then concentrated. The residue obtained therefrom was purified by silica gel column chromatography (Hi-flash NH) (ethyl acetate:methanol=100:0 to 50:50), to obtain 1-(2-amino-5-(3-amino-7-(1-(tetrahydro-2H-pyran-2-yl)-1H-pyrazol-4-yl)isoxazolo[4,5-c]pyridin-4-yl)-4-hydroxyphenyl)ethan-1-one (50 mg).
To this compound (50 mg), methanol (2.0 mL) and methanesulfonic acid (34 mg) were added, of which the mixture was stirred at room temperature for 64 hours. The precipitate generated by the reaction was collected by filtration, dissolved in dimethyl sulfoxide and purified by reverse phase HPLC (used column: YMC Triart C18 (30 mm×75 mm); mobile phase: 0.1% TFA/water/acetonitrile=95:5 to 60:40) to obtain the compound of the present invention (23.1 mg) having the following physical property value.
LCMS retention time (min): 0.55;
MS (ESI, Pos.): 351 (M+H)$^+$.

Reference Example 14: 5-bromo-2-chloro-3-fluoroisonicotinonitrile

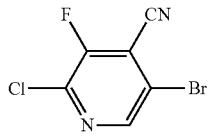 [SMILES: N#Cc1c(Br)cnc(Cl)c1F]

In place of 2-chloro-4-fluoro-5-iodopyridine, 5-bromo-2-chloro-3-fluoropyridine (CAS No. 831203-13-5) was subjected to the similar operations as those in Reference Example 1→Reference Example 2, to obtain the title compound having the following physical property value.

$^1$H-NMR (DMSO-d$_6$): δ 8.81 (s, 1H).

Reference Example 15: 5-(4-amino-2-fluoro-5-methoxyphenyl)-2-chloro-3-fluoroisonicotinonitrile

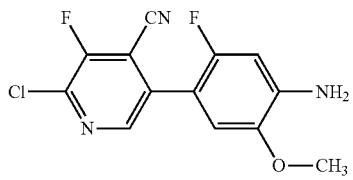 [SMILES: COc1cc(-c2cnc(Cl)c(F)c2C#N)c(F)cc1N]

Under argon atmosphere, 5-fluoro-2-methoxy-4-(4,4,5,5-tetramethyl-1,3,2-dioxaborolan-2-yl)aniline (CAS No. 1326283-60-6)(70.0 mg), [1,1'-bis(diphenylphosphino)ferrocene]palladium(II) dichloride (19.0 mg) and 2 mol/L tripotassium phosphate aqueous solution (0.40 mL) were added to 1,4-dioxane solution (2.0 mL) dissolving the compound (61.0 mg) prepared in Reference Example 14, of which the mixture was stirred at 90° C. for 3 hours. After allowing it to cool, to the reaction solution, water was added, of which the mixture was extracted with ethyl acetate. The organic layer was washed with saturated brine, dried over sodium sulfate, and concentrated. The residue obtained therefrom was purified by silica gel column chromatography (Hi-flash SI) (hexane:ethyl acetate=100:0 to 30:70) to obtain the title compound (45.0 mg) having the following physical property value. MS (ESI, Pos.): 296 (M+H)$^+$;

$^1$H-NMR (CDCl$_3$): δ 8.41 (s, 1H), 6.76 (d, J=6.5 Hz, 1H), 6.55 (d, J=11.5 Hz, 1H), 4.25 (s, 2H), 3.88 (s, 3H).

Reference Example 16: 5-(4-amino-2-fluoro-5-methoxyphenyl)-3-fluoro-2-(1-(tetrahydro-2H-pyran-2-yl)-1H-pyrazol-4-yl)isonicotinonitrile

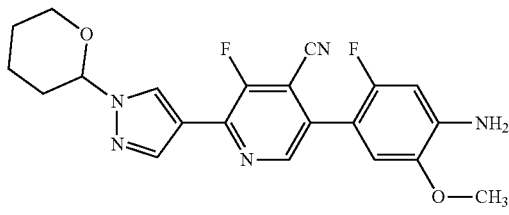 [SMILES: COc1cc(-c2cnc(-c3cnn(C4CCCCO4)c3)c(F)c2C#N)c(F)cc1N]

Under argon atmosphere, 4-(5,5-dimethyl-1,3,2-dioxaborinan-2-yl)-1-(tetrahydro-2H-pyran-2-yl)-1H-pyrazole (CAS No. 1072944-26-3)(40.0 mg), [1,1'-bis(diphenylphosphino)ferrocene]palladium(II) dichloride (11.0 mg) and 2 mol/L tripotassium phosphate aqueous solution (0.20 mL) were added to 1,4-dioxane solution (2.0 mL) dissolving the compound (45.0 mg) produced in Reference Example 15, of which the mixture was stirred at 110° C. for 6 hours. After allowing it to cool, to the reaction solution, water was added, of which the mixture was extracted with ethyl acetate. The organic layer was washed with saturated brine, dried over sodium sulfate, and concentrated. The residue obtained therefrom was purified by silica gel column chromatography (Hi-flash SI) (hexane:ethyl acetate=100:0 to 15:85) to obtain the title compound (30.0 mg) having the following physical property value. MS (ESI, Pos.): 412 (M+H)$^+$;

$^1$H-NMR (CDCl$_3$): δ 8.57 (dd, J=1.5, 0.5 Hz, 1H), 8.30 (d, J=2.0 Hz, 1H), 8.23 (d, J=1.0 Hz, 1H), 6.81 (d, J=6.5 Hz, 1H), 6.56 (d, J=11.0 Hz, 1H), 5.49-5.44 (m, 1H), 4.19 (s, 2H), 4.13-4.07 (m, 1H), 3.89 (s, 3H), 3.79-3.71 (m, 1H), 2.17-2.05 (m, 3H), 1.80-1.62 (m, 3H).

Reference Example 17: 4-(4-amino-2-fluoro-5-methoxyphenyl)-7-(1-(tetrahydro-2H-pyran-2-yl)-1H-pyrazol-4-yl)isoxazolo[5,4-c]pyridin-3-amine

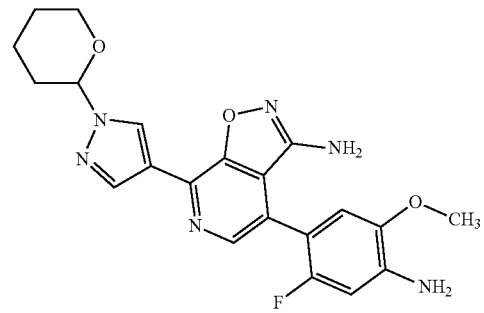 [SMILES: COc1cc(-c2cnc(-c3cnn(C4CCCCO4)c3)c3onc(N)c23)c(F)cc1N]

Under nitrogen atmosphere, potassium tert-butoxide (89.0 mg) was added to DMF solution (1.0 mL) dissolving acetohydroxamic acid (59 mg) at room temperature, of which the mixture was stirred for 30 minutes. To this mixed solution, DMF solution (2.0 mL) dissolving the compound (65 mg) produced in Reference Example 16 was added dropwise, of which the mixture was stirred at room temperature for 16 hours. To the reaction solution, water was added, of which the mixture was extracted with ethyl acetate. The organic layer was washed with saturated brine, dried over sodium sulfate, and concentrated. The residue obtained therefrom was purified by silica gel column chromatography (Hi-flash SI) (hexane:ethyl acetate=100:0 to 15:85) to give the title compound (22.0 mg) having the following physical property value.

MS (ESI, Pos.): 425 (M+H)$^+$;

$^1$H-NMR (CDCl$_3$): δ 8.56 (s, 1H), 8.42 (s, 1H), 8.31 (d, J=0.5 Hz, 1H), 6.76 (d, J=6.5 Hz, 1H), 6.59 (d, J=10.5 Hz, 1H), 5.52-5.47 (m, 1H), 4.14-4.08 (m, 1H), 4.33 (s, 2H), 4.15 (s, 2H), 3.87 (s, 3H), 3.79-3.70 (m, 1H), 2.16-2.04 (m, 3H), 1.75-1.50 (m, 3H).

Example 9: 4-(4-amino-2-fluoro-5-methoxyphenyl)-7-(1H-pyrazol-4-yl)isoxazolo[5,4-c]pyridin-3-amine hydrochloride

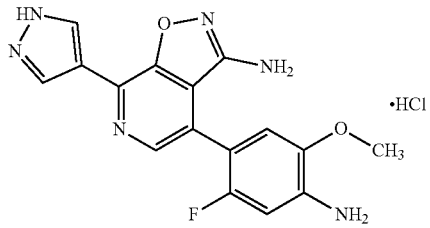 [SMILES: COc1cc(-c2cnc(-c3cn[nH]c3)c3onc(N)c23)c(F)cc1N ; Cl]

Hydrochloric acid (1.25 mol/L methanol solution) (0.64 mL) was added to THF solution (1.0 mL) dissolving the compound (20.0 mg) produced in Reference Example 17 at room temperature, of which the mixture was stirred for 3 hours. The reaction solution was concentrated to give the compound of the present invention (5.8 mg) having the following physical property value.

LCMS retention time (min): 0.66;

MS (ESI, Pos.): 341 (M+H)$^+$;

$^1$H-NMR (CD$_3$OD): δ 8.45 (s, 2H), 8.24 (d, J=1.0) Hz, 1H), 6.92 (d, J=7.0 Hz, 1H), 6.70 (d, J=11.5 Hz, 1H), 3.89 (s, 3H).

Reference Example 18: methyl 2-amino-5-(3-amino-7-(1-(((di-tert-butoxyphosphoryl)oxy)methyl)-1H-pyrazol-4-yl)isoxazolo[4,5-c]pyridin-4-yl)-4-fluorobenzoate

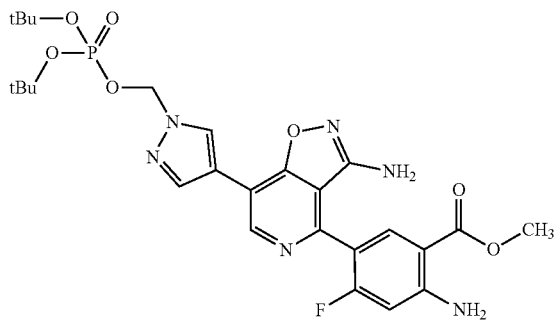 [SMILES: COC(=O)c1cc(-c2ncc(-c3cnn(COP(=O)(OC(C)(C)C)OC(C)(C)C)c3)c3onc(N)c23)c(F)cc1N]

Cesium carbonate (6.61 g) and di-tert-butyl-chloromethyl phosphate (1.41 mL) were added to DMF solution (41 mL) dissolving the compound (1.49 g) prepared in Example 1, of which the mixture was heated at 50° C. for 5 hours. To the reaction solution, saturated aqueous sodium hydrogen carbonate solution was added, of which the mixture was extracted with ethyl acetate. The organic layer was washed with saturated brine, dried over sodium sulfate and concentrated. The residue obtained therefrom was purified by silica gel column chromatography (Hi-flash SI) (hexane:ethyl acetate=90:10 to 0:100) to give the title compound (1.14 g) having the following physical property value.

LCMS retention time (min): 0.84;

MS (ESI, Pos.): 591 (M+H)$^+$.

Example 10: methyl 2-amino-5-(3-amino-7-(1-((phosphonooxy)methyl)-1H-pyrazol-4-yl)isoxazolo[4,5-c]pyridin-4-yl)-4-fluorobenzoate

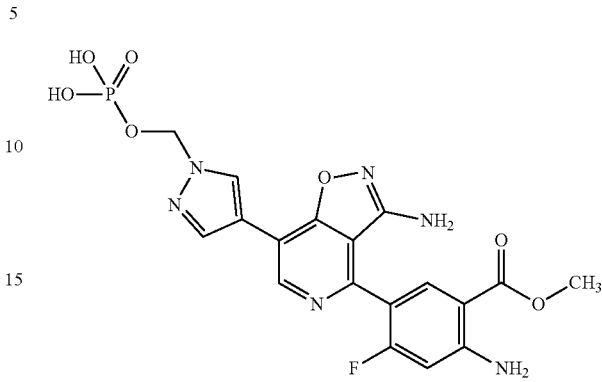

Purified water (6.8 mL) and acetic acid (13.5 mL) were added to the compound (1.09 g) produced in Reference Example 18, of which the mixture was stirred at 50° C. overnight. The precipitate deposited by the reaction was collected by filtration. The obtained filtrate was purified by reverse phase HPLC (used column: YMC Triart C18 (50 mm×100 mm); mobile phase: 0.1% TFA/water/acetonitrile=95:5 to 50:50) and concentrated to give The compound of the present invention (536 mg) having the following physical property value.

LCMS retention time (min): 0.51;

MS (ESI, Pos.): 479 (M+H)$^+$;

$^1$H-NMR (DMSO-d$_6$): δ 8.99 (s, 1H), 8.63 (s, 1H), 8.35 (s, 1H), 7.94 (d, J=8.5 Hz, 1H), 7.21 (brs, 2H), 6.71 (d, J=12.5 Hz, 1H), 5.91 (d, J=10.0 Hz, 2H), 5.75 (brs, 2H), 3.82 (s, 3H).

Examples 10(1) to 10(12)

In place of methyl 2-amino-5-(3-amino-7-(1H-pyrazol-4-yl)isoxazolo[4,5-c]pyridin-4-yl)-4-fluorobenzoate prepared in Example 1, the compound corresponding to it was subjected to the similar procedures as those of Reference Example 18→Example 10, to obtain the compound of the present invention having the following physical property value.

Example 10(1): (4-(4-(5-acetyl-4-amino-2-fluorophenyl)-3-aminoisoxazolo[4,5-c]pyridin-7-yl)-1H-pyrazol-1-yl)methyl dihydrogen phosphate

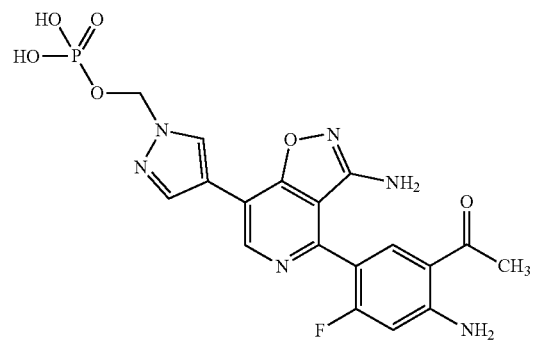 [SMILES: CC(=O)c1cc(-c2ncc(-c3cnn(COP(=O)(O)O)c3)c3onc(N)c23)c(F)cc1N]

Cesium carbonate (91.9 mg) and di-tert-butyl-chloromethylphosphate (20 μL) were added to DMF solution (0.5 mL) dissolving the compound (24 mg) produced in Example 3, of which the mixture was stirred at room temperature for 8 hours. To the reaction solution, tap water was added, of which the mixture was extracted with ethyl acetate. The organic layer was washed with saturated saline, dried over sodium sulfate and concentrated. To the obtained residue, dichloromethane (0.30 mL) and trifluoroacetic acid (0.12 mL) were added, of which the mixture was stirred at 40° C. overnight. The reaction solution was diluted with DMSO and purified by reverse phase HPLC (used column: YMC Triart C18 (30 mm×75 mm); mobile phase: 0.1% TFA/water/acetonitrile=95:5 to 60:40) to give the compound of the present invention (3.9 mg) having the following physical property value.

LCMS retention time (min): 0.50;

MS (ESI, Pos.): 463 (M+H)+;

$^1$H-NMR (DMSO-d$_6$): δ 8.98 (s, 1H), 8.61 (s, 1H), 8.33 (s, 1H), 7.97 (d, J=8.5 Hz, 1H), 7.70 (brs, 2H), 6.65 (d, J=13.0 Hz, 1H), 5.89 (d, J=10.0 Hz, 2H), 5.76 (brs, 2H), 2.51 (s, 3H).

Example 10(2): ethyl 2-amino-5-(3-amino-7-(1-((phosphonooxy)methyl)-1H-pyrazol-4-yl)isoxazolo[4,5-c]pyridin-4-yl)-4-fluorobenzoate

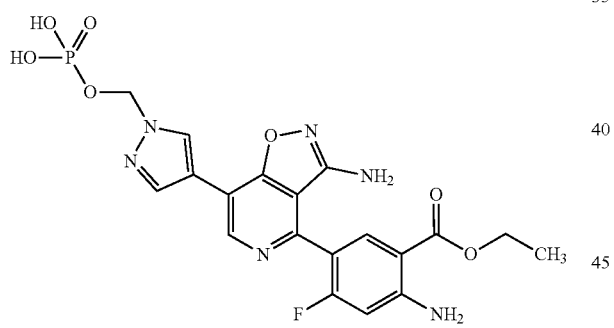

Cesium carbonate (128 mg) and di-tert-butyl-chloromethylphosphate (27 μL) were added to DMF solution (0.5 mL) dissolving the compound (36 mg) produced in Example 4(6), of which the mixture was stirred at room temperature overnight. To the reaction solution, tap water was added, of which the mixture was extracted with ethyl acetate. The organic layer was washed with saturated saline, dried over sodium sulfate and concentrated. To the obtained residue, dichloromethane (0.30 mL) and trifluoroacetic acid (0.18 mL) were added, of which the mixture was stirred at 40° C. for 3.5 hours. The reaction solution was diluted with DMSO and purified by reverse phase HPLC (used column: YMC Triart C18 (30 mm×75 mm); mobile phase: 0.1% TFA/water/acetonitrile=95:5 to 60:40) to give the compound of the present invention (15.0 mg) having the following physical property value.

LCMS retention time (min): 0.55;

MS (ESI, Pos.): 493 (M+H)+;

$^1$H-NMR (DMSO-d$_6$): δ 8.97 (s, 1H), 8.60 (s, 1H), 8.31 (s, 1H), 7.93 (d, J=8.5 Hz, 1H), 7.19 (br s, 2H), 6.67 (d, J=12.5 Hz, 1H), 5.87 (d, J=10.0 Hz, 2H), 5.73 (brs, 2H), 4.26 (q, J=7.0 Hz, 2H), 1.27 (t, J=7.0 Hz, 3H).

Example 10(3): (4-(3-amino-4-(4-amino-5-(ethyl carbamoyl)-2-fluorophenyl)isoxazolo[4,5-c]pyridin-7-yl)-1H-pyrazol-1-yl)methyl dihydrogen phosphate

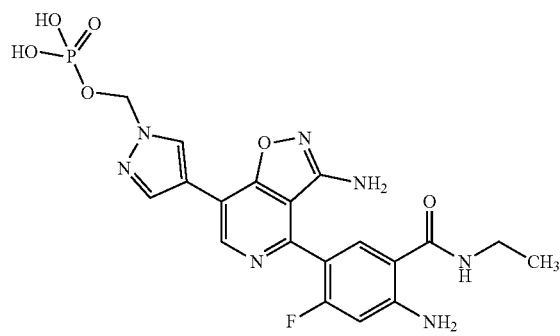 [SMILES: CCNC(=O)c1cc(-c2ncc(-c3cnn(COP(=O)(O)O)c3)c3onc(N)c23)c(F)cc1N]

LCMS retention time (min): 0.50;

MS (ESI, Pos.): 492 (M+H)+;

$^1$H-NMR (DMSO-d$_6$): δ 8.99 (s, 1H), 8.61 (s, 1H), 8.33 (s, 1H), 8.27 (t, J=5.5 Hz, 1H), 7.78 (d, J=8.5 Hz, 1H), 7.13 (brs, 2H), 6.60 (d, J=12.5 Hz, 1H), 5.88 (d, J=10.0 Hz, 2H), 5.65 (brs, 2H), 3.26-3.18 (m, 2H), 1.07 (t, J=7.0 Hz, 3H).

Example 10(4): (4-(3-amino-4-(4-amino-2-fluoro-5-(methylthio)phenyl)isoxazolo[4,5-c]pyridin-7-yl)-1H-pyrazol-1-yl)methyl dihydrogen phosphate

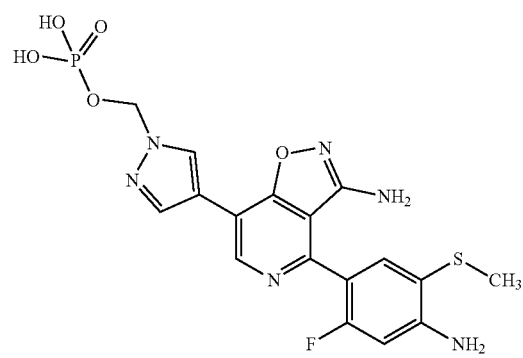 [SMILES: CSc1cc(-c2ncc(-c3cnn(COP(=O)(O)O)c3)c3onc(N)c23)c(F)cc1N]

LCMS holding time (minutes): 0.52;

MS (ESI, Pos.): 467 (M+H)+;

$^1$H-NMR (DMSO-d$_6$): δ 8.96 (s, 1H), 8.60 (s, 1H), 8.32 (s, 1H), 7.40 (d, J=8.5 Hz, 1H), 6.62 (d, J=12.5 Hz, 1H), 5.95 (brs, 2H), 5.88 (d, J=10.0 Hz, 2H), 5.64 (s, 2H), 2.32 (s, 3H).

Example 10(5): (4-(3-amino-4-(4-amino-2-fluoro-5-propionylphenyl)isoxazolo[4,5-c]pyridin-7-yl)-1H-pyrazol-1-yl)methyl dihydrogen phosphate

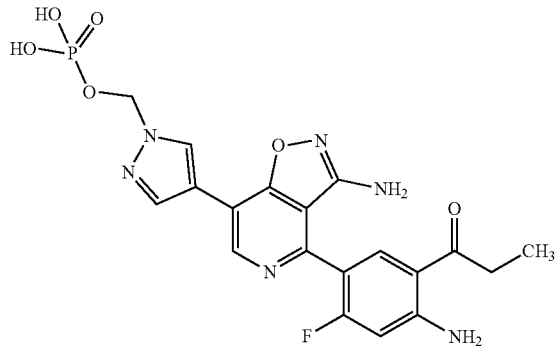 [SMILES: CCC(=O)c1cc(-c2ncc(-c3cnn(COP(=O)(O)O)c3)c3onc(N)c23)c(F)cc1N]

LCMS holding time (minutes): 0.53;
MS(ESI, Pos.): 477 (M+H)+;
1H-NMR (DMSO-d6): δ 8.98 (s, 1H), 8.61 (s, 1H), 8.33 (s, 1H), 7.99 (d, J=8.5 Hz, 1H), 7.70 (brs, 2H), 6.66 (d, J=12.0 Hz, 1H), 5.88 (d, J=10.0 Hz, 2H), 5.75 (brs, 2H), 2.96 (q, J=7.5 Hz, 2H), 1.05 (t, J=7.5 Hz, 3H).

Example 10(6): (4-(4-(3-acetyl-4-aminophenyl)-3-aminoisoxazolo[4,5-c]pyridin-7-yl)-1H-pyrazol-1-yl)methyl dihydrogen phosphate

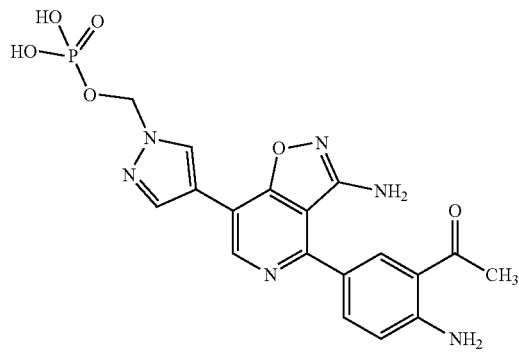 [SMILES: CC(=O)c1cc(-c2ncc(-c3cnn(COP(=O)(O)O)c3)c3onc(N)c23)ccc1N]

LCMS holding time (minutes): 0.48;
MS (ESI, Pos.): 445 (M+H)+;
1H-NMR (DMSO-d6): δ 8.95 (s, 1H), 8.58 (s, 1H), 8.31 (s, 1H), 8.19 (d, J=2.0 Hz, 1H), 7.77 (dd, J=8.5, 2.0 Hz, 1H), 7.58 (brs, 2H), 6.92 (d, J=8.5 Hz, 1H), 5.92-5.85 (m, 4H), 2.54 (s, 3H).

Example 10(7): (4-(3-amino-4-(4-amino-2-fluoro-5-(methylsulfonyl)phenyl)isoxazolo[4,5-c]pyridin-7-yl)-1H-pyrazol-1-yl)methyl dihydrogen phosphate

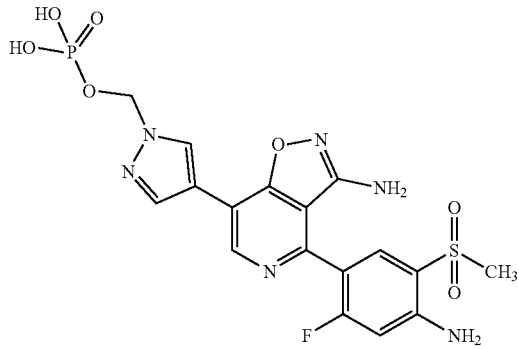 [SMILES: CS(=O)(=O)c1cc(-c2ncc(-c3cnn(COP(=O)(O)O)c3)c3onc(N)c23)c(F)cc1N]

LCMS holding time (minutes): 0.668;
MS(ESI, Pos.): 499 (M+H)+;
1H-NMR (DMSO-d6): δ 9.00 (s, 1H), 8.63 (s, 1H), 8.35 (s, 1H), 7.74 (d, J=8.0 Hz, 1H), 6.79 (d, J=12.0 Hz, 1H), 6.64 (brs, 2H), 5.91 (d, J=12.0 Hz, 2H), 5.83 (brs, 2H), 3.18 (s, 3H).

Example 10(8): acetate or acetic acid solvate of (4-(3-amino-4-(4-amino-5-(ethylcarbamoyl)-2-chlorophenyl)isoxazolo[4,5-c]pyridin-7-yl)-1H-pyrazol-1-yl)methyl dihydrogen phosphate

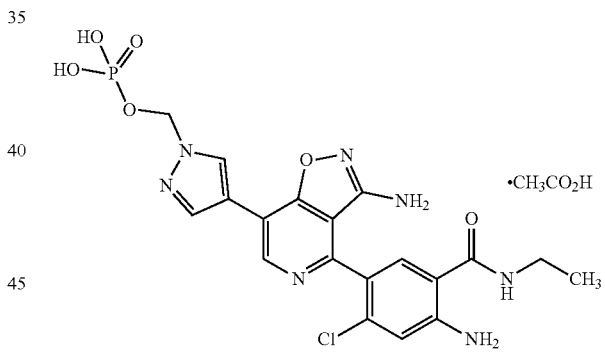

By subjecting the compound (421 mg) produced in Example 4 (23) to the same operation as in Reference Example 18, (4-(3-amino-4-(4-amino-2-chloro-5-(ethyl carbamoyl)phenyl)isoxazolo[4,5-c]pyridin-7-yl)-1H-pyrazol-1-yl)methyl di-tert-butyl phosphate (430 mg) was obtained. Acetic acid (19.3 mL) and purified water (3.4 mL) were added to this compound (379 mg), of which the mixture was stirred at 60° C. for 5 hours. The precipitate obtained therein was collected by filtration and dried to obtain the compound of the present invention (304 mg) having the following physical property value and being in the form of acetate or acetic acid solvate.
LCMS retention time (min): 0.706;
MS (ESI, Pos.): 508 (M+H)+;
1H-NMR (DMSO-d6): δ 9.01 (s, 1H), 8.64 (s, 1H), 8.36 (s, 1H), 8.33-8.29 (m, 1H), 7.70 (s, 1H), 7.01 (brs, 2H), 6.94 (s, 1H), 5.90 (d, J=10.0 Hz, 2H), 5.53 (brs, 2H), 3.24-3.18 (m, 2H), 1.91 (s, 3H), 1.07 (t, J=7.0 Hz, 3H).

Example 10(9): hydrate of (4-(4-(5-acetyl-4-amino-2-fluorophenyl)-3-aminoisoxazolo[4,5-c]pyridin-7-yl)-1H-pyrazol-1-yl)methyl dihydrogen phosphate By subjecting the compound (100 mg) produced in Example 3 to the same operation as in Reference Example 18, (4-(4-(5-acetyl-4-amino-2-fluorophenyl)-3-aminoisoxazolo[4,5-c]pyridin-7-yl)-1H-pyrazol-1-yl)methyl di-tert-butyl phosphate (112 mg) was obtained. Acetic acid (0.20 mL) and purified water (0.05 mL) were added to this compound (25 mg), of which the mixture was stirred at 60° C. overnight. The precipitate obtained therein was collected by filtration and dried to obtain the compound of the present invention (18.0 mg) of Example 10(1) having the following physical property value and being in a hydrate form. In addition, it was confirmed from the DSC and TG analysis on the compound of the present invention that it was a hydrate.

LCMS retention time (min): 0.50;
MS (ESI, Pos.): 463 (M+H)$^+$;
$^1$H-NMR (DMSO-d$_6$): δ 8.98 (s, 1H), 8.61 (s, 1H), 8.33 (s, 1H), 7.97 (d, J=8.5 Hz, 1H), 7.70 (brs, 2H), 6.65 (d, J=13.0 Hz, 1H), 5.89 (d, J=10.0 Hz, 2H), 5.76 (brs, 2H), 2.51 (s, 3H).

Example 10(10): (4-(4-(5-acetyl-4-amino-2-fluorophenyl)-3-aminoisoxazolo[4,5-c]pyridin-7-yl)-1H-pyrazol-1-yl)methyl monohydrogenphosphate monopotassium salt 0.25M aqueous potassium acetate solution (0.43 mL, 1 equivalent) was added to acetic acid solution (1.25 mL) dissolving the compound (50 mg) prepared in Example 10(1), of which the mixture was stirred at room temperature for 8 hours. The obtained suspension was collected by filtration and dried under reduced pressure to obtain the compound of the present invention (43.5 mg) having the following physical property value.

LCMS retention time (min): 0.49;
MS (ESI, Pos.): 463 (M+H)$^+$;
$^1$H-NMR (DMSO-d$_6$+CD$_3$OD): δ 8.94 (s, 1H), 8.60 (s, 1H), 8.21 (s, 1H), 7.99 (d, J=8.5 Hz, 1H), 7.70 (brs, 2H), 6.66 (d, J=13.0 Hz, 1H), 5.69 (d, J=9.5 Hz, 2H), 2.52 (s, 3H).

Example 10(11): trifluoroacetate or trifluoroacetic acid solvate of ethyl 2-amino-5-(3-amino-7-(1-((phosphonooxy)methyl)-1H-pyrazol-4-yl)isoxazolo[4,5-c]pyridin-4-yl)-4-fluorobenzoate Cesium carbonate (128 mg) and di-tert-butyl-chloromethyl phosphate (27 μL) were added to DMF solution (0.5 mL) dissolving the compound prepared in Example 4(6) (2.00 g), of which the mixture was stirred at room temperature overnight. To the reaction solution, tap water was added, of which the mixture was extracted with ethyl acetate. The organic layer was washed with saturated saline, dried over sodium sulfate and concentrated. The residue obtained therefrom was purified by silica gel column chromatography (Hi-flash SI) (hexane:ethyl acetate=90:10 to 0:100) to obtain ethyl 2-amino-5-(3-amino-7-(1-(((di-tert-butoxyphosphoryl)oxy)methyl)-1H-pyrazol-4-yl)isoxazolo[4,5-c]pyridin-4-yl)-4-fluorobenzoate (2.12 g). Purified water (10 mL), ethanol (10 mL) and trifluoroacetic acid (5.3 mL) were sequentially added thereto, of which the mixture was stirred at 40° C. After 2 hours, ethanol (5 mL) was added thereto, of which the mixture was cooled to room temperature. The precipitate obtained therein was collected by filtration with washing with ethanol and dried under reduced pressure to obtain the compound of the present invention (1.81 g) having the following physical property value.

LCMS retention time (min): 0.55;
MS (ESI, Pos.): 493 (M+H)$^+$;
$^1$H-NMR (DMSO-d$_6$): δ 9.02 (s, 1H), 8.65 (s, 1H), 8.36 (s, 1H), 7.98 (d, J=8.5 Hz, 1H), 7.32 (brs, 2H), 6.70 (d, J=12.5 Hz, 1H), 5.91 (d, J=10.0 Hz, 2H), 5.79 (brs, 2H), 4.28 (q, J=7.0 Hz, 2H), 1.29 (t, J=7.0 Hz, 3H).

Example 10(12): acetate or acetic acid solvate of ethyl 2-amino-5-(3-amino-7-(1-((phosphonooxy)methyl)-1H-pyrazol-4-yl)isoxazolo[4,5-c]pyridin-4-yl)-4-fluorobenzoate Purified water (30 mL) and acetic acid (20 mL) were added to the compound (2.13 g) produced in Example 10(2), of which the mixture was stirred at 60° C. for 4 hours. The solvent was distilled off under reduced pressure and diluted with ethanol (30 mL). The reaction solution was stirred overnight and collected by filtration to give the compound of the present invention (1.50 g) having the following physical property value.

LCMS retention time (min): 0.55;
MS (ESI, Pos.): 493 (M+H)$^+$;
$^1$H-NMR (DMSO-d$_6$): δ 8.99 (s, 1H), 8.62 (s, 1H), 8.34 (s, 1H), 7.96 (d, J=8.5 Hz, 1H), 7.21 (brs, 2H), 6.69 (d, J=13.0 Hz, 1H), 5.91 (d, J=10.0 Hz, 2H), 5.74 (brs, 2H), 4.27 (q, J=7.0 Hz, 2H), 1.92 (s, 3H), 1.29 (t, J=7.0 Hz, 3H).

Reference Example 19: 4-chloro-7-iodoisothiazolo[4,5-c]pyridin-3-amine

Under nitrogen atmosphere, dimethyl sulfoxide was added to sodium sulfide (138 mg), of which the mixture was stirred for 10 minutes, and then the compound (500 mg) produced in Reference Example 2 was added thereto, of which the mixture was stirred at room temperature for 30 minutes. After cooling it to 10° C., aqueous ammonia was added thereto, of which the mixture was stirred for 30 minutes. N-chlorosuccinimide (248 mg) was added thereto, of which the mixture was stirred for 30 minutes, and further N-chlorosuccinimide (472 mg) was further added thereto, of which the mixture was stirred for 30 minutes. Saturated aqueous sodium thiosulfate solution (5 mL) and tap water (15 mL) were added thereto, and the resulting precipitate was collected by filtration. The precipitate was dried at 50° C. for 1.5 hours, dissolved in ethyl acetate and washed with tap water. It was dried over sodium sulfate and concentrated to give the title compound (286 mg) having the following physical property value.

LCMS retention time (min): 0.88;
MS (ESI, Pos.): 312 (M+H)$^+$.

Reference Example 20: 4-bromo-7-iodoisothiazolo[4,5-c]pyridin-3-amine

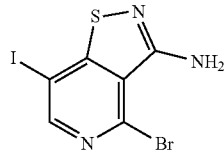

Under nitrogen atmosphere, propionitrile (2.4 mL) and bromotrimethylsilane (0.61 mL) were added to the compound (240 mg) produced in Reference Example 19, of which the mixture was stirred at 100° C. for 20 hours. After cooling it to 0° C., methyl tert-butyl ether (7.2 mL) was added thereto, of which the mixture was stirred for 1.5 hours. The resulting precipitate was collected by filtration to give the title compound (317 mg) having the following physical property value.

LCMS retention time (min): 0.91;
MS (ESI, Pos.): 356 (M+H)$^+$.

Reference Example 21: 4-bromo-7-(1-(tetrahydro-2H-pyran-2-yl)-1H-pyrazol-4-yl)isothiazolo[4,5-c]pyridin-3-amine

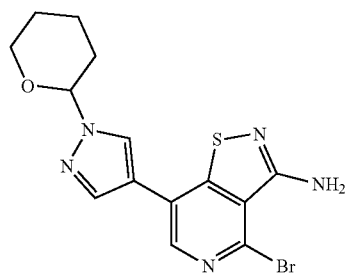 [SMILES: Nc1nsc2c(-c3cnn(C4CCCCO4)c3)cnc(Br)c12]

Under nitrogen atmosphere, to a mixture of the compound (384 mg) produced in Reference Example 20, 1-(tetrahydro-2H-pyran-2-yl)-4-(4,4,5,5-tetramethyl-1,3,2-dioxaborolan-2-yl)-1H-pyrazole (315 mg) and [1,1'-bis(diphenylphosphino)ferrocene]dichloropalladium dichloromethane complex (66 mg), 1,4-dioxane (4.6 mL) and 2 mol/L tripotassium phosphate aqueous solution (1.6 mL) were added, of which the mixture was stirred at 105° C. for 29 hours. After cooling it to room temperature, ethyl acetate and city water were added thereto, of which the mixture was filtered through Celite (trade name). The mixture was extracted with ethyl acetate and then concentrated. The residue obtained therefrom was purified by silica gel column chromatography (Hi-flash DIOL) (ethyl acetate:hexane=75:25 to 50:50) to give the title compound (75.7 mg) having the following physical property value.

LCMS retention time (min): 0.86;
MS (ESI, Pos.): 380 (M+H)$^+$.

Example 11: 1-(2-amino-5-(3-amino-7-(1H-pyrazol-4-yl)isothiazolo[4,5-c]pyridin-4-yl)-4-fluorophenyl)ethan-1-one trifluoroacetate

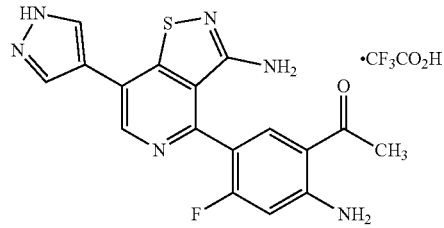 [SMILES: CC(=O)c1cc(-c2ncc(-c3cn[nH]c3)c3snc(N)c23)c(F)cc1N ; "·CF3CO2H"]

Under nitrogen atmosphere, the boronic acid ester (69 mg) produced in Reference Example 12(3) and butyl di-1-adamantylphosphine (8.9 mg), palladium acetate (2.8 mg), potassium iodide (2.7 mg) and 2 mol/L tripotassium phosphate aqueous solution (0.17 mL) were added to NMP solution (1.25 mL) dissolving the compound (75 mg) produced in Reference Example 21, of which the mixture was stirred at 80° C. for 18 hours. After allowing the reaction solution to cool, it was directly purified by silica gel column chromatography (Hi-flash DIOL) (ethyl acetate:hexane=80:20 to 50:50) to obtain 1-(2-amino-5-(3-amino-7-(1-(tetrahydro-2H-pyran-2-yl)-1H-pyrazol-4-yl)isothiazolo[4,5-c]pyridin-4-yl)-4-fluorophenyl)ethan-1-one (13 mg).

To this compound (13 mg), methanol (0.65 mL) and methanesulfonic acid (8.3 mg) were added, of which the mixture was stirred at room temperature for 3 hours. After allowed the reaction mixture to cool to room temperature, triethylamine (8.8 mg) was added thereto, of which the mixture was concentrated, and the residue obtained therefrom was purified by reverse-phase HPLC (used column: YMC Triart C18 (30 mm×75 mm); mobile phase: 0.1% TFA/water/acetonitrile=95:5 to 60:40) to give the compound of the present invention (3.0 mg) having the following physical property value.

LCMS retention time (min): 0.60;
MS (ESI, Pos.): 369 (M+H)$^+$;
$^1$H-NMR (DMSO-d$_6$): δ 8.83 (s, 1H), 8.32 (brs, 1H), 8.10 (brs, 1H), 7.94 (d, J=8.5 Hz, 1H), 7.69 (brs, 2H), 6.67 (d, J=13.0 Hz, 1H), 5.87 (s, 2H), 2.49 (s, 3H).

Pharmacological Example

Example 12: Effects on THP1-Dual Cells

THP1-Dual cells (Invivogen) were suspended in RPMI medium to prepare 2×10$^6$ cells/mL of cell suspension. 50 μL of the cell suspensions were dispensed into a 96-well plate, to which 50 μL of 6 to 20,000 nmol/L compound solutions were added. After adding the compound, the mixture was incubated at 37° C. for about 24 hours. After incubation, 10 μL of cell suspensions were collected from the respective wells, which were mixed with 50 μL of Quanti-luc (Invivogen). Then, the activation of the IRF (Interferon regulatory factor) pathway was measured by detecting luminescence using a microplate reader (Molecular Devices).

EC50 values of the compounds of the present invention shown in the respective Examples are shown below.

TABLE 1

| Example No. | EC50 (µmol/L) |
|---|---|
| 2 | 1.93 |
| 4 | 0.09 |
| 4(3) | 0.95 |
| 1 | 0.18 |
| 4(5) | 0.08 |
| 3 | 0.04 |
| 4(16) | 1.00 |
| 4(6) | 0.04 |
| 4(7) | 0.02 |
| 4(8) | 0.02 |
| 4(9) | 0.13 |
| 4(15) | 0.10 |

Example 13: Activity on THP1-Dual-STING KO Cells

STING gene homozygous deficient THP1-Dual cells (THP1-Dual-STING KO cells (Invivogen) were suspended in RPMI medium to prepare 2×10$^6$ cells/mL cell suspension. 50 µL of cell suspensions were dispensed into a 96-well plate, to which 50 µL of 6 to 20,000 nM compound solutions were further added, followed by incubation at 37° C. for about 24 hours. 10 µL of the cell suspensions were collected from the respective wells, which were mixed with 50 µL of Quanti-luc (Invivogen), and then the activity of the IRF pathway was measured by detecting luminescence using a microplate reader.

The compound of the present invention shown in Example 1 showed no IRF activating effect. Therefore, it was shown that the IRF activating effect of the compound of the present invention exemplified in Example 1 is based on the agonistic activity on STING by the compound of the present invention.

Example 14: Evaluation of IDO1 Inhibitory Activity

The evaluation of IDO1 inhibitory activity was carried out using the IDO1 Fluorogenic Inhibitor Screening Assay Kit (BPS Bioscience). Specifically, IDO1 Fluorogenic Reaction Solution was dissolved, of which 180 µL were added to each well. Then, 10 µL of compounds at the respective concentrations of 0.6, 2, 6, 20, 60 and 200 µmol/L were added thereto. Further, after adding 10 µL of IDO1 His-Tag solution thereto, of which the mixtures were incubated at room temperature for 1 hour, and then 20 µL of Fluorescence Solution was added thereto, of which the mixtures were incubated at 37° C. for 4 hours. After standing them at room temperature for 10 minutes, the fluorescence was measured using a microplate reader (excitation: 400 nm, emission: 510 nm).

The compound of the present invention shown in Example 1 did not show any IDO1 inhibitory activity.

Example 15: Evaluation of Inhibitory Activity Against Various Kinases

4 µmol/L of test substance solution (the compound of the present invention shown in Example 1) (at 4 times the final concentration) was prepared by dissolving it to the assay buffer (20 mmol/L HEPES, 0.01% Triton X-100, 1 mmol/L DTT, pH 7.5). 4 µmol/L of substrate/ATP/metal solution (at 4 times the final concentration) was prepared by dissolving them to the kit buffer (20 mmol/L HEPES, 0.01% Triton X-100, 5 mmol/L DTT, pH 7.5).

Various kinase solutions at twice the final concentration were prepared by dissolving them to the assay buffer. 5 µL of the test substance solution, 5 µL of the substrate/ATP/metal solution and 10 µL of the kinase solution were mixed in wells of a polypropylene 384-well plate, of which the mixture was reacted at room temperature for 1 to 5 hours. The reaction was stopped by adding 70 µL of the termination buffer (QuickScout Screening Assist MSA; Cama Biosciences). The substrate peptide and phosphorylated peptide in the reaction solution were separated and quantified by LabChip system (Perkin Elmer). The kinase reaction was evaluated by the product ratio (P/(P+S)) calculated from the peak height (S) of the substrate peptide and the peak height (P) of the phosphorylated peptide. The various kinases used for evaluation are as follows:
BTK, KDR, each subtype of PKCα to ι, each CDK of CDK2 to 9, FAK, TIE2, RAF1 and BRAF.

The compound of the present invention shown in Example 1 did not showed any significantly inhibit activities against any of the evaluated kinases.

Example 16: Evaluation of Anti-Tumor Effect in Tumor Model Bearing Subcutaneous Mouse Colon Cancer Cell Line MC38

Colon cancer cell line MC38 derived from C57/BL6 mice were subcutaneously transplanted to right flank of syngeneic mice (C57/BL6, female, 6 weeks old (Charles River Japan)) (herein, the day of transplantation was Day 0) to prepare tumor mice bearing subcutaneous MC38. Seven days after transplantation, tumor mice bearing subcutaneous MC38 were grouped based on tumor volume, and used as the Vehicle group (n=8) and the compound administration group (3 mg/kg, n=6) shown in Example 1. The changes in tumor volume were continuously measured until the 26 days after transplantation (Day 26). The tumor volume was calculated by the following formula:

[Tumor volume (mm$^3$)]=[major axis (mm)]×[minor axis (mm)]$^2$×0.5

FIG. 1 showed its results.
The compound represented in Example 1 almost completely suppressed the tumor growth at the dose of 3 mg/kg.

Example 17: Evaluation of Anti-Tumor Effect in Tumor Model Bearing Subcutaneous Mouse Colon Cancer Cell Line MC38

Colon cancer cell line MC38 derived from C57/BL6 mice were subcutaneously transplanted to right flank of syngeneic mice (C57/BL6, female, 6 weeks old (Charles River Japan)) (herein, the day of transplantation was Day 0) to prepare tumor mice bearing subcutaneous MC38. They were grouped based on tumor volume 7 or 8 days after transplantation, to which the Vehicle (n=8 or 6) and the respective compounds of Examples 10 and 10(1) to 10(6) (1, 1, 1, 10, 3, 1 and 1 mg/kg, n=8 or 6) were administered. The changes in tumor volume were measured serially until the 28 or 30 days after transplantation (Day 28 or 30). The tumor volume was calculated from the formula shown in Example 16.

Figure 2:
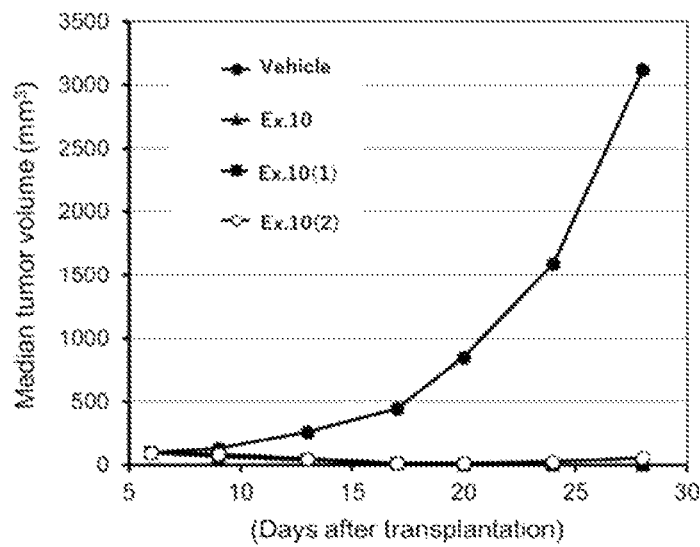
FIG. 2 It shows the antitumor activity of the compound of the present invention (each compound shown in Examples 10, 10 (1) and 10 (2)) in the subcutaneous tumor model bearing mouse colon cancer cell line MC38. A vehicle and the compounds of the present invention (n=8) were administered 7 days after the MC38 transplantation, respectively, and the change in tumor volume was continuously measured until 28 days after the transplantation.
Figure 3:
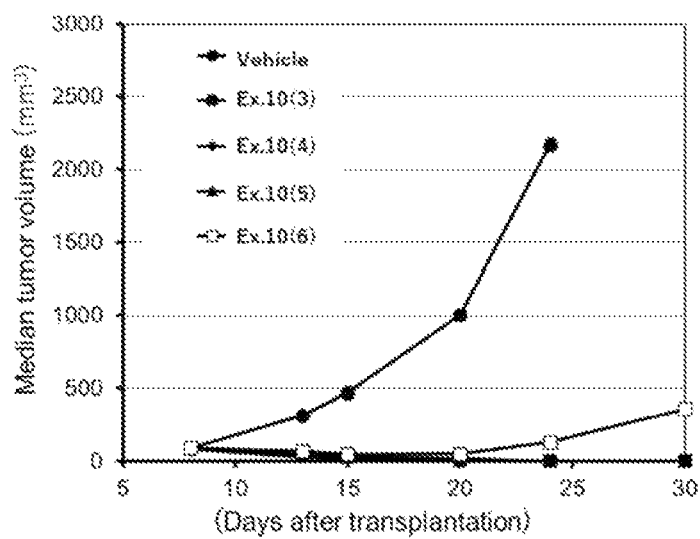
FIG. 3 It shows the antitumor activity of the compounds of the present invention (each compound shown in Examples 10 (3) to 10 (6)) in the subcutaneous tumor model bearing mouse colon cancer cell line MC38. A vehicle and the compounds of the present invention (n=6) were administered 8 days after the MC38 transplantation, respectively, and the change in tumor volume was continuously measured until 30 days after the transplantation.

FIGS. 2 and 3 showed their results.
All the compounds represented in Examples 10 and 10(1) to 10(6) suppressed tumor growth at the above doses. That is, in the groups to which the respective compounds represented in Examples 10 and 10(1) to 10(6) were administered, the median tumor volumes were less than 500 mm$^3$ even 30 days after transplantation.

Formulation Example

Formulation Example 1

The following components are mixed in a conventional method and punched out to obtain 10,000 tablets containing 5 mg of the active ingredient per tablet.

| | |
|---|---|
| Methyl 2-amino-5-(3-amino-7-(1H-pyrazol-4-yl)isoxazolo[4,5-c]pyridin-4-yl)-4-fluorobenzoate | 50 g |
| Carboxymethylcellulose calcium | 20 g |
| Magnesium stearate | 10 g |
| Microcrystalline cellulose | 920 g |

Formulation Example 2

The following components are mixed by a conventional method, then of which the solutions are sterilized by a conventional method, of which 5 mL are filled in ampoules and lyophilized by a conventional method to obtain 10,000 ampules containing 20 mg of the active ingredient per ampoule.

| | |
|---|---|
| Methyl 2-amino-5-(3-amino-7-(1H-pyrazol-4-yl)isoxazolo[4,5-c]pyridin-4-yl)-4-fluorobenzoate | 200 g |
| Mannitol | 20 g |
| Distilled water | 50 L |

INDUSTRIAL AVAILABILITY

Since the compound of the present invention has agonistic activity to STING, a drug containing the compound as an active ingredient is useful as an agent for suppressing the progression of, suppressing the recurrence of and/or treating cancer or infectious disease.

The invention claimed is:

1. A method for suppressing the progression of, suppressing the recurrence of, or treating cancer in a subject in need thereof, comprising administering to the subject an effective amount of (4-(4-(5-acetyl-4-amino-2-fluorophenyl)-3-aminoisoxazolo [4,5-c]pyridin-7-yl)-1H-pyrazol-1-yl)methyl dihydrogen phosphate, a pharmaceutically acceptable salt thereof or a solvate thereof.

2. The method according to claim 1, further comprising administering one or more anti-cancer drugs to the subject.

3. The method according to claim 2, wherein the anti-cancer drug is an anti-PD-1 antibody or anti-PD-L1 antibody.

4. The method according to claim 1, wherein the cancer is solid cancer or blood cancer.

5. The method according to claim 1, wherein the solvate is a hydrate.

6. The method according to claim 4, wherein the solid cancer is one or more cancers selected from malignant melanoma, non-small cell lung cancer, small cell lung cancer, head and neck cancer, renal cell cancer, breast cancer, ovarian cancer, ovarian clear cell adenocarcinoma, nasopharyngeal cancer, uterine cancer, anal cancer, colorectal cancer, rectal cancer, colon cancer, hepatocellular carcinoma, esophageal cancer, gastric cancer, esophagogastric junction cancer, pancreatic cancer, urine urothelial cancer, prostate cancer, fallopian tube cancer, primary peritoneal cancer, malignant pleural mesothelioma, gallbladder cancer, bile duct cancer, biliary tract cancer, skin cancer, testicular cancer (germ cell tumor), vaginal cancer, vulvar cancer, penile cancer, small intestine cancer, endocrine system cancer, thyroid cancer, parathyroid cancer, adrenal carcinoma, spinal tumor, neuroblastoma, medulloblastoma, ocular retinoblastoma, neuroendocrine tumor, brain tumor, squamous cell carcinoma, bone/soft tissue sarcoma and Kaposi's sarcoma, and the blood cancer is one or more cancers selected from multiple myeloma, malignant lymphoma, leukemia, central nervous system malignant lymphoma, myelodysplastic syndromes, and myeloproliferative syndromes.

7. A method for stimulating STING (Stimulation of Interferon Genes) in a subject in need thereof, comprising administering to the subject an effective amount of (4-(4-(5-acetyl-4-amino-2-fluorophenyl)-3-aminoisoxazolo [4,5-c]pyridin-7-yl)-1H-pyrazol-1-yl)methyl dihydrogen phosphate, a pharmaceutically acceptable salt thereof or a solvate thereof.

8. The method according to claim 7, wherein the solvate is a hydrate.

* * * * *

UNITED STATES PATENT AND TRADEMARK OFFICE
CERTIFICATE OF CORRECTION

PATENT NO. : 12,152,049 B2
APPLICATION NO. : 18/339506
DATED : November 26, 2024
INVENTOR(S) : Ryosuke Hanada et al.

It is certified that error appears in the above-identified patent and that said Letters Patent is hereby corrected as shown below:

In the Claims

In Claim 1, Column 74, Lines 1-2, delete "(4-(4-(5-acetyl-4-amino-2-fluorophenyl)-3-aminoisoxazolo [4,5-c]pyridin-7-yl)-1H-pyrazol-1-yl)methyl" and insert --(4-(4-(5-acetyl-4-amino-2-fluorophenyl)-3-aminoisoxazolo[4,5-c]pyridin-7-yl)-1H-pyrazol-1-yl)methyl-- therefor; and In Claim 7, Column 74, Lines 38-40, delete "(4-(4-(5-acetyl-4-amino-2-fluorophenyl)-3-aminoisoxazolo [4,5-c]pyridin-7-yl)-1H-pyrazol-1-yl)methyl" and insert --(4-(4-(5-acetyl-4-amino-2-fluorophenyl)-3-aminoisoxazolo[4,5-c]pyridin-7-yl)-1H-pyrazol-1-yl)methyl-- therefor.

Signed and Sealed this
Twenty-fourth Day of June, 2025

Coke Morgan Stewart
*Acting Director of the United States Patent and Trademark Office*